US011179373B2

(12) United States Patent
Ciulli et al.

(10) Patent No.: US 11,179,373 B2
(45) Date of Patent: Nov. 23, 2021

(54) DERIVATIVES OF 1-[(CYCLOPENTYL OR 2-PYRROLIDINYL) CARBONYLAMINOMETHYL]-4-(L,3-THIAZOL-5-YL) BENZENE WHICH ARE USEFUL FOR THE TREATMENT OF PROLIFERATIVE, AUTOIMMUNE OR INFLAMMATORY DISEASES

(71) Applicant: University of Dundee, Dundee (GB)

(72) Inventors: Alessio Ciulli, Dundee (GB); Michael Zengerle, Ebertsheim (DE); Kwok-Ho Chan, Dundee (GB)

(73) Assignee: University of Dundee, Dundee (GB)

( * ) Notice: Subject to any disclaimer, the term of this patent is extended or adjusted under 35 U.S.C. 154(b) by 0 days.

(21) Appl. No.: 15/557,525

(22) PCT Filed: Mar. 14, 2016

(86) PCT No.: PCT/GB2016/050691
§ 371 (c)(1),
(2) Date: Sep. 12, 2017

(87) PCT Pub. No.: WO2016/146985
PCT Pub. Date: Sep. 22, 2016

(65) Prior Publication Data
US 2018/0050021 A1 Feb. 22, 2018

(30) Foreign Application Priority Data

Mar. 13, 2015 (GB) .................... 1504314
Dec. 11, 2015 (GB) .................... 1521858

(51) Int. Cl.
| | |
|---|---|
| A61K 31/426 | (2006.01) |
| A61K 31/4025 | (2006.01) |
| A61K 31/4196 | (2006.01) |
| A61K 31/381 | (2006.01) |
| A61K 31/551 | (2006.01) |
| A61K 31/16 | (2006.01) |
| C07D 417/14 | (2006.01) |
| C07D 417/12 | (2006.01) |
| C07D 487/04 | (2006.01) |
| C07D 495/14 | (2006.01) |

(52) U.S. Cl.
CPC ............ *A61K 31/426* (2013.01); *A61K 31/16* (2013.01); *A61K 31/381* (2013.01); *A61K 31/4025* (2013.01); *A61K 31/4196* (2013.01); *A61K 31/551* (2013.01); *C07D 417/12* (2013.01); *C07D 417/14* (2013.01); *C07D 487/04* (2013.01); *C07D 495/14* (2013.01)

(58) Field of Classification Search
None
See application file for complete search history.

(56) References Cited

U.S. PATENT DOCUMENTS

2017/0065719 A1* 3/2017 Qian .................... A61K 45/06
2017/0327469 A1* 11/2017 Crew .................... C07D 413/14

FOREIGN PATENT DOCUMENTS

| | | |
|---|---|---|
| JP | 2015-508414 A | 3/2015 |
| JP | 2018-502925 A | 2/2018 |
| WO | 2002/20740 | 3/2002 |
| WO | 2013106643 A2 | 7/2013 |
| WO | 2013106646 A2 | 7/2013 |
| WO | 2014/108452 | 7/2014 |
| WO | 2015/000867 A | 1/2015 |
| WO | WO2015000868 * | 1/2015 |
| WO | 2016118666 A1 | 7/2016 |

OTHER PUBLICATIONS

Schafer, S., Kolkhof, P. Failure is an option: learning from unsuccessful proof-of-concept trials. Drug Discovery Today. Nov. 2008,13, 913-916.*
Horig, H., Pullman, W. From bench to clinic and back: Perspective on the 1st IQPC Translational Research conference. Journal of Translational Medicine. Dec. 2004, 2, 44.*
Zengerle et al., Selective Small Molecule Induced Degradation of the BET Bromodomain Protein BRD4. ACS Chemical Biology, 2015, 10, 1770-1777.*
International Search Report for PCT/GB2016/050691, dated May 23, 2016.
Baud, Matthias G.J., et al., "A bump-and-hole approach to engineer controlled selectivity of BET bromodomain chemical probes", Chemical Biology, vol. 346, Issue 6209 (Oct. 31, 2014), pp. 638-641.
Mayer, J., et al., "Hydrolysis in drug and prodrug metabolism", Chemistry, Biochemistry and Enzymology, John Wiley & Sons, Ltd. (2003).

(Continued)

*Primary Examiner* — Po-Chih Chen
(74) *Attorney, Agent, or Firm* — Barnes & Thornburg LLP

(57) ABSTRACT

There is provided novel small molecule E3 ubiquitin ligase protein binding ligand compounds, having utility in PROteolysis Targeted Chimeras (PROTACs), as well as processes for the preparation thereof, and use in medicine. There is particularly provided PROTACs which bind to a protein within the bromo- and Extra-terminal (BET) family of proteins, and especially to PROTACs including novel small molecule E3 ubiquitin ligase protein binding ligand compounds which selectively induce degradation of the BRD4 protein within the bromodomain of the BET family of proteins.

10 Claims, 13 Drawing Sheets
Specification includes a Sequence Listing.

(56) References Cited

OTHER PUBLICATIONS

Cyrus, K., et al., "Two-headed PROTAC: An effective new tool for targeted protein degradation", ChemBioChem, vol. 11 (2010), pp. 1531-1534.
Sakamoto, K.M., et al., "Developments of PROTACS to target cancer-promoting proteins for ubiquitination and degradation", Molecular and Cellular Proteomics 2.12, (2003), pp. 1350-1358.
Sakamoto, K.M., et al., "PROTACS: Chimeric molecules that targer proteins to the 25 Skp1-Cullin-F box complex for ubiquitination and degradation", Proc. Natl. Acad Sci., vol. 98, No. 15, (2001), pp. 8554-8559.
Schneekloth, J.S., et al., "Chemical genetic control of protein levels: Selective in vivo targeted degradation", J. Am. Chern Soc , vol. 126 (2004), pp. 3748-3754.
Hon, W.-C., et al., "Structural basis for the recognition of hydroxyproline in HIF-1 alpha by pVHL", Nature, vol. 417 (2002), pp. 975-978.
Galdeano, C., et al., "Structure-guided design and optimization of small molecules targeting the protein interaction between the von Hippel-Lindau (VHL) E3 ubiquitin ligase and the hypoxia inducible 15 factor (HIF) alpha subunit with in vitro nanomolar affinities", J. Med. Chem., vol. 57 (2014), pp. 8657-8663.
Filippakopoulos, P., et al., "Selective inhibition of BET bromodomains", Nature, vol. 468 (2010), pp. 1067-1073.
Buckley, D.L., et al., "HaloPROTACS: Use of Small Molecule PROTACs to Induce Degradation of HaloTag Fusion Proteins", ACS Chemical Biology, vol. 10 (2015), pp. 1831-1837.
Bondeson, D.P., "Catalytic in vivo Protein Knockdown by Small-Molecule PROTACs", Nature Chemical Biology, vol. 11 (2015), pp. 611-618.
Lai, A.C., et al., "Modular PROTAC Design for the Degradation of Oncogenic BCR-ABL", Angew. Chern. Int. Ed., vol. 55 (2016), p. 807-810.
Search Report for Application No. GB1521858.9, dated Jan. 13, 2016.
Bundgaard, et al., "Design and application of prodrugs, textbook of drug design and development", Journal of Drug Deliver Reviews, Chapter 5, (1992), vol. 8, pp. 1-38.
Berge, S.M., et al., "Pharmaceutical salts", J. Pharmaceutical Sciences, vol. 66 (1977), pp. 1-19.
Examination Report for corresponding EP Application No. 16 710 312.6, dated Jun. 5, 2020.
Japanese Office Action for JP Application No. 2017-566216, dated Dec. 3, 2019 (Full English Translation).
Gosmini, R., et al., "The discovery of I-BET726 (GSK1324726A), a potent tetrahydroquinoline ApoA1 up-regulator and selective BET bromodomain inhibitor", Journal of Medicinal Chemistry (Oct. 2014), vol. 57, No. 19, pp. 8111-8131.
Zhao, Y., et al., "The making of I-BET762, a BET bromodomain inhibitor now in clinical development", Journal of Medicinal Chemistry (Oct. 2013), vol. 56, No. 19, pp. 7498-7500.
Japanese Office Action for JP Application No. 2017-566216, dated Jul. 21, 2020 (Full English Translation).
Examination Report from corresponding EP Application No. 16 710 312.6, dated Dec. 1, 2020.
Buckley, D.L., et al., "Small-Molecule Inhibitors of the Interaction between the E3 Ligase VHL and HIF1a", Angew. Chem. Int. Ed. (2012), vol. 51, pp. 11463-11467.

\* cited by examiner

DERIVATIVES OF 1-[(CYCLOPENTYL OR 2-PYRROLIDINYL) CARBONYLAMINOMETHYL]-4-(L,3-THIAZOL-5-YL) BENZENE WHICH ARE USEFUL FOR THE TREATMENT OF PROLIFERATIVE, AUTOIMMUNE OR INFLAMMATORY DISEASES

This application is a National Stage application of International Application No. PCT/GB2016/050691 filed Mar. 14, 2016. This application also claims priority under 35 U.S.C. § 119 to GB Patent Application No. 1504314.4, filed Mar. 13, 2015 and GB Patent Application No. 1521858.9, filed Dec. 11, 2015.

FIELD OF THE INVENTION

This invention relates to novel small molecule E3 ubiquitin ligase protein binding ligand compounds, and to their utility in PROteolysis Targeted Chimeras (PROTACs), as well as processes for the preparation thereof, and use in medicine. This invention particularly relates to PROTACs which bind to a protein within the bromo- and Extraterminal (BET) family of proteins, and especially to PROTACs including novel small molecule E3 ubiquitin ligase protein binding ligand compounds which selectively induce degradation of the BRD4 protein within the bromodomain of the BET family of proteins.

BACKGROUND OF THE INVENTION

The Bromo- and Extra-terminal (BET) family of proteins, including the ubiquitously expressed BRD2, BRD3, BRD4 and the testis-specific BRDT, are known to recruit transcriptional regulatory complexes to acetylated chromatin and thereby control specific networks of genes involved in cellular proliferation and in cell cycle progression. Deregulation of BET protein activity, in particular BRD4, has been strongly linked to cancer and inflammatory diseases, making BET proteins attractive drug targets. As well as their potential roles in transcriptional regulation, epigenetics and cancer the Bromo- and Extra-terminal (BET) family of proteins BRD2, BRD3 and BRD4 are thought to play an important role in epigenetics and are the targets of the pan-BET selective bromodomain inhibitor JQ1.

RNAi screens have identified BRD4 as a therapeutic target in acute myeloid leukaemia and ovarian carcinoma. In addition siRNA knock-down of BRD4, but not of BRD2 or BRD3, has been shown to induce upregulation of apolipoprotein A1 (ApoA1), which is thought to protect from atherosclerosis progression and other inflammatory processes. This knock-down, or silencing, of BRD4 has identified BRD4 as a potential target in the search for treatments of chronic obstructive pulmonary disease (COPD).

In target validation, the use of small molecule chemical probes or inhibitors, acting at the posttranslational level, holds several advantages over genetic techniques such as dominant-negative mutants or knockouts and RNAi knockdowns. These advantages include the provision of spatial and temporal control in a reversible fashion. Crucial to the function of BET proteins are two highly homologous bromodomains, which are present in the amino-terminal regions of the BET proteins, and which direct recruitment to nucleosomes by binding to specific acetylated lysines ($K_{Ac}$) within histone tails. Small molecule BET inhibitors, including the triazolodiazepine-based JQ1 and I-BET762 are known to bind to the $K_{Ac}$-binding pocket of these bromodomains and to disrupt interaction with histones, and thereby displace BET proteins and their associated transcriptional regulatory complexes from chromatin. These BET inhibitors JQ1 and I-BET762 are highly potent ($K_d$~100 nM), cell-penetrant and active in vitro and in vivo against a range of solid, haematological and other tumours, which has prompted BET inhibitor compounds entering Phase I clinical trials for cancer.

Therapeutically, the effects of the known_BET inhibitors on multiple transcriptional pathways have raised concerns about the safety and tolerability of BET inhibitors in humans. Crucially none of the BET inhibitors described to date has selective effects on the BRD4 bromodomains over those of its paralogs BRD2 and BRD3. Thus there is a need for new BET inhibitors which have selective effects on BRD4 bromodomains over those of its paralogs BRD2 and BRD3. Thus it would be desirable to develop compounds which provide intra-BED selective impact, and in particular for new BET inhibitor compounds which are selective for BRD4 bromodomains over those of its paralogs BRD2 and BRD3.

To date, no BET inhibitors have shown intra-BET selectivity for individual BET family members. Not only has this prevented the development of BET-inhibitor-based therapies per se, it significantly limits their scope as chemical probes for validating the roles of individual BET targets in physiology and disease. In an attempt to address this issue, chemical genetic strategies have been recently developed to engineer orthogonal selective BET bromodomain-ligand pairs, such as that described in Baud, M. G. J. et al. "A bump-and-hole approach to engineer controlled selectivity of BET bromodomain chemical probes", Science 346, 638-41 (2014). Whilst the Baud approach has the advantage of enabling disruption at will of a single or more bromodomains, it requires a mutation to be introduced into the target protein, and as a result cannot be developed into a drug of itself.

This lack of intra-BET selectivity has limited the scope for the potential utility of current inhibitors as probes for target validation, particularly due to concerns about potential unwanted side effects or toxicity in a therapeutic setting. Thus it would be desirable to provide BET inhibitor compounds which are both selective for one or more bromodomains within the BET family of proteins and which are suitable for use as drugs i.e. pharmaceutically, bio-pharmaceutically, veterinarily active compounds.

A general limitation associated with conventional occupancy-driven target inhibition approaches is that they often demands systemic target engagement, requiring sustained high concentration of a potent small molecule inhibitor over a prolonged time. This in turn enhances off-target effects and can lead to unwanted side effects or toxicity in a therapeutic setting.

The Applicant has developed an alternative small molecule approach which delivers against the long-felt want for a selective BET inhibitor, and which also overcomes the prior-issues associated with systemic target engagement. In particular, the Applicant has now developed new compounds that can remove BET proteins entirely from cells as opposed to just inhibiting them. Not only does this provide novel BET inhibitor compounds for use in the development of new medicines, it also provides new tools for studying BET bromodomain proteins and validating them as drug targets.

SUMMARY OF THE INVENTION

The Applicant has now developed PROteolysis Targeted Chimeric compounds (PROTACs) having the structure A-L-B that can tether a bromodomain inhibitor, such as for example JQ1, via a moiety which binds to a protein within the bromo- and Extra-terminal (BET) family of proteins (B) to a small molecule E3 ubiquitin ligase protein binding ligand compound (A) of formula I, such as for example a VHL-E3 ubiquitin ligase binding ligand compound of formula I, via suitable linker (L). In particular the PROTACs of the present invention are capable of binding to include to a protein within the bromo- and Extra-terminal (BET) family of proteins independently selected from: BRD2, BRD3 and BRD4, and especially selectively induces degradation of the BRD4 protein within the bromo- and Extra-terminal (BET) family of proteins, and preferably wherein B is independently selected from: JQ1; -I-BET 726; I-BET 762.

According to a first aspect the present invention provides compounds having the structure A-L-B wherein A is an E3 ubiquitin ligase protein binding ligand compound of formula I:

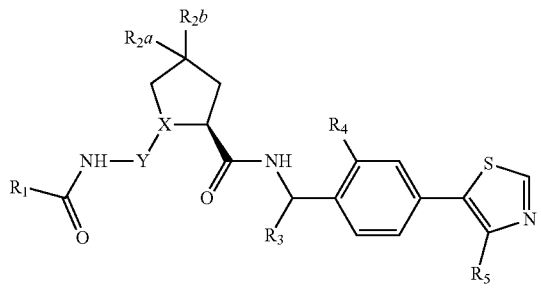

wherein L is a group which is directly bonded to the compound of formula I and wherein L is —(CH$_2$)$_n$L$^1$(CH$_2$O)$_p$—, wherein L$^1$ is a covalent bond, a 5 or 6 membered heterocyclic or heteroaromatic ring containing 1, 2 or 3 nitrogen atoms, phenyl, —(C$_2$-C$_4$)alkyne, —SO$_2$—, or —NH—,
wherein X is C or N,
  wherein n and p are independently 0 to 10,
  wherein R$^1$ is a —(CH$_2$)$_m$Q$_v$ group with a covalent C-linked bond to L, a (C$_1$-C$_4$) alkyl group, or a C-linked (C$_3$-C$_4$) heterocyclic group,
  wherein m is 0, 1 or 2 and v is 0 or 1, wherein when m is 0, v is 1,
  wherein Q is a (C$_3$-C$_4$)—C-linked nitrogen containing heterocyclic group, wherein one of the ring atoms in the Q group is optionally substituted with a —NHC(O) group or a —C(O) group,
  wherein said R$^1$ groups may be optionally substituted by one or more groups independently selected from F, CN or C(O),
  wherein R$^{2a}$ is OH, —CHF$_2$, —CF$_3$, NH$_2$ or F,
  wherein R$^{2b}$ is H or F,
  wherein R$^3$ and R$^4$ are independently selected from H, a covalent C-linked, a covalent O-linked, or a covalent C(O)-linked bond to L,
  R$^5$ is a —(C$_1$-C$_3$) alkyl group or a covalent C-linked bond to L,
  wherein Y is

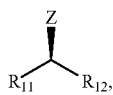

wherein Z is CR$^6$R$^7$R$^8$ or SR$^6$R$^7$R$^8$R$^9$R$^{10}$,
wherein R$^{11}$ is a covalent C-linked bond or a

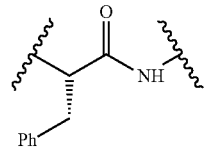

group
  wherein R$^{12}$ is —C(O)—, —C(S)— or a —C(=)—R$^{13}$ group,
  wherein when Z is CR$^6$R$^7$R$^8$, R$^6$ and R$^7$ are each independently —(C$_1$-C$_3$) alkyl groups or wherein R$^6$ and R$^7$ together with the C-atom to which they are attached form a —(C$_3$-C$_4$) cycloalkyl group,
  wherein when Z is CR$^6$R$^7$R$^8$, R$^8$ is a —(C$_1$-C$_3$) alkyl group, a —(CH$_2$)$_q$R$^{8*}$ group wherein q is 0, 1 or 2, a —C(O)—R$^{8*}$ group, or a —N(H)—R$^{8*}$ group,
  and wherein R$^{8*}$ is a covalent C-linked bond to L or H,
  or wherein when Z is SR$^6$R$^7$R$^8$R$^9$R$^{10}$, R$^6$, R$^7$, R$^8$, R$^9$ and R$^{10}$ are each independently selected from: F; or —(C$_1$-C$_3$) alkyl groups,
  wherein R$^{13}$ is H, F or a —(C$_1$-C$_3$) alkyl group,
  wherein the —(C$_1$-C$_3$) alkyl groups, or —(C$_3$-C$_4$) cycloalkyl groups where present in a Y group are optionally substituted by one or more substituents independently selected from: methyl; OH; or F,
  and wherein B is an additional optional ligand which binds to a target protein or polypeptide which is to be degraded by ubiquitin ligase and is linked to A though a —C-linkage to the L group,
  or a pharmaceutically acceptable, salt, enantiomer, stereoisomer, hydrate, solvate, or polymorph thereof.

The present invention provides compounds having the structure A-L-B wherein A is an E3 ubiquitin ligase protein binding ligand compound of formula I wherein L is —(CH$_2$)$_n$L$^1$(CH$_2$O)$_p$—, wherein L$^1$ is a covalent bond, a 5 or 6 membered heterocyclic or heteroaromatic ring containing 1, 2 or 3 nitrogen atoms, phenyl, —(C$_2$-C$_4$) alkyne, —SO$_2$—, or —NH—, wherein X is C or N, wherein n and p are independently 0 to 10, wherein R$^1$ is a —(CH$_2$)$_m$Q$_v$ group with a covalent C-linked bond to L, a (C$_1$-C$_4$) alkyl group, or a C-linked (C$_3$-C$_4$) heterocyclic group, wherein m is 0, 1 or 2 and v is 0 or 1, wherein when m is 0, v is 1, wherein Q is a (C$_3$-C$_4$)—C-linked nitrogen containing heterocyclic group, wherein one of the ring atoms in the Q group is optionally substituted with a —NHC(O) group or a —C(O) group, wherein said R$^1$ groups may be optionally substituted by one or more groups independently selected from F, CN or C(O), wherein R$^{2a}$ is OH, —CHF$_2$, —CF$_3$, NH$_2$ or F, wherein R$^{2b}$ is H or F, wherein R$^3$ and R$^4$ are independently selected from H, a covalent C-linked, a covalent O-linked, or a covalent C(O)-linked bond to L, wherein R$^5$ is a —(C$_1$-C$_3$) alkyl group or a covalent C-linked bond to L, wherein Y is

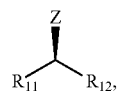

wherein Z is CR$^6$R$^7$R$^8$ or SR$^6$R$^7$R$^8$R$^9$R$^{10}$, wherein R$^{11}$ is a covalent C-linked bond or a

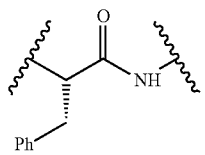

group, wherein $R^{12}$ is a —C(O)—, —C(S)— or —C(=)—$R^{13}$ group, wherein when Z is $CR^6R^7R^8$, $R^6$ and $R^7$ are each independently —($C_1$-$C_3$) alkyl groups or wherein $R^6$ and $R^7$ together with the C-atom to which they are attached form a —($C_3$-$C_4$) cycloalkyl group, wherein when Z is $CR^6R^7R^8$, $R^8$ is a —($C_1$-$C_3$) alkyl group, a —$(CH_2)_q R^{8*}$ group wherein q is 0, 1 or 2, a —C(O)—$R^{8*}$ group, a —N(H)—$R^{8*}$ group, and wherein $R^{8*}$ is a covalent C- or N-linked bond to L or H, or wherein when Z is $SR^6R^7R^8R^9R^{10}$, $R^6$, $R^7$, $R^8$, $R^9$ and $R^{10}$ are each independently selected from: F; or —($C_1$-$C_3$) alkyl groups, wherein $R^{13}$ is H, F or a —($C_1$-$C_3$) alkyl group, and wherein the —($C_1$-$C_3$) alkyl groups, or —($C_3$-$C_4$) cycloalkyl groups where present in a Y group are optionally substituted by one or more substituents independently selected from: methyl; OH; or F, and wherein B is a ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

The present invention provides compounds having the structure A-L-B wherein A is an E3 ubiquitin ligase protein binding ligand compound of formula I, and L is a linker as detailed in either of the aspects detailed above and wherein B is present, and wherein B is a chemical moiety which binds to a protein within the bromo- and Extra-terminal (BET) family of proteins.

The present invention provides compounds having the structure A-L-B wherein A is an E3 ubiquitin ligase protein binding ligand compound of formula I, and L is a linker in accordance with any of the aspects as detailed above, wherein Y is

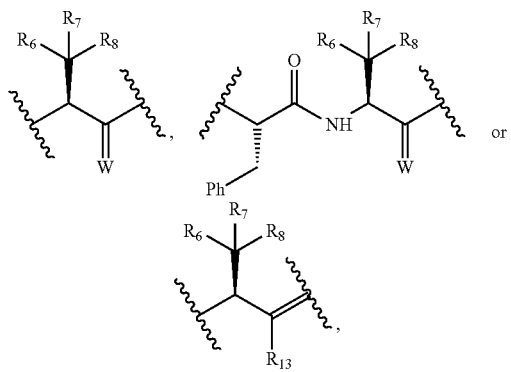

wherein W may be O or S.

The present invention provides compounds having the structure A-L-B wherein A is an E3 ubiquitin ligase protein binding ligand compound of formula I, and L is a linker in accordance with any of the aspects as detailed above, wherein A has the general formula IA

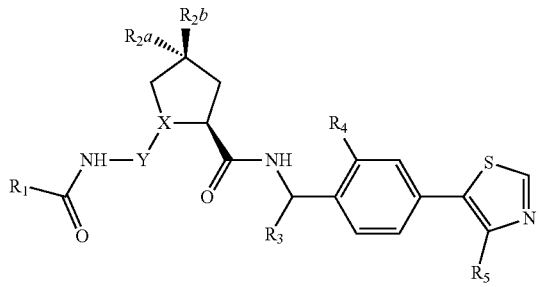

IA wherein $R^1$ to $R^5$, X, Y, L and B are in accordance with any of the aspects defined herein.

The present invention provides compounds having the structure A-L-B wherein A is an E3 ubiquitin ligase protein binding ligand compound of formula I or IA, and L is a linker in accordance with any of the aspects as detailed above, wherein B is a chemical moiety which selectively induces degradation of the BRD4 protein within the bromo- and Extra-terminal (BET) family of proteins, and optionally wherein B is independently selected from: JQ1; -I-BET 726; I-BET 762.

The present invention provides PROTAC compounds of formula I which bind to a protein within the bromo- and Extra-terminal (BET) family of proteins, preferably PROTAC compounds of formula 1 which bind to a protein within the bromo- and Extra-terminal (BET) family of proteins independently selected from: BRD2, BRD3 and BRD4, and particularly PROTAC compounds of formula I which selectively induces degradation of the BRD4 protein within the bromo- and Extra-terminal (BET) family of proteins.

The present invention also provides PROTAC compounds of formula I for use in medicine, particularly for use in conditions or diseases where binding to a protein within the bromo- and Extra-terminal (BET) family of proteins independently selected from: BRD2, BRD3 and BRD4 is implicated, and especially for use in the treatment of one or more conditions or diseases independently selected from: cancer; benign proliferative disorders; infection or non-infectious inflammatory events; autoimmune diseases; inflammatory diseases; systemic inflammatory response syndromes; viral infections and diseases; opthamological conditions.

In another aspect, the present invention provides a pharmaceutical composition comprising one or more PROTAC compounds of formula I and a pharmaceutically acceptable carrier, vehicle or diluent therefor.

The above aspects of the present invention, as well as further aspects are detailed hereinafter.

DESCRIPTION OF THE INVENTION

Described herein is the novel small molecule approach, as developed by the Applicant which uses PROTAC compounds of structure A-L-B, which has been demonstrated to achieve rapid, effective and prolonged intracellular degradation of BET bromodomain proteins. The PROTAC-induced protein degradation potential of the present compounds has been confirmed for binding to VHL, has been demonstrated to be reversed upon blocking proteasome activity, and has been demonstrated to not interfere with the endogenous, physiological levels of VHL and of its natural substrate HIF-1α. Experiments using PROTAC compounds of structure A-L-B, have confirmed that all investigated compounds showed preferential degradation of BRD4 over BRD2 and BRD3 at low concentrations.

In addition, the downstream gene expression pattern resulting from treatment with a potent and selective PROTAC compound of formula A-L-B, MZ1, has been shown to be similar to JQ1 inhibition for BRD4-dependent genes MYC, P21 and AREG but not for FAS, FGFR1 and TYRO3.

As detailed hereinafter the experimental results for PROTACs in accordance with the present invention, suggest a different pharmacological response resulting from selectively depleting BRD4 with MZ1 compared to inhibiting the whole BET protein subfamily with JQ1. Without wishing to be bound to any particular theory, as additional experiments have confirmed that no preference for binding the bromodomains of BRD4 over the highly homologous bromodomains of BRD2 and BRD3 was observed by ITC within the context of the purified proteins, it is proposed herein that the observed selectivity could arise from preferential and more efficient poly-ubiquitination of lysine residues on the surface of BRD4 compared to those of BRD2 and BRD3. Alternatively or in addition, we also propose that preferential direct interaction between VHL and BRD4 compared to BRD2/3 may occur as a result of binding to PROTAC compounds of the present invention, triggering a more productive formation of a VHL:PROTAC:BRD4 ternary complex.

As indicated hereinbefore the Applicant has developed PROTAC compounds having the structure A-L-B wherein A is an E3 ubiquitin ligase protein binding ligand compound of formula I:

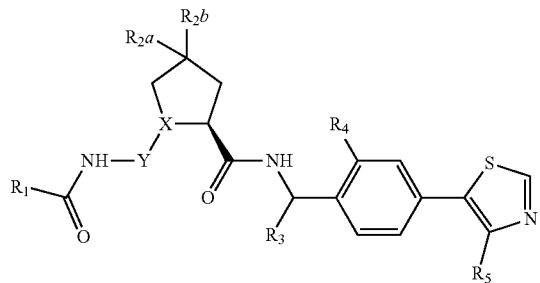

I wherein L is a group which is directly bonded to the compound of formula I and wherein L is $-(CH_2)_nL^1(CH_2O)_p-$, wherein $L^1$ is a covalent bond, a 5 or 6 membered heterocyclic or heteroaromatic ring containing 1, 2 or 3 nitrogen atoms, phenyl, $-(C_2-C_4)$alkyne, $-SO_2-$, or $-NH-$,
wherein X is C or N,
  wherein n and p are independently 0 to 10,
  wherein $R^1$ is a $-(CH_2)_mQ_v$ group with a covalent C-linked bond to L, a $(C_1-C_4)$ alkyl group, or a C-linked $(C_3-C_4)$ heterocyclic group,
  wherein m is 0, 1 or 2 and v is 0 or 1, wherein when m is 0, v is 1,
  wherein Q is a $(C_3-C_4)$—C-linked nitrogen containing heterocyclic group, wherein one of the ring atoms in the Q group is optionally substituted with a $-NHC(O)$ group or a $-C(O)$ group,
  wherein said $R^1$ groups may be optionally substituted by one or more groups independently selected from F, CN or C(O),wherein $R^{2a}$ is OH, $-CHF_2$, $-CF_3$, $NH_2$ or F, wherein $R^{2b}$ is H or F,
wherein $R^3$ and $R^4$ are independently selected from H, a covalent C-linked, a covalent O-linked, or a covalent C(O)-linked bond to L,
$R^5$ is a $-(C_1-C_3)$ alkyl group or a covalent C-linked bond to L,
wherein Y is

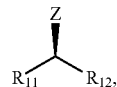

wherein Z is $CR^6R^7R^8$ or $SR^6R^7R^8R^9R^{10}$,
wherein $R^{11}$ is a covalent C-linked bond or a

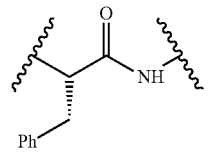

group
  wherein $R^{12}$ is $-C(O)-$, $-C(S)-$ or a $-C(=)-R^{13}$ group,
  wherein when Z is $CR^6R^7R^8$, $R^6$ and $R^7$ are each independently $-(C_1-C_3)$ alkyl groups or wherein $R^6$ and $R^7$ together with the C-atom to which they are attached form a $-(C_3-C_4)$ cycloalkyl group,
  wherein when Z is $CR^6R^7R^8$, $R^8$ is a $-(C_1-C_3)$ alkyl group, a $-(CH_2)_qR^{8*}$ group wherein q is 0, 1 or 2, a $-C(O)-R^{8*}$ group, or a $-N(H)-R^{8*}$ group,
  and wherein $R^{8*}$ is a covalent C-linked bond to L or H,
  or wherein when Z is $SR^6R^7R^8R^9R^{10}$, $R^6$, $R^7$, $R^8$, $R^9$ and $R^{10}$ are each independently selected from: F; or $-(C_1-C_3)$ alkyl groups,
  wherein $R^{13}$ is H, F or a $-(C_1-C_3)$ alkyl group, and
  wherein the $-(C_1-C_3)$ alkyl groups, or $-(C_3-C_4)$ cycloalkyl groups where present in a Y group are optionally substituted by one or more substituents independently selected from: methyl; OH; or F,
  and wherein B is an additional optional ligand which binds to a target protein or polypeptide which is to be degraded by ubiquitin ligase and is linked to A though a $-C$-linkage to the L group,
or a pharmaceutically acceptable, salt, enantiomer, stereoisomer, hydrate, solvate, or polymorph thereof.

Advantageously, the novel small molecule E3 binding ligands of formula I, or formula IA as detailed herein are capable of being linked to the target protein binding ligand B, via linker L at a number of different positions on I or IA, via a covalent C-linked bond to L at the $R^1$, $R^3$, $R^4$, $R^5$, or $R^8$ positions. Thus, according to a further aspect the present invention provides having the structure A-L-B wherein A is an E3 ubiquitin ligase protein binding ligand compound of formula I, or formula IA wherein A is linked to B via a covalent bond between A and L at a position on the compound of formula I or formula IA independently selected from: $R^1$, $R^3$, $R^4$, $R^5$, or $R^8$ as defined herein.

The present invention provides compounds having the structure A-L-B wherein A is an E3 ubiquitin ligase protein binding ligand compound of formula I wherein
L is a $-(CH_2)_n(CH_2O)_p-$ group which is directly bonded to the compound of formula I, wherein X is C or N, wherein n and p have the same value and are between 1 to 6, wherein $R^1$ is a —$(CH_2)_m$ group with a covalent C-linked bond to L, or a $C_1$-$C_4$ alkyl group, wherein m is 1 or 2, wherein $R^{2a}$ is OH, —$CHF_2$, or F, wherein $R^{2b}$ is H or F, wherein $R^3$ and $R^4$ are independently selected from H or a covalent C-linked bond to L bond, wherein $R^5$ is a —($C_1$-$C_3$) alkyl group or a covalent C-linked bond to L, wherein Y is

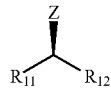

wherein Z is $CR^6R^7R^8$ or $SR^6R^7R^8R^9R^{10}$, wherein $R^{11}$ is a covalent C-linked bond or a

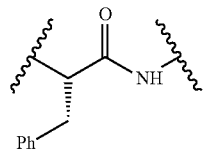

group, wherein $R^{12}$ is a —C(O)— or —C(=)—$R^{13}$ group, wherein when Z is $CR^6R^7R^8$, $R^6$ and $R^7$ are each independently —($C_1$-$C_3$) alkyl groups, or wherein $R^6$ and $R^7$ together with the C-atom to which they are attached form a —($C_3$-$C_4$) cycloalkyl group, and wherein when Z is $CR^6R^7R^8$, $R^8$ is a —($C_1$-$C_3$) alkyl group, a —$(CH_2)_qR^{8*}$ group, a —C(O)—$R^{8*}$ group, a —N(H)— $R^{8*}$ group, wherein q is 0, 1 or 2 and wherein $R^{8*}$ is a covalent C-linked bond to L or H, and wherein when Z is $SR^6R^7R^8R^9R^{10}$, $R^6$, $R^7$, $R^8$, $R^9$ and $R^{10}$ are each independently selected from: F or —($C_1$-$C_3$) alkyl groups, wherein $R^{13}$ is H, F or a —($C_1$-$C_3$) alkyl group, wherein the —($C_1$-$C_3$) alkyl groups, or —($C_3$-$C_4$) cycloalkyl groups are optionally substituted by one or more substituents independently selected from: methyl; OH; or F, and wherein B is an additional optional ligand which binds to a target protein or polypeptide which is to be degraded by ubiquitin ligase and is linked to A though a —C-linkage to the L group, or a pharmaceutically acceptable, salt, enantiomer, stereoisomer, hydrate, solvate, or polymorph thereof.

The present invention provides compounds having the structure A-L-B wherein A is an E3 ubiquitin ligase protein binding ligand compound of formula I, and L is a linker as detailed hereinbefore and wherein B is present.

The present invention provides compounds having the structure A-L-B wherein A is an E3 ubiquitin ligase protein binding ligand compound of formula I, and L is a linker in accordance with any of the aspects as detailed above, wherein Y is

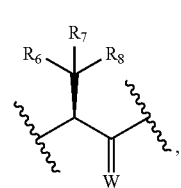

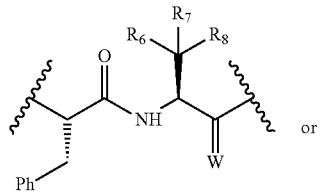

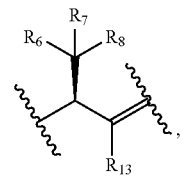

wherein $R^6$ $R^7$, $R^8$ and $R^{13}$ are as defined hereinbefore and wherein W may be O or S.

In a preferred group of compounds of Formula I for use in PROTACs of structure A-L-B as defined hereinbefore, Y is $Y_A$, $Y_B$, or $Y_C$, preferably wherein Y is $Y_A$ or $Y_B$ and more preferably wherein Y is $Y_A$ or $Y_B$ and wherein:
when Y is $Y_A$ W is O and $R^6$, $R^7$ and $R^8$ are methyl groups; and
when Y is $Y_B$ W is O and $R^6$, $R^7$ and $R^8$ are methyl groups.

Thus the present invention provides compounds having the structure A-L-B wherein A is an E3 ubiquitin ligase protein binding ligand compound of formula I, wherein $R^1$ to $R^5$, X, L and B are in accordance with any of the aspects defined herein and wherein Y is $Y_A$, $Y_B$, or $Y_C$, W is O or S, preferably wherein Y is $Y_A$, or $Y_B$ and W is O or S, more preferably wherein when Y is $Y_A$ W is O and $R^6$, $R^7$ and $R^8$ are methyl groups; and when Y is $Y_B$ W is O and $R^6$, $R^7$ and $R^8$ are methyl groups.

In a preferred group of compounds of Formula I for use in PROTACs of structure A-L-B as defined hereinbefore, and wherein L is a —$(CH_2CH_2O)_b$— group which is directly bonded to the compound of formula I wherein b is 1 to 10, preferably 1 to 6, more preferably 1 to 4, and particularly 2, 3 or 4.

Thus the present invention provides compounds having the structure A-L-B wherein A is an E3 ubiquitin ligase protein binding ligand compound of formula I, wherein $R^1$ to $R^5$, X, Y and B are in accordance with any of the aspects defined herein and wherein L is a —$(CH_2CH_2O)_b$— group which is directly bonded to the compound of formula I, wherein b is 1 to 10, preferably 1 to 6, more preferably 1 to 4, and particularly 2, 3 or 4.

The present invention provides compounds having the structure A-L-B wherein A is an E3 ubiquitin ligase protein binding ligand compound of formula I, and preferably wherein A is an E3 ubiquitin ligase protein binding ligand compound of formula IA as defined hereinafter, wherein L is a —$(CH_2CH_2O)_b$— group which is directly bonded to the compound of formula I at the $R^1$ position
wherein X is N,
wherein b is 1 to 10, preferably 1 to 6, more preferably 1 to 4, and particularly 2, 3 or 4,
wherein $R^1$ is a covalent C-linked bond to L,
wherein $R^{2a}$ is OH, F, $NH_2$ or $CHF_2$, preferably OH, F or $CHF_2$, more preferably OH,
wherein $R^{2b}$ is H, F or Cl, preferably H or F, more preferably F, wherein $R^3$ and $R^4$ are both H,
wherein $R^5$ is a —$CH_3$ group,
wherein Y is

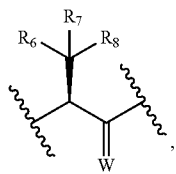 $Y_A$

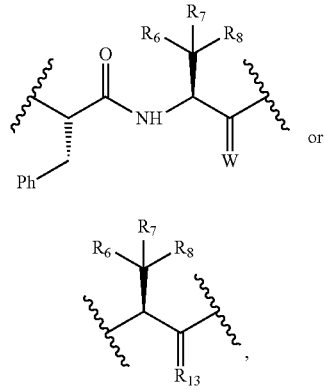 $Y_B$ or

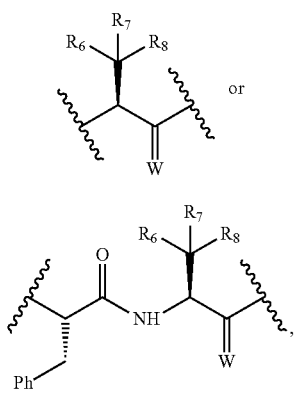 $Y_C$ wherein W may be O or S, wherein $R^6$ $R^7$, $R^8$ and $R^{13}$ are as defined hereinbefore in accordance with any group of compounds, preferred or more preferred group of compounds, and in particular wherein $R^6$, $R^7$, and $R^8$ are each independently $(C_1$-$C_3)$alkyl groups or wherein $R^6$ and $R^7$ together with the C-atom to which they are attached form a $(C_3$-$C_4)$cycloalkyl group, wherein $R^{13}$ is H, F or a $(C_1$-$C_3)$alkyl group, wherein W may be O or S, preferably wherein W is O, and preferably wherein Y is $Y_A$ or $Y_B$ wherein $R^6$, $R^7$, and $R^8$ are each independently $(C_1$-$C_3)$ alkyl groups, more preferably wherein $R^6$, $R^7$, and $R^8$ are all methyl groups and wherein W is O,
and wherein B is an additional optional ligand which binds to a target protein or polypeptide which is to be degraded by ubiquitin ligase and is linked to A though a —C-linkage to the L group,
or a pharmaceutically acceptable, salt, enantiomer, stereoisomer, hydrate, solvate, or polymorph thereof.

There is additionally provided herein compounds having the structure A-L-B wherein A is an E3 ubiquitin ligase protein binding ligand compound of formula I, and preferably wherein A is an E3 ubiquitin ligase protein binding ligand compound of formula IA as defined hereinafter,
wherein L is a —$(CH_2CH_2O)_b$— group which is directly bonded to the compound of formula I at the $R^1$ position,
wherein X is N,
wherein b is 1 to 10, preferably 1 to 6, more preferably 1 to 4, and particularly 2, 3 or 4,
wherein $R^1$ is a covalent C-linked bond to L,
wherein $R^{2a}$ is OH,
wherein $R^{2b}$ is H,
wherein $R^3$ and $R^4$ are both H,
wherein $R^5$ is a —$CH_3$ group,
wherein Y is

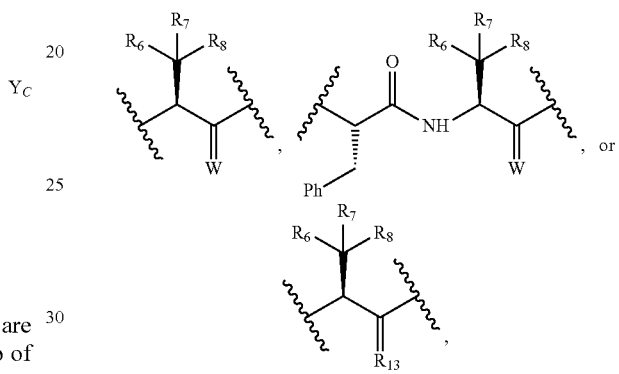 , or

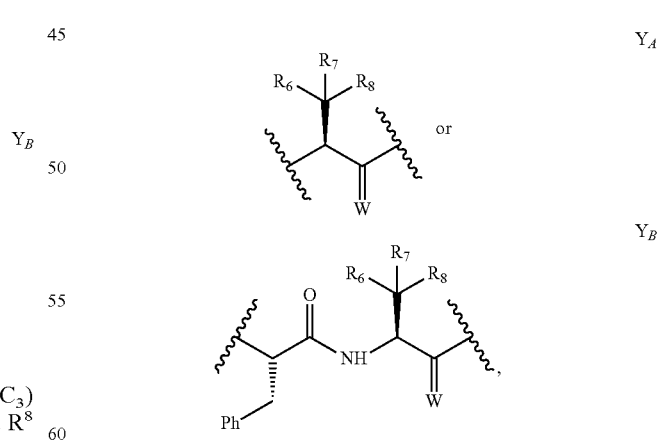

wherein W may be O or S and wherein $R^6$ $R^7$, $R^8$ and $R^{13}$ are as defined hereinbefore in accordance with any group of compounds, preferred or more preferred group of compounds herein, and in particular wherein $R^6$, $R^7$, and $R^8$ are each independently $(C_1$-$C_3)$alkyl groups or wherein $R^6$ and $R^7$ together with the C-atom to which they are attached form a $(C_3$-$C_4)$cycloalkyl group, wherein $R^{13}$ is H, F or a $(C_1$-$C_3)$alkyl group, wherein W may be O or S, preferably wherein W is 0, and preferably Y is $Y_A$ or $Y_B$ and wherein $R^6$, $R^7$, and $R^8$ are each independently $(C_1$-$C_3)$alkyl groups, more preferably wherein $R^6$, $R^7$, and $R^8$ are all methyl groups and wherein W is O,
wherein B is a ligand which binds to a target protein or polypeptide which is to be degraded by ubiquitin ligase and is linked to A though a —C-linkage to the L group, and preferably wherein B is a chemical moiety which selectively induces degradation of the BRD4 protein within the bromo- and Extra-terminal (BET) family of proteins, and especially wherein B is independently selected from: JQ1; -I-BET 726; I-BET 762 or a pharmaceutically acceptable salt, enantiomer, stereoisomer, hydrate, solvate, or polymorph thereof.

The present invention provides compounds having the structure A-L-B wherein A is an E3 ubiquitin ligase protein binding ligand compound of formula I, and L is a linker in accordance with any of the aspects as detailed above, wherein A has the general formula IA and the $R^1$ to $R^5$, X, Y, L and B groups are as defined hereinbefore wherein IA is:

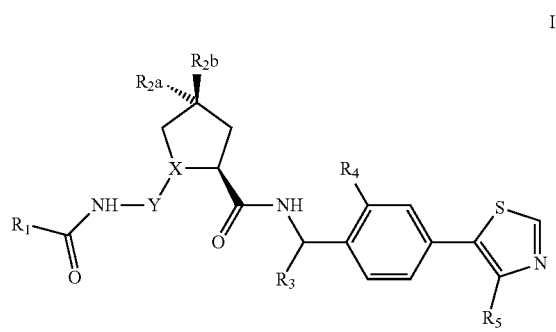

IA

The present invention provides PROTAC compounds having the structure A-L-B wherein A is an E3 ubiquitin ligase protein binding ligand compound of formula I, and L is a linker in accordance with any of the aspects as detailed above, wherein A has the general formula IA, wherein $R^1$ to $R^5$, X, L and B are as defined hereinbefore and wherein Y is $Y_A$, $Y_B$, or $Y_C$ as defined herein before.

The present invention provides PROTAC compounds having the structure A-L-B wherein A is an E3 ubiquitin ligase protein binding ligand compound of formula I, L is a linker in accordance with any of the aspects as detailed hereinbefore, wherein B is as defined in accordance with any of the aspects as detailed hereinbefore, and preferably wherein A has the general formula IA, wherein $R^1$ to $R^5$, X, Y, L and B are as defined hereinbefore, preferably wherein Y is

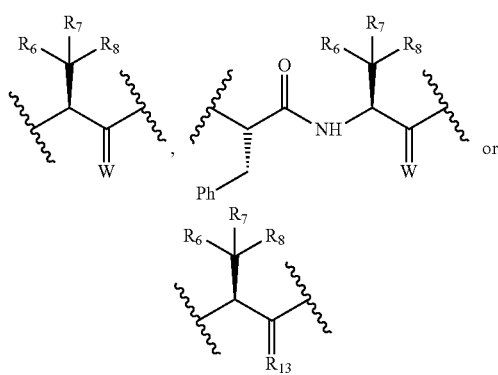

wherein $R^6$, $R^7$, $R^8$ and $R^{13}$ are as defined herein before wherein W may be O or S,
wherein L is a —(CH$_2$CH$_2$O)$_b$— group which is directly bonded to the compound of formula IA at a position independently selected from: $R^1$; $R^3$; $R^4$; $R^5$; or $R^8$, wherein X is C or N, wherein b is 1 to 10, preferably 1 to 6, more preferably 1 to 4, and particularly 2, 3 or 4.

PROTAC compounds having the structure A-L-B wherein A is an E3 ubiquitin ligase protein binding ligand compound of formula I, preferably of formula IA, wherein L and B are in accordance with any of the aspects as detailed above, particularly wherein L is a PEG1 to PEG 4 groups and wherein B is independently selected from: JQ1; -I-BET 726; I-BET 762, and wherein the L-group is directly bonded to the compound of Formula I or IA at the $R^1$ position are as defined hereinbefore and are as detailed hereinafter.

In addition, exemplary PROTAC compounds having the structure A-L-B wherein A is an E3 ubiquitin ligase protein binding ligand compound of formula I, preferably of formula IA, wherein L and B are in accordance with any of the aspects as detailed above, and wherein the L-group is directly bonded to the compound of Formula I or IA at the $R^1$, $R^3$, $R^4$, $R^5$ or $R^{8*}$ positions are provided in Groups I to VII as defined hereinafter.

There are also provided herein a group of PROTAC compounds having the structure A-L-B wherein A is an E3 ubiquitin ligase protein binding ligand compound of formula I, and L is a linker in accordance with any of the aspects, or preferred or particular aspects as detailed above, wherein A has the general formula IA, wherein $R^1$ to $R^5$, X, L and B are as defined hereinbefore and wherein Y is $Y_A$, $Y_B$, or $Y_C$, preferably wherein Y is $Y_A$ or $Y_B$ and more preferably wherein Y is $Y_A$ or $Y_B$ and wherein: when Y is $Y_A$ W is O and $R^6$, $R^7$ and $R^8$ are methyl groups; and when Y is $Y_B$ W is O and $R^6$, $R^7$ and $R^8$ are methyl groups.

As used herein, the following terms have the meanings as defined below, unless otherwise noted:

"$C_a$-$C_b$alkyl" on its own or in composite expressions such as $C_a$-$C_b$haloalkyl, etc. represents a straight or branched alkyl radical having the number of carbon atoms designated, e.g. $C_1$-$C_4$alkyl means an alkyl radical having from 1 to 4 carbon atoms. Preferred alkyl radicals for use in the present invention are $C_1$-$C_4$ alkyl, including methyl, ethyl, n-propyl, isopropyl, n-butyl, isobutyl, sec.butyl, and tert.butyl.

"$C_2$-$C_4$alkyne" represents a straight or branched alkyl radical having from 2 to 4 carbon atoms and one carbon-to-carbon triple bond, e.g. ethyne ($C_2H_2$), propyne ($C_3H_4$), and 1-butyne ($C_4H_6$).

The term "Me" means methyl, and "MeO" means methoxy.

The term "$C_e$-$C_f$ cyclic" means a "$C_3$-$C_4$" cycloalkyl" group and represents a cyclic monovalent alkyl radical having the number of carbon atoms indicated, e.g. $C_3$-$C_4$cycloalkyl means a cyclic monovalent alkyl radical having 3 or 4 carbon atoms.

The term "amino" represents the radical —NH$_2$.

The term "halo" represents a halogen radical such as fluoro, chloro, bromo or iodo. Preferred halo group is fluoro.

The term "Ph" means phenyl, for example in $R^{11}$ or $Y_B$ groups herein "Ph" represents the radical —$C_6H_5$.

The term "5 or 6 membered heterocyclic ring" represents a stable saturated monocyclic 5 or 6 membered ring containing 1, 2 or 3 nitrogen heteroatoms.

The term "5 or 6 membered heteroaromatic" or "heteroaryl" represents a stable monocyclic aromatic ring containing 1-3 nitrogen heteroatoms having 5 or 6 ring atoms.

Typical configurations of 5 or 6 membered heterocyclic or heteroaromatic rings for use as L groups herein include: triazole; diazole; pyrazole; pyrrolidine; pyrrroline; pyrrole; pyrazolidine; pyrazoline; pyrazole; piperidine; pyridine; piperazine; pyrazine; pyrimidine; pyrimidazine; triazine4,5-dihydroimidazole. Preferred configurations of 5 or 6 membered heterocyclic or heteroaromatic rings for use as L groups herein are 1,2,3-triazoles, 1,3-diazoles, and piperazines. Exemplary 5 or 6 membered heterocyclic or heteroaromatic rings for use as L groups herein are independently selected from:

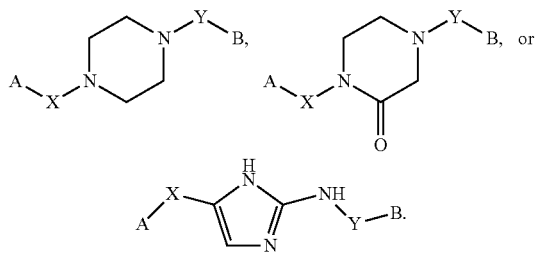

The term "C-linked ($C_3$-$C_4$) oxygen containing heterocyclic group" represents a stable saturated monocyclic 3 or 4 membered ring containing 1 oxygen or 1 nitrogen heteroatom. Typical configurations of 3 or 4 membered heterocyclic rings for use as $R^1$ groups herein include: aziridines; oxiranes; azetidines; and oxetanes. Preferred configurations of 3 or 4 membered heterocyclic rings for use as $R^1$ groups herein are oxiranes and azetidines. Exemplary 3 or 4 membered heterocyclic rings for use as $R^1$ groups herein are independently selected from:

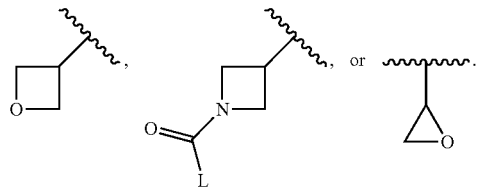

As used herein, the term "=O", i.e. in —C(O)—, forms a carbonyl moiety when attached to a carbon atom. It should be noted that an atom can only carry an oxo group when the valency of that atom so permits.

As used herein, the term, "=C", i.e. in —C(=)—$R^{13}$, denotes an unsaturated carbon-to-carbon double bond.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts suitable for use herein include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange.

Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulphonate.

The PROTAC compounds of the invention can be administered as pharmaceutically acceptable prodrugs which release the compounds of the invention in vivo. "Prodrug", as used herein means a compound which is convertible in vivo by metabolic means (e.g. by hydrolysis) to afford any compound delineated by the formulae of the instant invention. Various forms of prodrugs are known in the art, for example, as discussed in "Design and Application of Prodrugs, Textbook of Drug Design and Development, Chapter 5, 113-191 (1991); Bundgaard, et al., Journal of Drug Deliver Reviews, 8:1-38(1992); and Bernard Testa and Joachim Mayer, "Hydrolysis In Drug and Prodrug Metabolism—Chemistry, Biochemistry and Enzymology," John Wiley and Sons, Ltd. (2003).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Related terms, are to be interpreted accordingly in line with the definitions provided above and the common usage in the technical field.

The present invention also includes isotope-labelled PROTAC compounds of structure A-L-B, as well as compounds of formula I or any subgroup of formula I, wherein one or more of the atoms is replaced by an isotope of that atom, i.e. an atom having the same atomic number as, but an atomic mass different from, the one(s) typically found in nature. Examples of isotopes that may be incorporated into the PROTAC compounds of structure A-L-B, compounds of formula I, or any subgroup of formula I, include but are not limited to isotopes of hydrogen, such as $^2H$ and $^3H$ (also denoted D for deuterium and T for tritium, respectively), carbon, such as $^{11}C$, $^{13}C$ and $^{14}C$, nitrogen, such as $^{13}N$ and $^{15}N$, oxygen, such as $^{15}O$, $^{17}O$ and $^{18}O$, phosphorus, such as $^{31}P$ and $^{32}P$, sulphur, such as $^{35}S$, fluorine, such as $^{18}F$, chlorine, such as $^{36}Cl$, bromine such as $^{75}Br$, $^{76}Br$, $^{77}Br$ and $^{82}Br$, and iodine, such as $^{123}I$, $^{124}I$, $^{125}I$ and $^{131}I$. The choice of isotope included in an isotope-labelled compound will depend on the specific application of that compound. For example, for drug or substrate tissue distribution assays, compounds wherein a radioactive isotope such as $^3H$ or $^{14}C$ is incorporated will generally be most useful. For radio-imaging applications, for example positron emission tomography (PET) a positron emitting isotope such as $^{11}C$, $^{18}F$, $^{13}N$ or $^{15}O$ will be useful. The incorporation of a heavier isotope, such as deuterium, i.e. $^2H$, may provide greater metabolic stability to a PROTAC compound of structure A-L-B, a compound of formula I, or any subgroup of formula I, which may result in, for example, an increased in vivo half-life of the compound or reduced dosage requirements.

Isotope-labelled PROTAC compounds of structure A-L-B, compounds of formula I, or any subgroup of formula I can be prepared by processes analogous to those described in the Schemes and/or Examples herein below by using the appropriate isotope-labelled reagent or starting material instead of the corresponding non-isotope-labelled reagent or starting material, or by conventional techniques known to those skilled in the art.

In a preferred aspect herein the compounds of formula I for use in the PROTAC compounds of structure A-L-B— as defined herein are represented as a defined stereoisomer. The absolute configuration of such compounds can be determined using art-known methods such as, for example, X-ray diffraction or NMR and/or implication from starting materials of known stereochemistry.

Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers which are substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates as detailed herein may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo-specifically. Preferably, if a specific stereoisomer is desired, said compound is synthesized by stereospecific methods of preparation. These methods will advantageously employ enantiomerically pure starting materials.

The diastereomeric racemates of the compounds of formula I for use in the PROTAC compounds of structure A-L-B as defined herein can be obtained separately by conventional methods. Appropriate physical separation methods that may advantageously be employed are, for example, selective crystallization and chromatography, e.g. column chromatography.

The present invention provides PROTAC compounds having the structure A-L-B wherein A is an E3 ubiquitin ligase protein binding ligand compound of formula I or IA, and L is a linker in accordance with any of the aspects as detailed above, wherein B is a chemical moiety which selectively induces degradation of the BRD4 protein within the bromo- and Extra-terminal (BET) family of proteins, and optionally wherein B is independently selected from: JQ1; -I-BET 726; I-BET 762.

The present invention provides PROTAC compounds of structure A-L-B wherein B is a chemical moiety which binds to a protein within the bromo- and Extra-terminal (BET) family of proteins, preferably PROTAC compounds of structure A-L-B wherein B is a chemical moiety which binds to a protein within the bromo- and Extra-terminal (BET) family of proteins independently selected from: BRD2, BRD3 and BRD4, and particularly PROTAC compounds of structure A-L-B wherein B is a chemical moiety which selectively induces degradation of the BRD4 protein within the bromo- and Extra-terminal (BET) family of proteins.

In a further aspect, the invention provides a PROTAC compound of structure A-L-B as defined herein for use as a medicament.

The term "subject" as used herein refers to a mammal. A subject therefore refers to, for example, dogs, cats, horses, cows, pigs, guinea pigs, and the like. Preferably the subject is a human. When the subject is a human, the subject may also be referred to herein as a patient.

"Treat", "treating" and "treatment" refer to a method of alleviating or abating a disease and/or its attendant symptoms.

The term "therapeutically effective amount" means an amount effective to treat, cure or ameliorate a disease, condition illness or sickness.

A further aspect of the invention provides a method for the prophylaxis or treatment of a disease or condition associated with deregulation of protein activity of one or more proteins within the the Bromo- and Extra-terminal (BET) family of proteins BRD2, BRD3 and BRD4 comprising the administration of a PROTAC compound of structure A-L-B to a subject suffering from or likely to be exposed to said disease or condition. A related aspect of the invention provides the use of a PROTAC compound of structure A-L-B in the treatment or prophylaxis of a disease or condition associated with deregulation of BET protein activity. A further related aspect provides the use of a PROTAC compound of structure A-L-B as defined herein for the treatment or prophylaxis of a disease or condition associated with deregulation of BET protein activity.

A further aspect of the invention provides a method for the prophylaxis or treatment of a disease or condition associated with deregulation of protein activity of one or more proteins within the the Bromo- and Extra-terminal (BET) family of proteins BRD2, BRD3 and BRD4 comprising the administration of a therapeutically effective amount of a PROTAC compound of structure A-L-B to a subject suffering from or likely to be exposed to said disease or condition. A related aspect of the invention provides the use of a therapeutically effective amount of a PROTAC compound of structure A-L-Bin the treatment or prophylaxis of a disease or condition associated with deregulation of BET protein activity. A further related aspect provides the use of a therapeutically effective amount of a PROTAC compound of structure A-L-B as defined herein for the treatment or prophylaxis of a disease or condition associated with deregulation of BET protein activity.

A further aspect of the invention provides a method for the prophylaxis or treatment of a disease or condition associated with selective degradation of the BRD4 protein within the bromodomain of the BET family of proteins comprising the administration of a PROTAC compound of structure A-L-B as defined herein to a subject suffering from or likely to be exposed to said disease or condition. A related aspect of the invention provides the use of a PROTAC compound of structure A-L-Bin the treatment or prophylaxis of a disease or condition associated with selective degradation of the BRD4 protein within the bromodomain of the BET family of proteins. A further related aspect provides the use of a PROTAC compound of structure A-L-B for the treatment or prophylaxis of a disease or condition associated with selective degradation of the BRD4 protein within the bromodomain of the BET family of proteins.

Diseases or conditions associated with deregulation of protein activity of one or more proteins within the the Bromo- and Extra-terminal (BET) family of proteins BRD2, BRD3 and BRD4 which may be treated via the administration of a PROTAC compound of structure A-L-B as defined herein include: cancer; benign proliferative disorders; infectious or non-infectious inflammatory events; autoimmune diseases; inflammatory diseases; systemic inflammatory response syndromes; viral infections and diseases; and opthamological conditions.

The present invention also provides PROTAC compounds structure A-L-B wherein B is a chemical moiety which binds to a protein within the bromo- and Extra-terminal (BET) family of proteins, and wherein A is a compound of formula I or formula IA in accordance with any aspect, or preferred aspect detailed herein for use in medicine, particularly for use in conditions or diseases where binding to a protein within the bromo- and Extra-terminal (BET) family of proteins independently selected from: BRD2, BRD3 and BRD4 is implicated, and especially for use in the treatment of one or more conditions or diseases independently selected from: cancer; benign proliferative disorders; infectious or non-infectious inflammatory events; autoimmune diseases; inflammatory diseases; systemic inflammatory response syndromes; viral infections and diseases; and opthamological conditions.

There is also provided herein PROTAC compounds of formula A-L-B in accordance with any aspect herein, for use in the treatment of cancer and a method of treatment of cancer by administration of an effective amount of a PROTAC compound of formula A-L-B in accordance with any aspect herein, to a mammal, in particular a human in need of such treatment.

Cancer-types which may be treated via the administration of a PROTAC compound of structure A-L-B as defined herein include: carcinoma-type cancers associated with epithelial cells disorders such as for example breast cancer, prostate cancer, lung cancer pancreatic cancer and cancer of the colon; sarcoma-type cancers associated with mesenchymal cell disorders; lymphoma; leukemia, such as for example acute myeloid leukaemia; cancers and/or cancerous tumours associated with pluripotent cells such as testicular cancer and ovarian carcinoma.

Examples of cancers that the compounds of the present invention may be used in the treatment of include: adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, Wilms' tumor, hematological cancers (such as leukaemia), epithelial cancers including lung, breast and colon carcinomas, midline carcinomas, mesenchymal, hepatic, renal and neurological tumours. Thus Examples of benign proliferative disorders that the compounds of the present invention may be used in the treatment of include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

There is also provided herein PROTAC compounds of formula A-L-B in accordance with any aspect herein, for use in the treatment of infectious and non-infectious inflammatory events and autoimmune and other inflammatory diseases, disorders and syndromes and a method of treatment of infectious and non-infectious inflammatory events and autoimmune and other inflammatory diseases disorders and syndromes by administration of an effective amount of a PROTAC compound of formula A-L-B in accordance with any aspect herein, to a mammal, in particular a human in need of such treatment. Examples of infectious and non-infectious inflammatory events and autoimmune and other inflammatory diseases, disorders and syndromes that the compounds of the present invention may be used in the treatment of include but are not limited to: inflammatory pelvic disease (PID), gout, pleurisy, eczema, splenitis, laryngitis, thyroiditis, prostatitis, pharyngitis, sarcoidosis, seborrheic dermatitis, irritable bowel syndrome (IBS), diverticulitis, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergic reactions, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anaemia, glomerulonephritis, dermatomyositis, multiple sclerosis, some myopathies, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In other embodiments, the present invention provides PROTAC compounds of formula A-L-B in accordance with any aspect herein, for use in the treatment of systemic inflammatory response syndromes, and a method of treatment of systemic inflammatory response syndromes by administration of an effective amount of a PROTAC compound of formula A-L-B in accordance with any aspect herein, to a mammal, in particular a human in need of such treatment. Examples of systemic inflammatory response syndromes that the compounds of the present invention may be used in the treatment of include: LPS-induced endotoxic shock and/or bacteria-induced sepsis.

Autoimmune diseases and Autoimmune-related diseases which may be treated via the administration of a PROTAC compound of structure A-L-B as defined herein include: acute Disseminated Encephalomyelitis (ADEM); acute necrotizing hemorrhagic leukoencephalitis; Addison's disease; agammaglobulinemia; alopecia areata; amyloidosis; ankylosing spondylitis; anti-GBM/anti-TBM nephritis; antiphospholipid syndrome (APS); autoimmune angioedema; autoimmune aplastic anemia; autoimmune dysautonomia; autoimmune hepatitis; autoimmune hyperlipidemia; autoimmune immunodeficiency; autoimmune inner ear disease (AIED); autoimmune myocarditis; autoimmune oophoritis; autoimmune pancreatitis; autoimmune retinopathy; autoimmune thrombocytopenic purpura (ATP); autoimmune thyroid disease; autoimmune urticaria; axonal & neuronal neuropathies; Balo disease; Behcet's disease; bullous pemphigoid; cardiomyopathy; Castleman disease; celiac disease; Chagas disease; chronic fatigue syndrome; chronic inflammatory demyelinating polyneuropathy (CIDP); chronic recurrent multifocal ostomyelitis (CRMO); Churg-Strauss syndrome; cicatricial pemphigoid/benign mucosal pemphigoid; Crohn's disease; Cogans syndrome; cold agglutinin disease; congenital heart block; Coxsackie myocarditis; CREST disease; essential mixed cryoglobulinemia; demyelinating neuropathies; dermatitis herpetiformis; dermatomyositis; Devic's disease (neuromyelitis optica); discoid lupus; Dressler's syndrome; endometriosis; eosinophilic esophagitis; eosinophilic fasciitis; erythema nodosum; experimental allergic encephalomyelitis; Evans syndrome; fibromyalgia; fibrosing alveolitis; giant cell arteritis (temporal arteritis); giant cell myocarditis; glomerulonephritis; Goodpasture's syndrome; granulomatosis with polyangiitis (GPA) (formerly called Wegener's Granulomatosis); Graves' disease; Guillain-Barre syndrome; Hashimoto's encephalitis; Hashimoto's thyroiditis; hemolytic anemia; Henoch-Schonlein purpura; herpes gestationis; hypogammaglobulinemia; idiopathic thrombocytopenic purpura (ITP); IgA nephropathy; IgG4-related sclerosing disease; immunoregulatory lipoproteins; inclusion body myositis; interstitial cystitis; juvenile arthritis; juvenile diabetes (Type 1 diabetes); juvenile myositis; Kawasaki syndrome; Lambert-Eaton syndrome; leukocytoclastic vasculitis; lichen planus; lichen sclerosus; ligneous conjunctivitis; linear IgA disease (LAD); lupus (SLE); Lyme disease; Meniere's disease; microscopic polyangitis; mixed connective tissue disease (MCTD); Mooren's ulcer; Mucha-Habermann disease; multiple sclerosis; myasthenia gravis; myositis; narcolepsy; neuromyelitis optica (Devic's disease); neutropenia; ocular cicatricial pemphigoid; optic neuritis; palindromic rheumatism; PANDAS (Pediatric Autoimmune Neuropsychiatric Disorders Associated with *Streptococcus*); paraneoplastic cerebellar degeneration; paroxysmal nocturnal hemoglobinuria (PNH); Parry Romberg syndrome; Parsonnage-Turner syndrome; pars planitis (peripheral uveitis); pemphigus; peripheral neuropathy; perivenous encephalomyelitis; pernicious anemia; POEMS syndrome; polyarteritis *nodosa*; type I, II, & III autoimmune polyglandular syndromes; polymyalgia rheumatica; polymyositis; postmyocardial infarction syndrome; postpericardiotomy syndrome; progesterone dermatitis; primary biliary cirrhosis; primary sclerosing cholangitis; psoriasis; psoriatic arthritis; idiopathic pulmonary fibrosis; pyoderma gangrenosum; pure red cell aplasia; Raynauds phenomenon; reactive arthritis; reflex sympathetic dystrophy; Reiter's syndrome; relapsing polychondritis; restless legs syndrome; retroperitoneal fibrosis; rheumatic fever; rheumatoid arthritis; sarcoidosis; Schmidt syndrome; scleritis; scleroderma; Sjogren's syndrome; sperm & testicular autoimmunity; stiff person syndrome; subacute bacterial endocarditis (SBE); Susac's syndrome; sympathetic ophthalmia; Takayasu's arteritis; temporal arteritis/giant cell arteritis; thrombocytopenic purpura (TTP); Tolosa-Hunt syndrome; transverse myelitis; type 1 diabetes; ulcerative colitis; undifferentiated connective tissue disease (UCTD); uveitis; vasculitis; vesiculobullous dermatosis; vitiligo; Wegener's granulomatosis (now termed Granulomatosis with Polyangiitis (GPA).

As will be readily appreciated by the skilled person there is a certain degree of overlap between conditions and diseases within those defined herein as inflammatory and autoimmune disorders or conditions, which is to be expected in view of the complex nature of such conditions and the presentations of each individual subject.

There is additionally provided herein PROTAC compounds of formula A-L-B in accordance with any aspect herein, for use in the treatment of viral infections and diseases, and a method of treatment of viral infections and diseases by administration of an effective amount of a PROTAC compound of formula A-L-B in accordance with any aspect herein, to a mammal, in particular a human in need of such treatment. Examples of viral infections and diseases that the compounds of the present invention may be used in the treatment of include: episome-based DNA viruses including, but not limited to, human papillomavirus, Herpesvirus, Epstein-Barr virus, human immunodeficiency virus, hepatis B virus, and hepatiis C virus.

There is also provided herein PROTAC compounds of formula A-L-B in accordance with any aspect herein, for use in the treatment of viral infections and a method of treatment of viral infections by administration of an effective amount of a PROTAC compound of formula A-L-B in accordance with any aspect herein, to a mammal, in particular a human in need of such treatment. Examples of viral infections that the compounds of the present invention may be used in the treatment of include herpes virus, human papilloma virus, adenovirus, poxyirus and other DNA viruses.

There is also provided herein PROTAC compounds of formula A-L-B in accordance with any aspect herein, for use in the treatment of ophthamological indications and a method of treatment of ophthamological indications by administration of an effective amount of a PROTAC compound of formula A-L-B in accordance with any aspect herein, to a mammal, in particular a human in need of such treatment. Examples of ophthamological indications that the compounds of the present invention may be used in the treatment of include dry eye.

A further aspect of the invention provides a method for the prophylaxis or treatment of a disease or condition associated with deregulation of BET protein activity comprising the administration of a PROTAC compound of structure A-L-B as defined herein to a subject suffering from or likely to be exposed to said disease or condition wherein said disease or condition is independently selected from: cancer; benign proliferative disorders; infectious or non-infectious inflammatory events; autoimmune diseases; inflammatory diseases; systemic inflammatory response syndromes; viral infections and diseases; and opthamological conditions. A related aspect of the invention provides the use of a PROTAC compound of structure A-L-B as defined herein in the treatment or prophylaxis of a disease or condition associated with deregulation of BET protein activity wherein said disease or condition is independently selected from: cancer; benign proliferative disorders; infectious or non-infectious inflammatory events; autoimmune diseases; inflammatory diseases; systemic inflammatory response syndromes; viral infections and diseases; and opthamological conditions. A further related aspect provides the use of a PROTAC compound of structure A-L-B as defined herein for the treatment or prophylaxis of a disease or condition associated with deregulation of BET protein activity wherein said disease or condition is independently selected from: cancer; benign proliferative disorders; infectious or non-infectious inflammatory events; autoimmune diseases; inflammatory diseases; systemic inflammatory response syndromes; viral infections and diseases; and opthamological conditions.

There is also provided herein PROTAC compounds of formula A-L-B in accordance with any aspect herein, for use in the treatment of disease or condition for which a bromodomain inhibitor is indicated and a method of treatment of disease or condition for which a bromodomain inhibitor is indicated by administration of an effective amount of a PROTAC compound of formula A-L-B in accordance with any aspect herein, to a mammal, in particular a human in need of such treatment. Examples of disease or condition for which a bromodomain inhibitor is indicated that the compounds of the present invention may be used in the treatment of include diseases associated with systemic inflammatory response syndrome, such as sepsis, burns, pancreatitis, major trauma, haemorrhage and ischaemia.

In such uses or methods the PROTAC compound of structure A-L-B would preferably be administered to a subject in need of such treatment at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality.

Alternatively in other circumstances where there is a perceived high risk of sepsis, haemorrhage, extensive tissue damage, SIRS or MODS, the PROTAC compound of structure A-L-B would preferably be administered to a subject in need of such protection from such risks, for example prior to surgical or other procedures associated with a high risk of sepsis, haemorrhage, extensive tissue damage, SIRS or MODS.

According to a particular embodiment there is provided herein use of a PROTAC compounds of structure A-L-B for use in the treatment of sepsis, sepsis syndrome, septic shock and/or endotoxaemia.

According to another embodiment there is provided herein use of a PROTAC compounds of structure A-L-B for use in the treatment of the treatment of acute or chronic pancreatitis, or burns.

Further examples of diseases or conditions for which a bromodomain inhibitor is indicated and for which the PROTAC compounds of structure A-L-B may be used in the treatment of include herpes simplex infections and reactivations, cold sores, herpes zoster infections and reactivations, chickenpox, shingles, human papilloma virus, cervical neoplasia, adenovirus infections, including acute respiratory disease, and poxyirus infections such as cowpox and smallpox and African swine fever virus.

According to further embodiment there is provided herein use of a PROTAC compounds of structure A-L-B for use in the treatment of the treatment of Human papilloma virus infections of skin or cervical epithelia.

In a further aspect there is provided herein, a PROTAC compound of formula A-L-B for use in the treatment of any of the diseases or conditions indicated hereinbefore wherein said treatment modulates one or more of protein methylation, gene expression, cell proliferation, cell differentiation and/or apoptosis in vivo in the disease or condition being treated.

According to a further aspect there is provided a PROTAC compound of formula A-L-B for use in the modulation of one or more one or more of protein methylation, gene expression, cell proliferation, cell differentiation and/or apoptosis in vivo in the treatment of a disease or condition independently selected from: cancer; inflammatory disease; and/or viral disease.

According to another aspect there is provided a therapeutic method of modulating one or more of protein methylation, gene expression, cell proliferation, cell differentiation and/or apoptosis in vivo in the treatment of cancer, inflammatory disease and/or viral disease wherein said method is provided by administering a therapeutically effective amount of one or more PROTAC compounds of structure A-L-B to a subject in need of such therapy.

As demonstrated hereinafter, PROTAC compounds of the invention trigger the intracellular destruction of BET proteins.

As also demonstrated herein PROTAC compounds of structure A-L-B, such as for example, compound MZ1, potently and rapidly induce reversible, long-lasting and unexpectedly selective removal of BRD4 over BRD2 and BRD3. In addition, gene expression profiles of selected cancer-related genes responsive to JQ1 have shown distinct and more limited transcriptional responses induced by a compound of formula I, MZ1. This is consistent with selective suppression of BRD4.

Thus the invention provides PROTAC compounds of formula 1 which bind to a protein within the bromo- and Extra-terminal (BET) family of proteins. The invention additionally provides PROTAC compounds of structure A-L-B, wherein L is as defined hereinbefore, wherein A is a compound of formula I or formula IA as defined hereinbefore and wherein B is a chemical moiety which binds to a protein within the bromo- and Extra-terminal (BET) family of proteins, and wherein said protein is independently selected from: BRD2, BRD3 and BRD4. The invention particularly provides PROTAC compounds of structure A-L-B, wherein L is as defined hereinbefore, wherein A is a compound of formula I or formula IA as defined hereinbefore and wherein B is a chemical moiety which selectively induces degradation of the BRD4 protein within the bromo- and Extra-terminal (BET) family of proteins.

As previously indicated to achieve intracellular BET-protein degradation the Applicant has utilized a small molecule PROTAC (PROteolysis TArgeting Chimera) approach. A PROTAC compound is a hetero-bi-functional compound that contains two ligands connected by a linker unit. In the PROTAC compounds, or PROTACs, according to the present invention one ligand (A), a compound of formula I, or IA as defined herein, binds to an E3 ubiquitin ligase protein and the other ligand (B) binds to the target protein of interest, thereby bringing the ligase and the target into close proximity.

Whilst not wishing to be bound to any particular theory it is proposed herein that it is this close proximity which in turn triggers the poly-ubiquitination and subsequent proteasome-dependent degradation of the target protein of interest. Supporting evidence for a PROTAC approach on a general level is provided by known proof-of-concept examples where alternative PROTACs have been used to degrade: the Estrogen-receptor, Cyrus, K., Wehenkel, M., Choi, E. Y., Swanson, H. & Kim, K. B., "*Two-headed PROTAC: An effective new tool for targeted protein degradation*". ChemBioChem, 11, 1531-1534 (2010); the Androgen-receptor, Sakamoto, K. M. et al., "*Development of Protacs to target cancer-promoting proteins for ubiquitination and degradation*". Mol. Cell. Proteomics 2, 1350-8 (2003); methionine aminopeptidease-2, Sakamoto, K. M. et al., "*Protacs: chimeric molecules that target proteins to the Skp1-Cullin-F box complex for ubiquitination and degradation*"., Proc. Natl. Acad. Sci. U.S.A, 98, 8554-9 (2001); as well as the Aryl Hydrocarbon Receptor, Lee, H., Puppala, D., Choi, E. Y., Swanson, H. & Kim, K. B., "*Targeted degradation of the aryl hydrocarbon receptor by the PROTAC approach: A useful chemical genetic tool*.", ChemBioChem 8, 2058-2062, (2007).

To date, all first-generation PROTACs include a peptidic moiety as the E3 ligase ligand. For example, a hydroxyproline-containing heptapeptide sequence ALA-Hyp-YIP from the transcription factor Hypoxia-Inducible Factor 1 alpha subunit (HIF-1α) has been widely used, and as described by Schneekloth, J. S., et al., in "*Chemical Genetic Control of Protein Levels: Selective in Vivo Targeted Degradation*." J. Am. Chem. Soc., 126, 3748-3754 (2004), as this represents the minimal epitope for HIF-1α binding to the E3 ligase von Hippel Lindau protein (VHL), as confirmed by Hon, W.-C. et al., in "*Structural basis for the recognition of hydroxyproline in HIF-1 alpha by pVHL*"., Nature, 417, 975-8 (2002).

The Applicant has recognized that the high peptidic nature of these first-generation PROTACs has resulted in poor physicochemical properties such as low intracellular stability and poor cell permeability, which has limited their applicability as chemical probes as well as their potential utility in therapeutic development.

To overcome these limitations the Applicant has developed novel PROTACs including small molecules of formula I, for use in the present, non-peptidic PROTAC approach. In a particular aspect this approach exploits novel optimized small molecule drug-like ligands (A) of formula I, in PROTAC compounds of structure A-L-B and demonstrates that these can be applied to target BET bromodomains and potently induce effective and selective degradation of BRD4.

According an aspect the present invention provides PROTAC compounds having the structure A-L-B as defined hereinbefore, wherein B is present and wherein B is a ligand which binds to a target protein or polypeptide which is to be degraded by ubiquitin ligase, and wherein said target protein is selected from the group consisting of structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity and translation regulator activity.

According an aspect the present invention provides PROTAC compounds having the structure A-L-B as defined hereinbefore, wherein B is present and wherein B is a ligand which binds to a target protein or polypeptide which is to be degraded by ubiquitin ligase, and wherein said target protein is selected from the group consisting of B7.1 and B7, TIFR1m, TNFR2, NADPH oxidase, BcllBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD 124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus, 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, and chloride channels; acetyl-CoA carboxylase, adenylosuccinate synthetase, protoporphyrinogen oxidase, and enolpyruvylshikimate-phosphate synthase.

According an aspect the present invention provides PROTAC compounds having the structure A-L-B as defined hereinbefore, wherein B is present and wherein B is a ligand which binds to a target protein or polypeptide which is to be degraded by ubiquitin ligase, and wherein B is an Hsp90 inhibitor; a kinase inhibitor, a phosphatase inhibitor, an MDM2 inhibitor, a compound which targets human BET Bromodomain-containing proteins, an HDAC inhibitor, a human lysine methyltransferase inhibitor, a compound targeting RAF receptor, a compound targeting FKBP, an angiogenesis inhibitor, an immunosuppressive compound, a compound targeting an aryl hydrocarbon receptor, a compound targeting an androgen receptor, a compound targeting an estrogen receptor, a compound targeting a thyroid hormone receptor, a compound targeting HIV protease, a compound targeting HIV integrase, a compound targeting HCV protease or a compound targeting acyl protein thioesterase 1 and/or 2.

According an aspect the present invention provides a method of degrading a target protein in a patient in need comprising administering to said patient an effective amount of a PROTAC compound of structure A-L-B as defined herein, or use of said PROTAC for degrading a target protein in a patient by administration of an effective amount thereof.

According an aspect the present invention provides a method of targeting protein in a cell comprising exposing said cell to an effective amount of a PROTAC compound of structure A-L-B as defined herein, or use of said PROTAC for targeting protein in a cell comprising exposing said cell to an effective amount thereof.

General Processes for Preparation of the Present PROTACs

The Applicant has developed a group of PROTACs that have been demonstrated to link together specific VHL ligands and BET bromodomains ligands. Initial work by the Applicant has established that known compounds VHL-1 and VHL-2 are strong binders with $K_d$ values below 300 nM to VHL (FIG. 1a), in Galdeano, C. et al., "*Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities*"., J. Med. Chem. 57, 8657-63 (2014). Inspection of the protein-ligand crystal structures have shown that the methyl group of the terminal acetyl groups in compounds VHL-1 and VHL-2 is solvent exposed and this was selected as a suitable connecting point for a linker (L). This is illustrated in FIG. 5. To confirm that the PROTAC approach provided in the present invention do bind to a target protein, the BET inhibitor JQ1 was chosen as a bromodomain-recruiting scaffold (B) and its t-butyl ester group was selected as a potential_connecting point for a linker (L) because it is solvent-exposed and not involved in key interaction with the BET bromodomains, as shown by the co-crystal structures as illustrated in FIG. 5 and as discussed herein.

Linkers (L) with different lengths comprising of polyethylene glycol chains with either 3 or 4 ethylene glycol units were chosen to connect JQ1 with the VHL ligand in initial proof-of-concept experiments.

To achieve the desired ligands, a generally applicable two-step synthetic strategy was devised. First, the linker bearing a carboxylic acid at one end and an azide group at the other end was connected with the terminal free amine of the VHL ligand by an HATU-mediated amide bond formation. In the second step, reduction of the azide group to an amine and subsequent amide bond formation with the carboxylic acid of the ester-hydrolyzed JQ1 analogue afforded the desired PROTAC compounds MZ1, MZ2, MZ3 and cisMZ1 (FIG. 1b).

Experimental Data for Binding of PROTAC Molecules to Target Proteins

To assess whether PROTAC molecules retained their binding to the target proteins VHL and BET bromodomains in a similar fashion as the parental ligands, isothermal titration calorimetry (ITC) experiments were performed, as discussed hereinafter in relation to FIG. 1c, entries 1-6, and in FIGS. 14 and 15. A compound of structure A-L-B, MZ1, was selected as a representative of all PROTAC molecules that share the same JQ1 moiety for binding bromodomains, was titrated into individual first and second bromodomains of BRD2, BRD3 and BRD4. The measured binding affinities ($K_d$ of 115-380 nM) and ΔH (−6.1 to −10.0 kcal/mol) compared well with those reported in the literature for unmodified JQ1, in Filippakopoulos, P. et al. *"Selective inhibition of BET bromodomains"*., Nature 468, 1067-1073 (2010). The literature values for BRD4 bromodomains are illustrated in FIG. 1c, at entries 7, and 8. This data strongly suggests that the JQ1 binding mode is conserved within the context of PROTACs of the structure A-L-B according to the present invention.

As binding to the VHL protein is crucial for the recruitment of target proteins to the E3 ligase, the binding of PROTAC compounds of structure A-L-B, MZ1 and MZ3 to the VHL-ElonginB-ElonginC complex (VBC) was also quantified using ITC. The data from these experiments is illustrated in FIG. 1c, at entries 9, and 10.

The measured affinities ($K_d$ of 150 and 310 nM for MZ1 and MZ3, respectively) and ΔH (−6.9 and −4.9 kcal/mol, for MZ1 and MZ3, respectively) compared very closely to those reported in the literature for the parental unmodified ligands VHL-1 ($K_d$=185 nM, ΔH=−5.5 kcal/mol, entry 11) and VHL-2 ($K_d$=290 nM, ΔH=−5.3 kcal/mol).

The Applicant has found that in a group of PROTAC compounds of structure A-L-B wherein X is N, and the central R-group (the $R^{2a}$ group at the C-4 position) on the ring is a hydroxyl group in compounds of formula I, then the stereochemistry of the-hydroxyl group of the central hydroxyproline moiety is crucial for ligand binding to VHL. This was confirmed by synthesis of compound cisMZ1. This compound is structurally identical to MZ1 except for a reversed stereo center at the C-4 position bearing the hydroxyl group. The experimental data for cisMZ1 did not exhibit any measurable binding affinity for VHL in an ITC experiment. These experimental results are illustrated in FIG. 1c, at entry 12, and cisMZ1 was thereafter elected as a negative control compound in cellular assays.

Thus the present invention provides a group of PROTAC compounds of structure A-L-B wherein A is a compound of formula IA as defined hereinbefore, wherein X is N, and $R^{2a}$ (the central R-group at the C-4 position) is a hydroxyl group having trans-stereochemistry.

The present invention provides a PROTAC compound of structure A-L-B wherein A is a compound of formula IA, wherein X is N, and $R^{2a}$ (the central R-group at the C-4 position) is a hydroxyl group having trans stereochemistry and wherein said PROTAC compound is independently selected from:

(2S,4R)-1-((S)-2-(tert-butyl)-14-((S)-4-(4-chlorophenyl)-2,3,9-trimethyl-6H-thieno[3,2-f][1,2,4]triazolo[4,3-a][1,4]diazepin-6-yl)-4,13-dioxo-6,9-dioxa-3,12 diazatetradecanoyl)-4-hydroxy-N-(4-(4-methylthiazol-5-yl)benzyl)pyrrolidine-2-carboxamide;

(2S,4R)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide;

(2S,4R)-1-((S)-2-(tert-butyl)-20-((S)-4-(4-chlorophenyl)-2,3,9-trimethyl-6H-thieno[3,2-f][1,2,4]triazolo[4,3-a][1,4]diazepin-6-yl)-4,19-dioxo-6,9,12,15-tetraoxa-3,18-diazaicosanoyl)-4-hydroxy-N-(4-(4-methylthiazol-5-yl)benzyl)pyrrolidine-2-carboxamide;

(2S,4R)-1-((2S,5S)-5-benzyl-2-(tert-butyl)-20-(4-(4-chlorophenyl)-2,3,9-trimethyl-6H-thieno[3,2-f][1,2,4]triazolo[4,3-a][1,4]diazepin-6-yl)-4,7,19-trioxo-9,12,15-trioxa-3,6,18-triazaicosanoyl)-4-hydroxy-N-(4-(4-methylthiazol-5-yl)benzyl)pyrrolidine-2-carboxamide;

(2S,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide;

(2S,4R)-1-((2S)-2-(tert-butyl)-20-(6-(4-chlorophenyl)-8-methoxy-1-methyl-4H-benzo[f][1,2,4]triazolo[4,3-a][1,4]diazepin-4-yl)-4,19-dioxo-6,9,12,15-tetraoxa-3,18-diazaicosanoyl)-4-hydroxy-N-(4-(4-methylthiazol-5-yl)benzyl)pyrrolidine-2-carboxamide;

(2S,4R)-1-((2S)-2-(tert-butyl)-17-(6-(4-chlorophenyl)-8-methoxy-1-methyl-4H-benzo[f][1,2,4]triazolo[4,3-a][1,4]diazepin-4-yl)-4,16-dioxo-6,9,12-trioxa-3,15-diazaheptadecanoyl) -4-hydroxy-N-(4-(4-methylthiazol-5-yl)benzyl)pyrrolidine-2-carboxamide;

(2S,4R)-1-((2S,5S)-5-benzyl-2-(tert-butyl)-20-(6-(4-chlorophenyl)-8-methoxy-1-methyl-4H-benzo[f][1,2,4]triazolo[4,3-a][1,4]diazepin-4-yl)-4,7,19-trioxo-9,12,15-trioxa-3,6,18-triazaicosanoyl) -4-hydroxy-N-(4-(4-methylthiazol-5-yl)benzyl)pyrrolidine-2-carboxamide;

(2S,4R)-1-((S)-1-(4-((2S,4R)-1-acetyl-4-((4-chlorophenyl)amino)-2-methyl-1,2,3,4-tetrahydroquinolin-6-yl)phenyl)-12-(tert-butyl)-1,10-dioxo-5,8-dioxa-2,11-diazatridecan-13-oyl)-4-hydroxy-N-(4-(4-methylthiazol-5-yl)benzyl)pyrrolidine-2-carboxamide;

(2S,4R)-1-((S)-1-(4-((2S,4R)-1-acetyl-4-((4-chlorophenyl)amino)-2-methyl-1,2,3,4-tetrahydroquinolin-6-yl)phenyl)-15-(tert-butyl) -1,13-dioxo-5,8,11-trioxa-2,14-diazahexadecan-16-oyl)-4-hydroxy-N-(4-(4-methylthiazol-5-yl)benzyl)pyrrolidine-2-carboxamide; and (2S,4R)-1-((S)-1-(4-((2S,4R)-1-acetyl-4-((4-chlorophenyl)amino)-2-methyl-1,2,3,4-tetrahydroquinolin-6-yl)phenyl)-18-(tert-butyl) -1,16-dioxo-5,8,11,14-tetraoxa-2,17-diazanonadecan-19-oyl)-4-hydroxy-N-(4-(4-methylthiazol -5-yl)benzyl)pyrrolidine-2-carboxamide;

or a pharmaceutically acceptable salt, enantiomer, stereoisomer, hydrate, solvate, or polymorph thereof.

As discussed hereinbefore there is provided PROTAC compounds having the structure A-L-B wherein A is an E3 ubiquitin ligase protein binding ligand compound of formula I, preferably of formula IA, wherein L and B are in accordance with any of the aspects as detailed hereinbefore, and wherein the L-group is directly bonded to the compound of Formula I or IA at the $R^1$, $R^3$, $R^4$, $R^5$ or $R^8$ positions. Exemplary compounds wherein the L-group is directly bonded to the compound of Formula I or IA at the $R^1$, $R^3$, $R^4$, $R^5$ or $R^8$ positions are provided in Groups I to VIII hereinafter.

The present invention additionally provides a PROTAC compound of structure A-L-B wherein A is a compound of formula IA independently selected from the compounds identified in any of Groups I to VIII, as shown in Tables I to VIII, and wherein L and B are as defined in accordance with any of the aspects hereinbefore.

Group I. Compounds of formula I with linkage to L at the $R^8$ position and $R^8$=—$CH_2$—$R^8$.

TABLE I

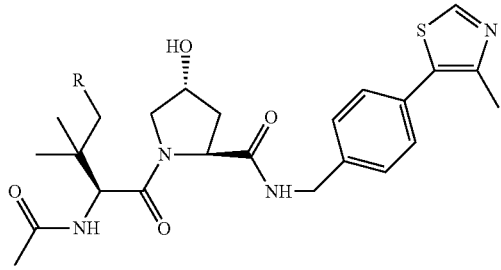

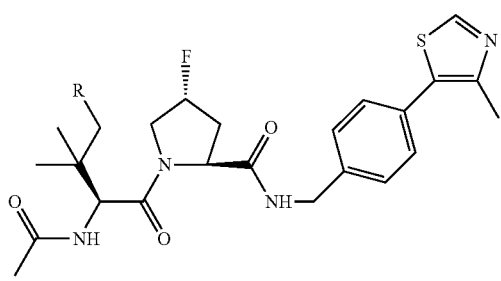

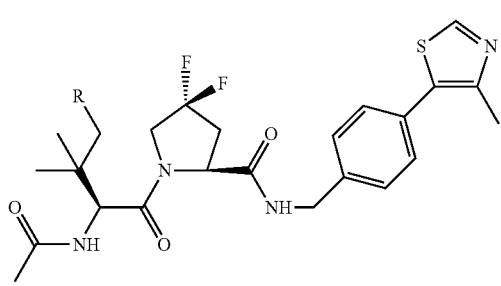

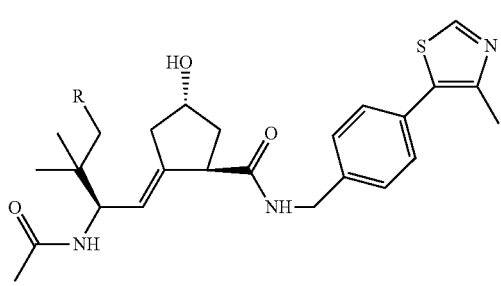

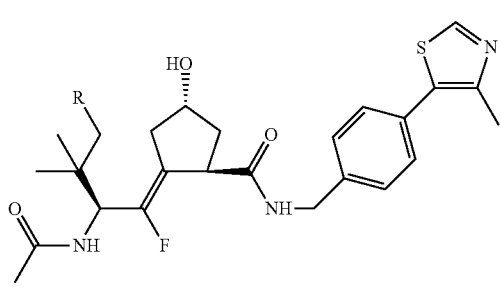

TABLE I-continued

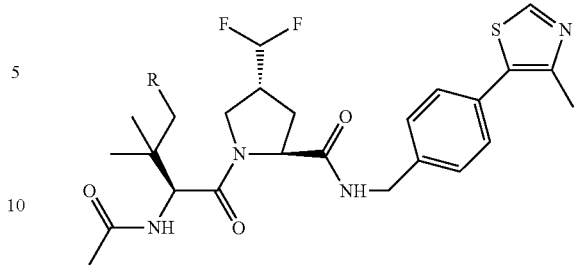

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —$(CH_2CH_2O)_b$— group which is directly bonded to the compound of formula IA at the $R^8$ position, wherein X is N, wherein b is 1 to 10, preferably 1 to 6, more preferably 1 to 4, wherein $R^1$ is a $CH_3$ group wherein said $R^1$ group may be optionally substituted by one or more groups independently selected from: F; CN; or C(O), wherein $R^{2a}$ is OH, F, $NH_2$ or —$CHF_2$, wherein $R^{2b}$ is F, Cl or H, wherein $R^3$ and $R^4$ are both H, wherein $R^5$ is —$CH_3$, wherein Z is $CR^6R^7R^8$, wherein $R^6$ and $R^7$ are both $CH_3$ groups, wherein $R^8$ is a —$(CH_2)_qR$ group wherein q is 1 and wherein $R^8$ is a covalent C-linked bond to L, wherein $R^{11}$ is a covalent bond or a —NHC(O)methylbenzyl-group, wherein $R^{12}$ is —C(O)—, or —C(S)—, and wherein $R^{13}$ is H, F or a —$(C_1$-$C_3)$ alkyl group, wherein the —$(C_1$-$C_3)$ alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —$(CH_2CH_2O)_b$— group which is directly bonded to the compound of formula IA at the $R^8$ position, wherein X is C, wherein b is 1 to 10, preferably 1 to 6, more preferably 1 to 4, wherein $R^1$ is a $CH_3$ group wherein said $R^1$ group may be optionally substituted by one or more groups independently selected from: F; CN; or C(O), wherein $R^{2a}$ is OH, F, $NH_2$ or —$CHF_2$, wherein $R^{2b}$ is F, Cl or H, wherein $R^3$ and $R^4$ are both H, wherein $R^5$ is —$CH_3$, wherein Z is $CR^6R^7R^8$, $R^6$ and $R^7$ are both $CH_3$ groups, wherein $R^8$ is a —$(CH_2)_qR^8$ group wherein q is 1 and wherein $R^{8*}$ is a covalent C-linked bond to L, wherein $R^{11}$ is a covalent bond or a —NHC(O)methylbenzyl- group, wherein $R^{12}$ is —C(O)—, or —C(S)—, and wherein $R^{13}$ is H, F or a —$(C_1$-$C_3)$ alkyl group, wherein the —$(C_1$-$C_3)$ alkyl group is optionally substituted by one or more substituents independently selected from: methyl; OH; or F.

Group IIA. Compounds of formula I with linkage to L at the $R^8$ position and $R^8$=—C(O)—$R^{8*}$.

TABLE IIA

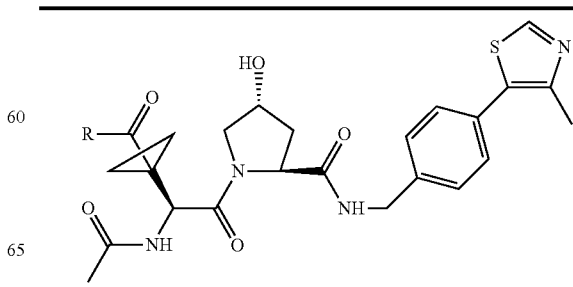

TABLE IIA-continued

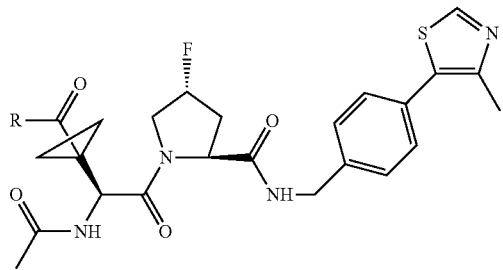

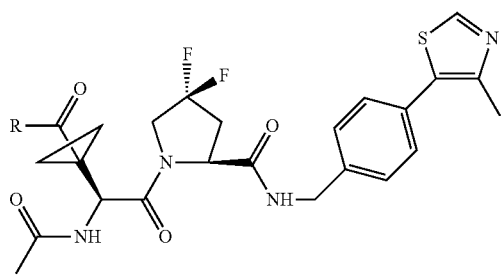

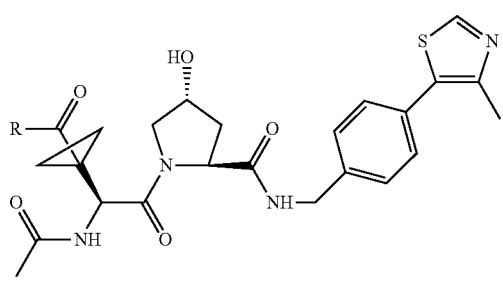

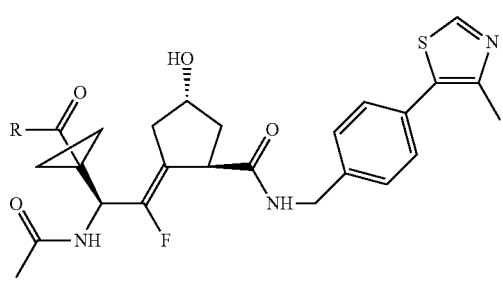

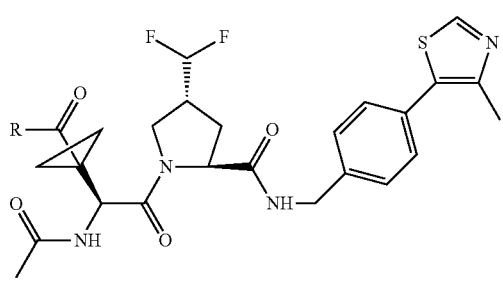

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —(CH$_2$CH$_2$O)$_b$— group which is directly bonded to the compound of formula IA at the $R^8$ position, wherein X is N, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein, $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ form a cyclopropyl alkyl group with the C-atom to which they are attached, wherein $R^8$ is a —C(O)—$R^{8*}$ group wherein $R^{8*}$ is a covalent C-linked bond to L, wherein $R^{11}$ is a covalent bond or a —NHC(O) methylbenzyl- group, wherein $R^{12}$ is —C(O) or —C(S)—, wherein $R^{13}$ is H, F or a —(C$_1$-C$_3$) alkyl group, and wherein the —(C$_1$-C$_3$) alkyl groups or cyclopropyl alkyl groups are is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —(CH$_2$CH$_2$O)$_b$— group which is directly bonded to the compound of formula IA at the $R^8$ position, wherein X is C, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ are both CH$_3$ groups, wherein $R^8$ is a —C(O)—$R^{8*}$ group wherein $R^{8*}$ is a covalent C-linked bond to L, wherein $R^{11}$ is a covalent bond or a —NHC(O) methylbenzyl- group, wherein $R^{12}$ is —C(O) or —C(S)—, wherein $R^{13}$ is H, F or a —(C$_1$-C$_3$) alkyl group, and wherein the —(C$_1$-C$_3$) alkyl or cyclopropyl alkyl groups are optionally substituted by one or more substituents independently selected from: methyl; OH; or F.

Group IIB. Compounds of formula I with linkage to L at the $R^8$ position and $R^8$=—N(H)—$R^{8*}$.

TABLE IIB

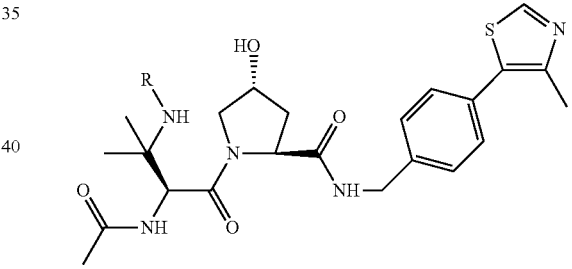

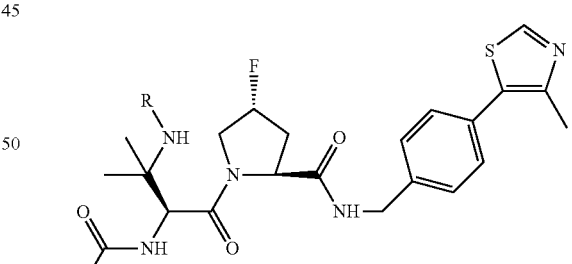

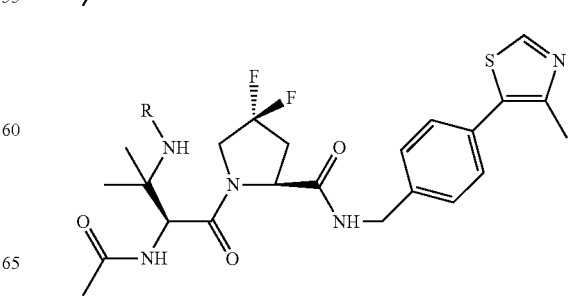

TABLE IIB-continued

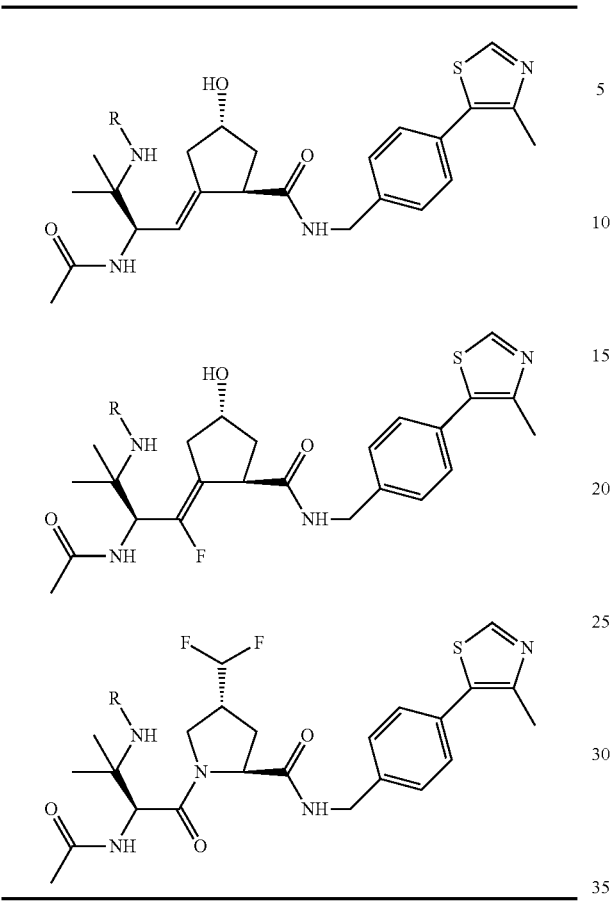

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —(CH$_2$CH$_2$O)$_b$— group which is directly bonded to the compound of formula IA at the $R^8$ position, wherein X is N, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ are both CH$_3$ groups, wherein $R^8$ is a —N(H)R$^{8*}$ group, wherein $R^{8*}$ is a covalent bond which is N-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —(CH$_2$CH$_2$O)$_b$— group which is directly bonded to the compound of formula IA at the $R^8$ position, wherein X is C, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ are both CH$_3$ groups, wherein $R^8$ is a —N(H)R$^{8*}$ group, wherein $R^{8*}$ is a covalent bond, which is N-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Group IIIA. Compounds of formula I with linkage to L at the $R^8$ position and $R^8$ is —C(O)R$^{8*}$.

TABLE IIIA

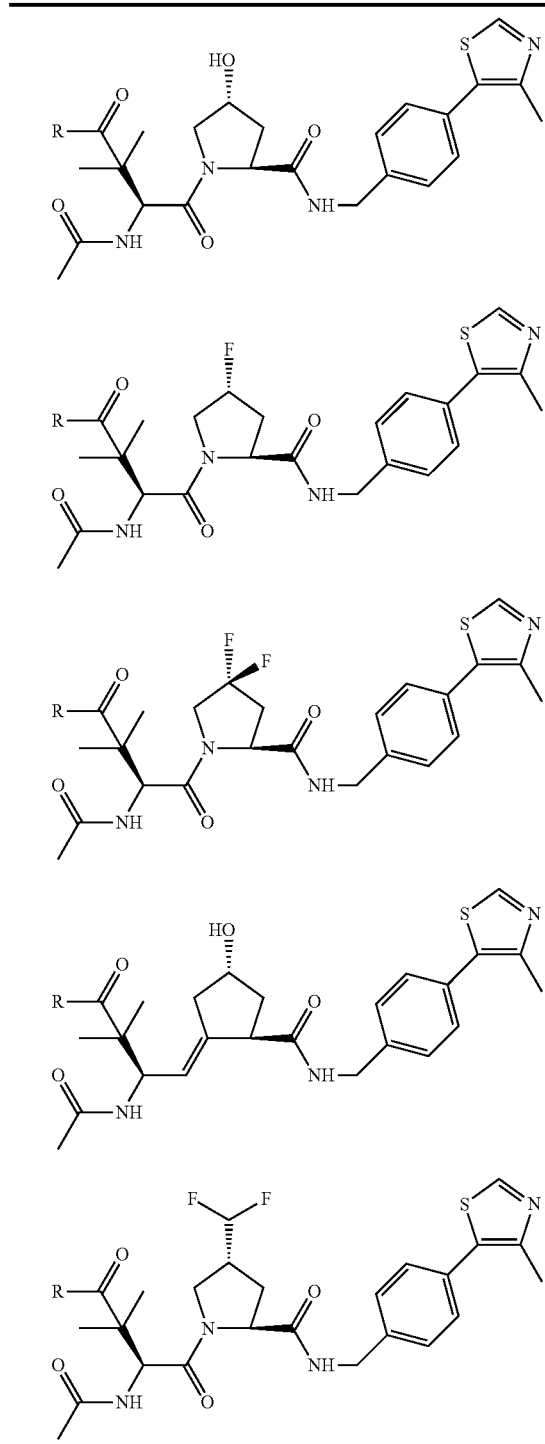

TABLE IIIA-continued

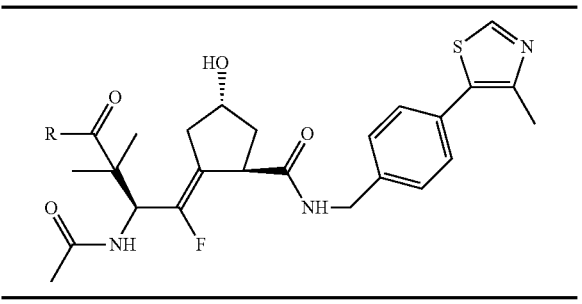

Thus there is also provided herein a compound for Formula IA, wherein Y is $R^{11}$—Z—$R^{12}$, or wherein Y is $Y_A$, $Y_B$ or $Y_C$ are as defined hereinbefore, wherein L is a —(CH$_2$CH$_2$O)$_b$— group which is directly bonded to the compound of formula IA at the $R^8$ position, wherein X is N, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ are both CH$_3$ groups, wherein $R^8$ is a —C(O)R$^{8*}$ group, wherein $R^{8*}$ is a covalent bond which is C-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^8$ position, wherein X is C, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ are both CH$_3$ groups, wherein $R^8$ is a —C(O)R$^{8*}$ group, wherein $R^{8*}$ is a covalent bond which is C-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Group IIIB. Additional compounds of formula I with linkage to L at the $R^8$ position and $R^8$ is (CH$_2$)$_q$R$^{8*}$.

TABLE IIIB

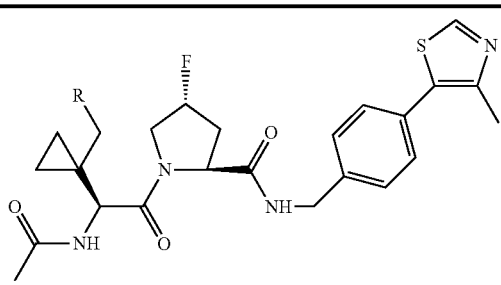

TABLE IIIB-continued

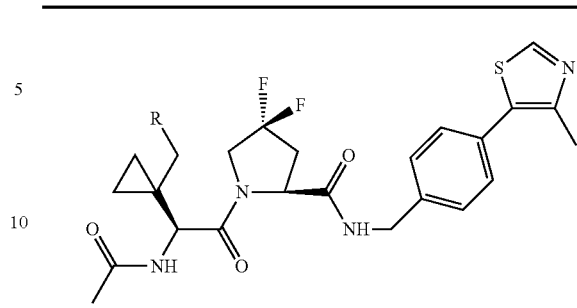

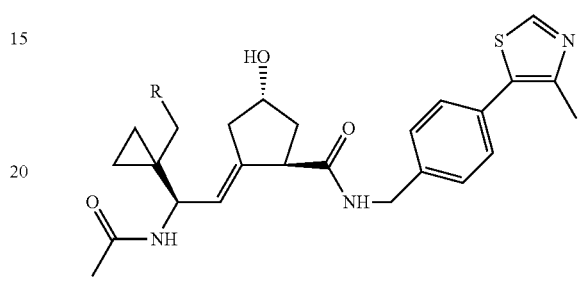

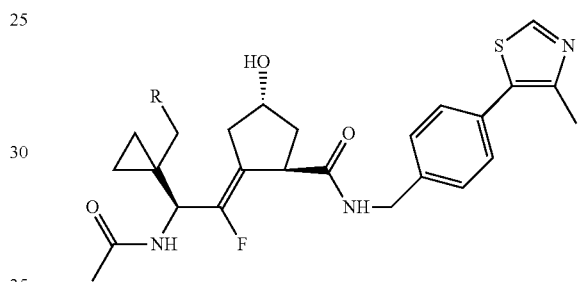

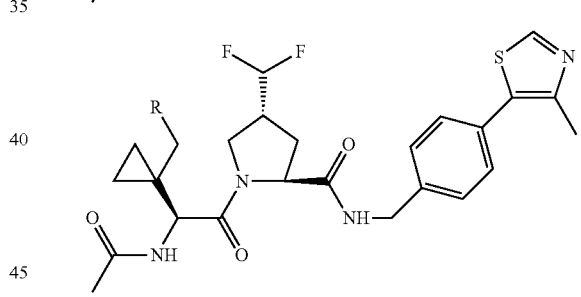

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^8$ position, wherein X is N, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ and the C-atom to which they are attached form a cyclopropyl alkyl group, wherein $R^8$ is a —(CH$_2$)$_q$ R$^{8*}$ group wherein q=1 and wherein $R^{8*}$ is a covalent bond which is C-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, wherein the —(C$_1$-C$_3$) alkyl or cyclopropyl alkyl groups are optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^8$ position, wherein X is C, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ and the C-atom to which they are attached form a cyclopropyl alkyl group, wherein $R^8$ is a —(CH$_2$)$_q$ R$^{8*}$ group wherein q=1 and wherein R$^{8*}$ is a covalent bond which is C-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl or cyclopropyl alkyl groups are optionally substituted by one or more substituents independently selected from: methyl; OH; or F.

Group IIIC. Further compounds of formula I with linkage to L at the R$^{8*}$ position and R$^8$ is —N(H)—R$^{8*}$.

TABLE IIIC

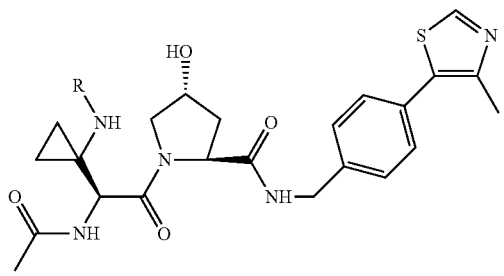

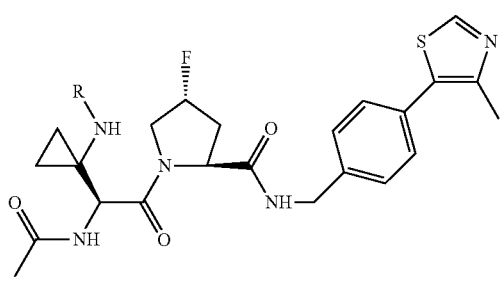

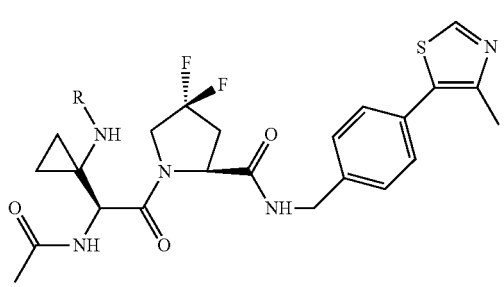

TABLE IIIC-continued

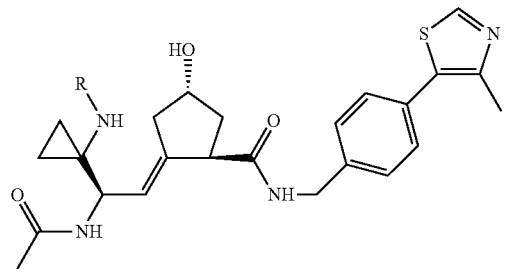

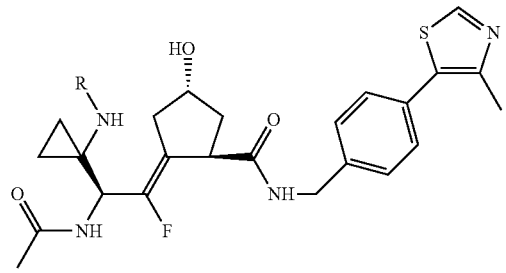

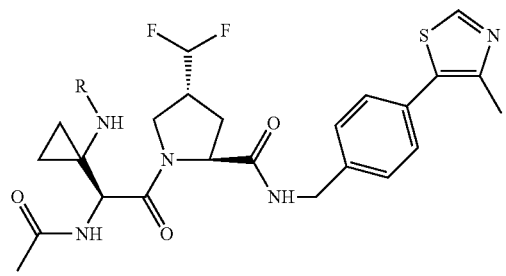

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^8$ position, wherein X is N, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein $R^6$ and $R^7$ and the C-atom to which they are attached form a cyclopropyl alkyl group, wherein $R^8$ is a —N(H)R$^{8*}$ group, wherein R$^{8*}$ is a covalent bond which is N-linked to L, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^8$ position, wherein X is C, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is —CH$_3$, wherein Z is CR$^6$R$^7$R$^8$, wherein R⁶ and R⁷ and the C-atom to which they are attached form a cyclopropyl alkyl group, wherein R⁸ is a —N(H)R⁸* group, wherein R⁸* is a covalent bond which is N-linked to L, wherein R¹¹ is a covalent bond or a —NHC(O)methylbenzyl- group, wherein R¹² is —C(O) or —C(S), wherein R¹³ is H, F or a —(C₁-C₃) alkyl group, and wherein the —(C₁-C₃) alkyl group is optionally substituted by one or more substituents independently selected from: methyl; OH; or F.

Group IV. Compounds of formula I with linkage to L at the R⁴ position.

TABLE IV

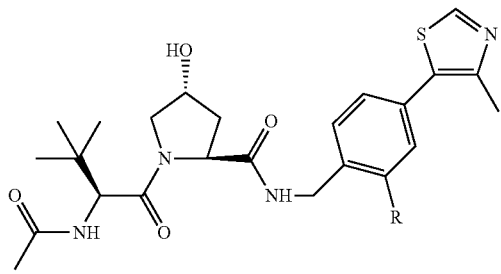

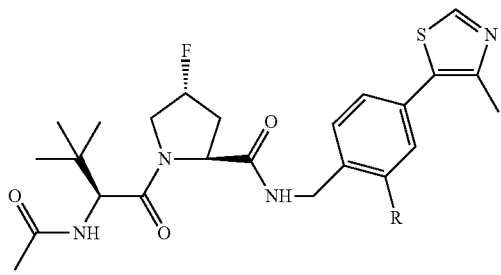

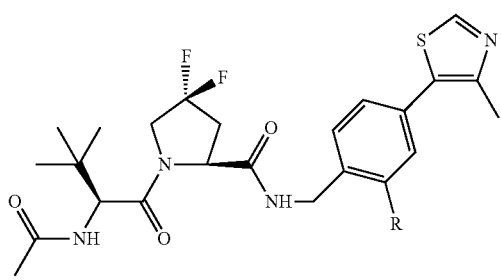

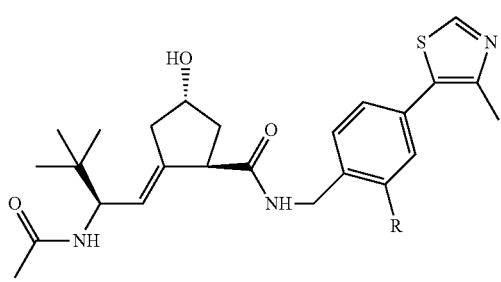

TABLE IV-continued

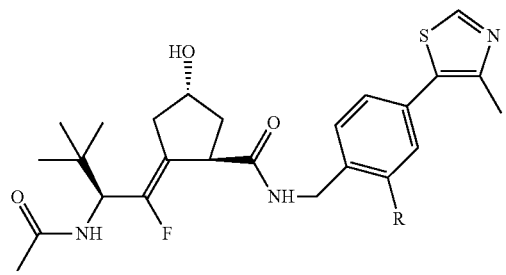

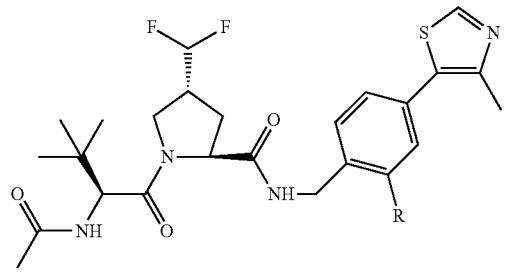

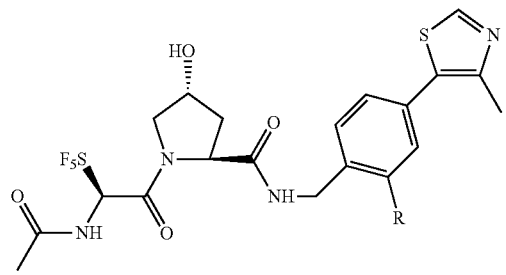

Thus there is also provided herein a compound for Formula IA, wherein Y is R¹¹—Z—R¹², or wherein Y is Y_A, Y_B or Y_C are as defined hereinbefore wherein L is a —(CH₂CH₂O)_b— group which is directly bonded to the compound of formula IA at the R⁴ position, wherein X is N, wherein b is 1 to 10, preferably 1 to 6, more preferably 1 to 4, wherein R¹ is a CH₃ group wherein said R¹ group may be optionally substituted by one or more groups independently selected from: F; CN; or C(O), wherein, R²ᵃ is OH, F, NH₂ or —CHF₂, wherein R²ᵇ is F, Cl or H, wherein R³ is H, wherein R⁴ is a covalent bond which is C- or O-linked to L, wherein R⁵ is —CH₃, wherein Z is CR⁶R⁷R⁸ and wherein R⁶, R⁷ and R⁸ are all —CH₃ groups or wherein Z is SR⁶R⁷R⁸R⁹R¹⁰ and R⁶ to R¹⁰ are all F groups, wherein R¹¹ is a covalent bond or a —NHC(O)methylbenzyl-group, wherein R¹² is —C(O) or —C(S), wherein R¹³ is H, F or a —(C₁-C₃) alkyl group, and wherein the —(C₁-C₃) alkyl group is optionally substituted by one or more substituents independently selected from: methyl; OH; or F.

Thus there is also provided herein a compound for Formula IA, wherein Y is R¹—Z—R¹², or wherein Y is Y_A, Y_B or Y_C are as defined hereinbefore wherein L is a —(CH₂CH₂O)_b— group which is directly bonded to the compound of formula IA at the R⁴ position, wherein X is C, wherein b is 1 to 10, preferably 1 to 6, more preferably 1 to 4, wherein R¹ is a CH₃ group wherein said R¹ group may be optionally substituted by one or more groups independently selected from: F; CN; or C(O), wherein R²ᵃ is OH, F, NH₂ or —CHF₂, wherein R²ᵇ is F, Cl or H, wherein R³ is H, wherein R⁴ is a covalent bond which is C- or O-linked to L, wherein R⁵ is —CH₃, wherein Z is CR⁶R⁷R⁸ and R⁶, R⁷ and $R^8$ are all —$CH_3$ groups or wherein Z is $SR^6R^7R^8R^9R^{10}$ and $R^6$ to $R^{10}$ are all F groups, wherein $R^{11}$ is a covalent bond or a —NHC(O)methylbenzyl-group, wherein $R^{12}$ is —C(O) or —C(S), wherein $R^{13}$ is H, F or a —($C_1$-$C_3$) alkyl group, and wherein the —($C_1$-$C_3$) alkyl group is optionally substituted by one or more substituents independently selected from: methyl; OH; or F.

Group V. Compounds of formula I with linkage to L at the $R^3$ position.

TABLE V

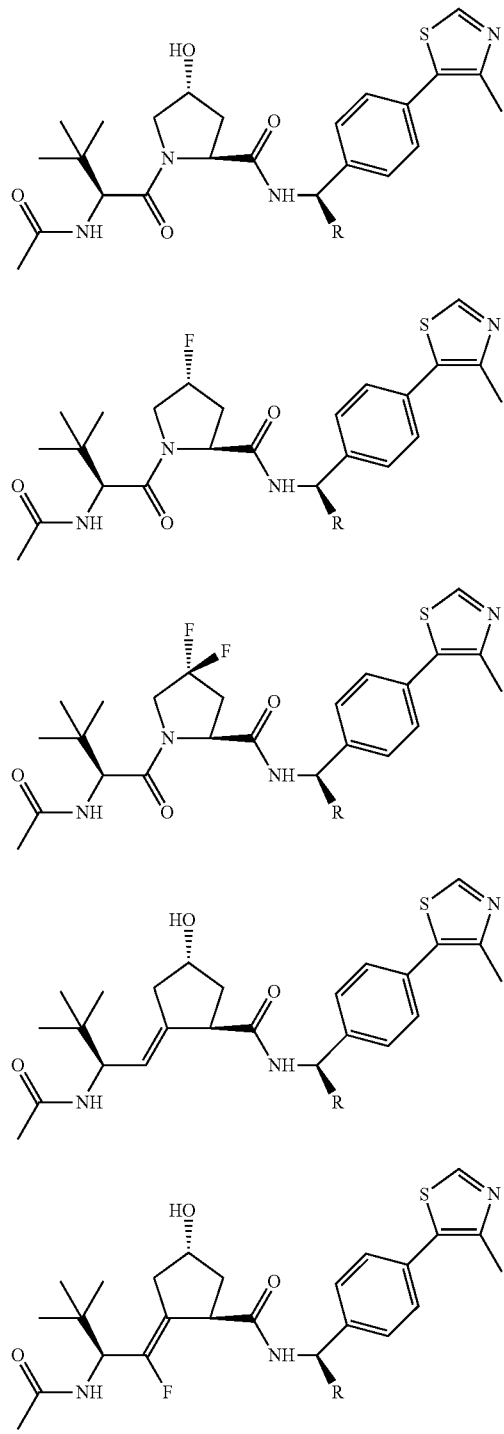

TABLE V-continued

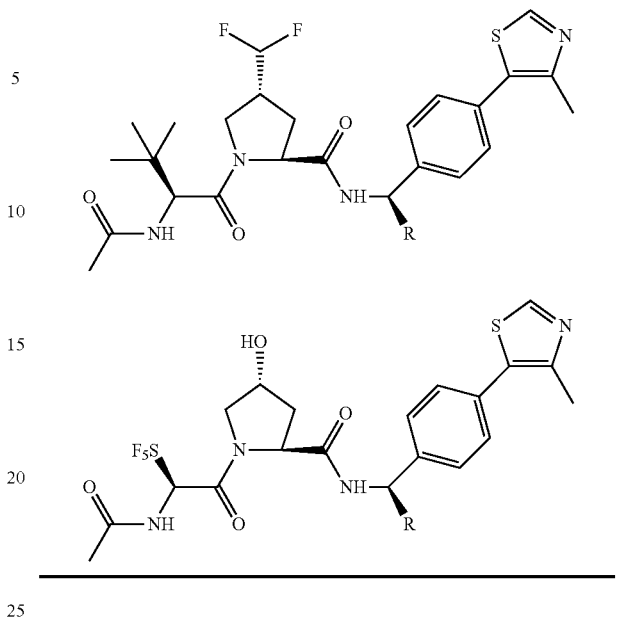

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —$(CH_2CH_2O)_b$— group which is directly bonded to the compound of formula IA at the $R^3$ position, wherein X is N, wherein b is 1 to 10, preferably 1 to 6, more preferably 1 to 4, wherein $R^1$ is a $CH_3$ group wherein said $R^1$ group may be optionally substituted by one or more groups independently selected from: F; CN; or C(O), wherein $R^{2a}$ is OH, F, $NH_2$ or —$CHF_2$, wherein $R^{2b}$ is F, Cl or H, wherein $R^4$ is H, wherein $R^3$ is a covalent bond which is C— or C(O) linked to L, wherein $R^5$ is —$CH_3$, wherein Z is $CR^6R^7R^8$ and $R^6$, $R^7$ and $R^8$ are all —$CH_3$ groups or wherein Z is $SR^6R^7R^8R^9R^{10}$ and $R^6$ to $R^{10}$ are all F groups, wherein $R^{11}$ is a covalent bond or a —NHC(O)methylbenzyl-group, wherein $R^{12}$ is —C(O) or —C(S), wherein $R^{13}$ is H, F or a —($C_1$-$C_3$) alkyl group, and wherein the —($C_1$-$C_3$) alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —$(CH_2CH_2O)_b$— group which is directly bonded to the compound of formula IA at the $R^3$ position, wherein X is C, wherein b is 1 to 10, preferably 1 to 6, more preferably 1 to 4, wherein $R^1$ is a $CH_3$ group wherein said $R^1$ group may be optionally substituted by one or more groups independently selected from: F; CN; or C(O), wherein $R^{2a}$ is OH, F or $NH_2$ or —$CHF_2$, wherein $R^{2b}$ is F, Cl or H, wherein $R^3$ is a covalent bond which is C— or C(O) linked to L, wherein $R^4$ is H, wherein $R^5$ is —$CH_3$, wherein Z is $CR^6R^7R^8$ and $R^6$, $R^7$ and $R^8$ are all —$CH_3$ groups or wherein Z is $SR^6R^7R^8R^9R^{10}$ and $R^6$ to $R^{10}$ are all F groups, wherein $R^{11}$ is a covalent bond or a —NHC(O)methylbenzyl-group, wherein $R^{12}$ is —C(O), or C(S), wherein $R^{13}$ is H, F or a —($C_1$-$C_3$) alkyl group, and wherein the —($C_1$-$C_3$) alkyl group is optionally substituted by one or more substituents independently selected from: methyl; OH; or F.

Group VI. Compounds of formula I with linkage to L at the $R^5$ position.

TABLE VI

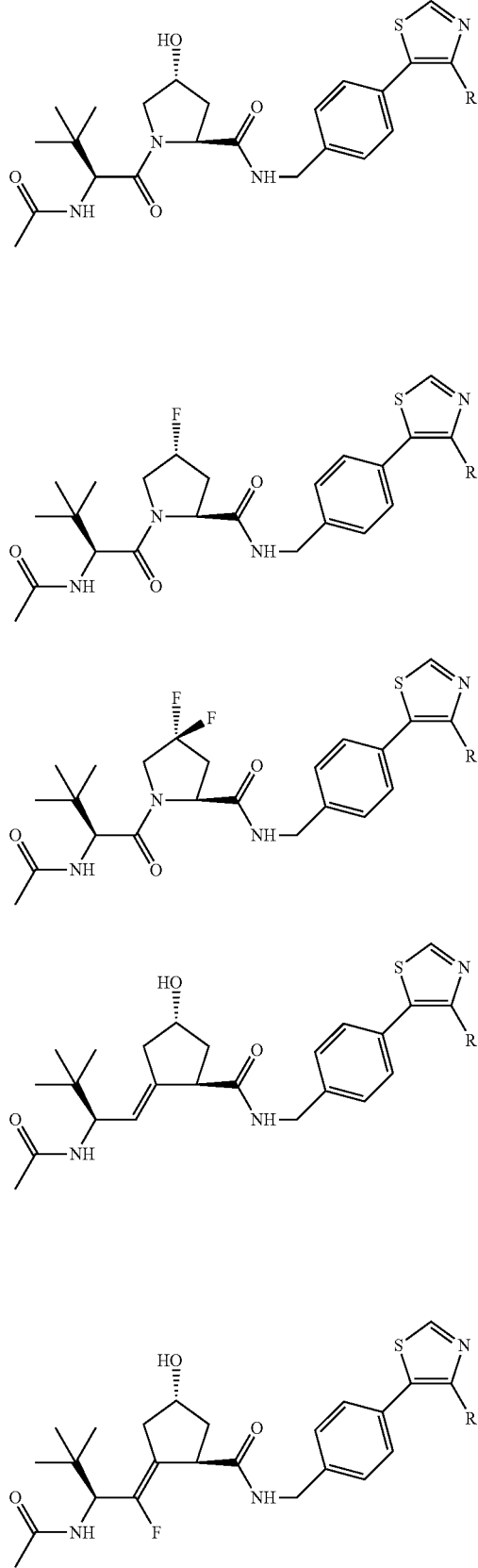

TABLE VI-continued

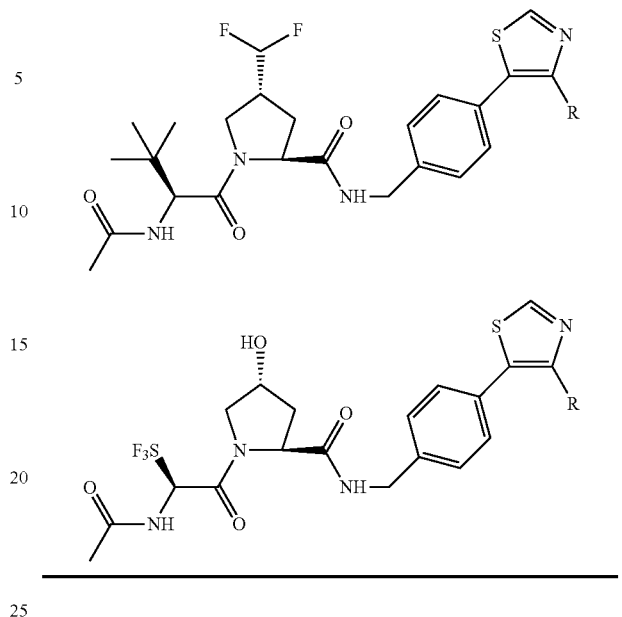

Thus there is also provided herein a compound for Formula IA, wherein Y is $R^1$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^5$ position, wherein X is N, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is a covalent bond which is C-linked to L, wherein Z is CR$^6$R$^7$R$^8$ and $R^6$, $R^7$ and $R^8$ are all —CH$_3$ groups or wherein Z is SR$^6$R$^7$R$^8$R$^9$R$^{10}$ and $R^6$ to $R^{10}$ are all F groups, wherein $R^1$ is a covalent bond or a —NHC(O) methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^5$ position, wherein X is C, wherein b is 1 to 10, preferably 1 to 6, more preferably 1 to 4, wherein $R^1$ is a CH$_3$ group wherein said $R^1$ group may be optionally substituted by one or more groups independently selected from: F; CN; or C(O), wherein $R^{2a}$ is OH, F, NH$_2$ or —CHF$_2$, wherein $R^{2b}$ is F, Cl or H, wherein $R^3$ and $R^4$ are both H, wherein $R^5$ is a covalent bond which is C-linked to L, wherein Z is CR$^6$R$^7$R$^8$ and $R^6$, $R^7$ and $R^8$ are all —CH$_3$ groups or wherein Z is SR$^6$R$^7$R$^8$R$^9$R$^{10}$ and $R^6$ to $R^{10}$ are all F groups, wherein $R^{11}$ is a covalent bond or a —NHC(O) methylbenzyl- group, wherein $R^{12}$ is —C(O) or C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Group VII. Compounds of formula I with linkage to L at the $R^3$ position.

TABLE VII

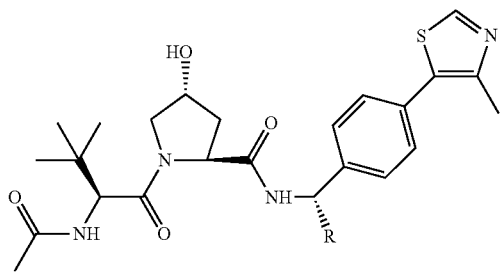

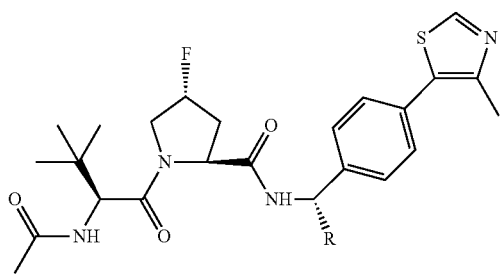

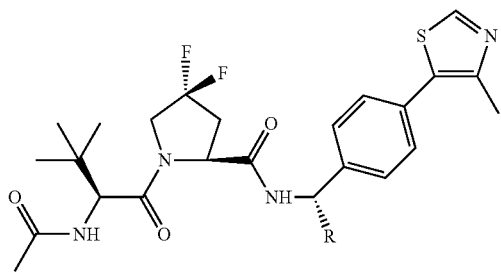

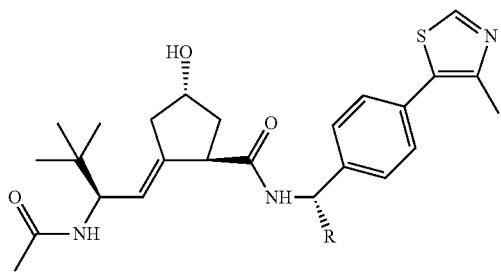

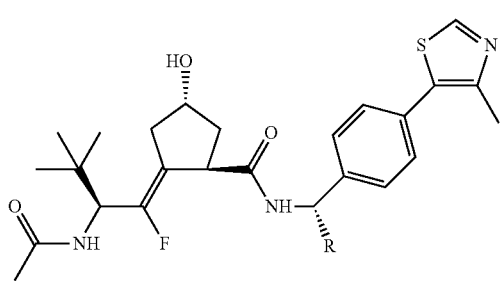

TABLE VII-continued

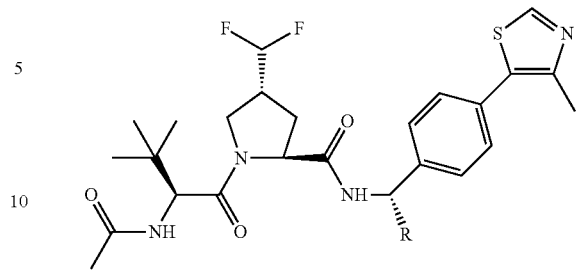

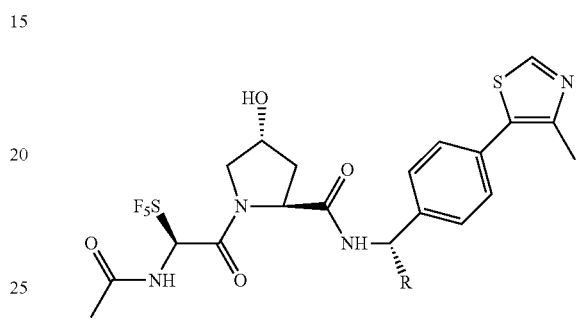

Thus there is also provided herein a compound for Formula IA, wherein Y is $R^{11}$—Z—$R^{12}$, or wherein Y is $Y_A$, $Y_B$ or $Y_C$ are as defined hereinbefore wherein X, $R^1$, $R^{2a}$, $R^{2b}$, $R^4$ to $R^{13}$ are as defined for Group V compounds hereinbefore and wherein L is a —(CH$_2$CH$_2$O)$_b$— group which is directly bonded to the compound of formula IA at the $R^3$ position in accordance with the stereochemistry in Group VII.

Group VIII. Compounds of formula I with linkage to L at the $R^1$ position.

TABLE VIII

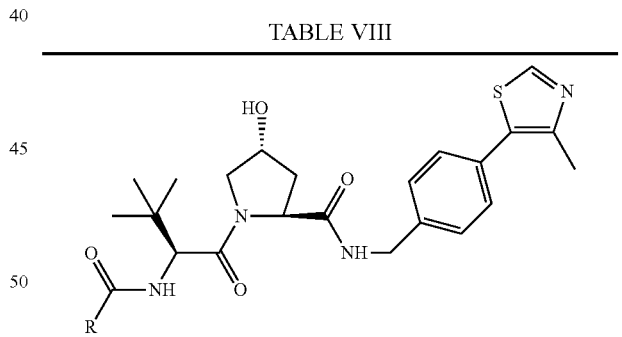

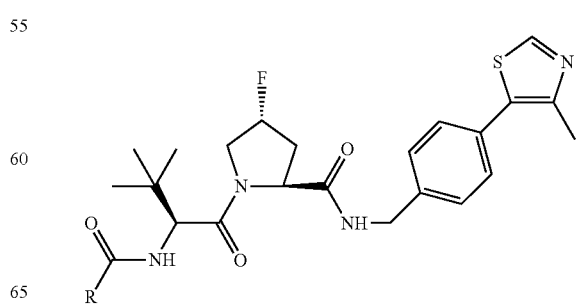

TABLE VIII-continued

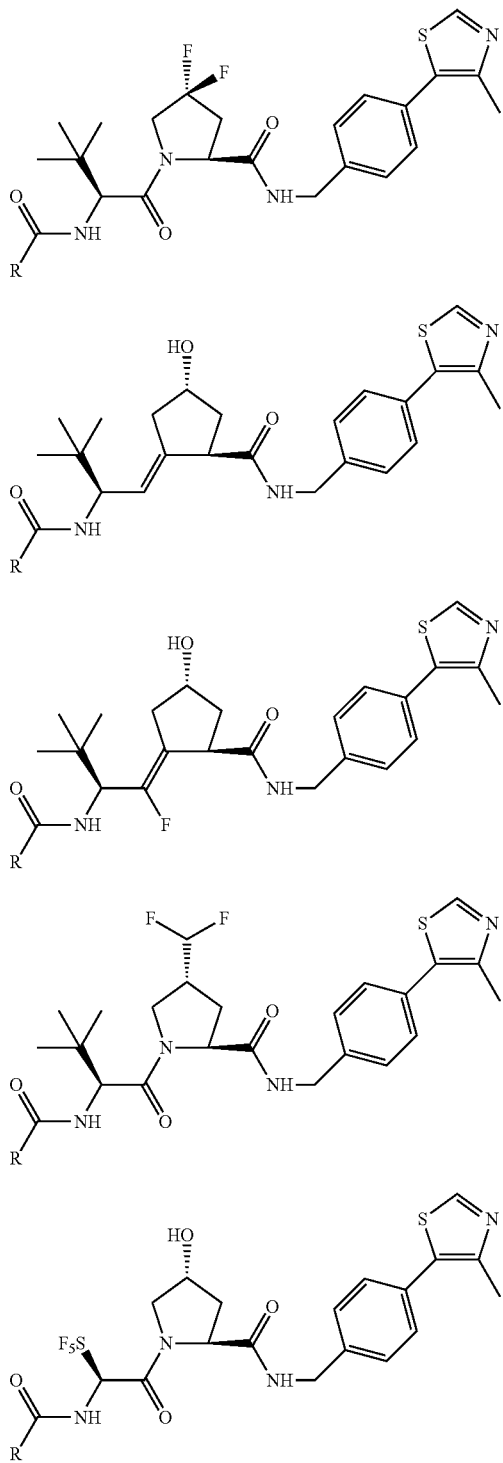

Thus there is also provided herein a compound for Formula IA, wherein Y is $R^{11}$—Z—$R^{12}$, Or wherein Y is $Y_A$, $Y_B$ or $Y_C$ are as defined hereinbefore wherein L is a —(CH$_2$CH$_2$O)$_b$— group which is directly bonded to the compound of formula IA at the $R^1$ position, wherein X is N, wherein b is 1 to 10, preferably 1 to 6, more preferably 1 to 4, wherein $R^1$ is a is a covalent bond which is C-linked to L, wherein $R^{2a}$ is OH, F, NH$_2$ or —CHF$_2$, wherein $R^{2b}$ is F, Cl or H, wherein $R^3$ and $R^4$ are both H, wherein $R^5$ is a CH$_3$ group, wherein Z is CR$^6$R$^7$R$^8$ and $R^6$, $R^7$ and $R^8$ are all —CH$_3$ groups or wherein Z is SR$^6$R$^7$R$^8$R$^9$R$^{10}$ and $R^6$ to $R^{10}$ are all F groups, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Thus there is also provided herein a compound for Formula IA, wherein Y is $R^{11}$—Z—$R^{12}$, or wherein Y is $Y_A$, $Y_B$ or $Y_C$ are as defined hereinbefore wherein L is a —(CH$_2$CH$_2$O)$_b$— group which is directly bonded to the compound of formula IA at the $R^1$ position, wherein X is C, wherein b is 1 to 10, preferably 1 to 6, more preferably 1 to 4, wherein $R^1$ is a is a covalent bond which is C-linked to L, wherein $R^{2a}$ is OH, F, NH$_2$ or —CHF$_2$, wherein $R^{2b}$ is F, Cl or H, wherein $R^3$ and $R^4$ are both H, wherein $R^5$ is a CH$_3$ group, wherein Z is CR$^6$R$^7$R$^8$ and $R^6$, $R^7$ and $R^8$ are all —CH$_3$ groups or wherein Z is SR$^6$R$^7$R$^8$R$^9$R$^{10}$ and $R^6$ to $R^{10}$ are all F groups, wherein $R^{11}$ is a covalent bond or a —NHC(O)methylbenzyl- group, wherein $R^{12}$ is —C(O) or —C(S), wherein $R^{13}$ is H, F or a —(C$_1$-C$_3$) alkyl group, and wherein the —(C$_1$-C$_3$) alkyl group is optionally substituted by one or more substituents independently selected from: methyl; OH; or F.

Processes for the preparation of PROTACs of structure A-L-B are provided in detail in the Chemistry—Materials and Methods hereinafter. In particular processed for the preparation of compounds of Formula I, or Formula IA suitable for linking to L at the $R^1$, $R^3$, $R^4$, $R^5$ or $R^8$ positions to provide PROTACs of structure A-L-B are detailed herein.

A general methodology is to prepare an E3 binding ligands of formula I (A) and then to couple this to a selected linker (L). This furnishes an intermediate azide compound of formula II, and having the structure A-L-N$_3$ as illustrated in Scheme 1 herein. Intermediate compounds of formula II are then subsequently coupled to the desired protein target binding ligand (B) via any suitable coupling reaction, such as for example via reductive amination as illustrated in Scheme 2 herein.

SCHEME 1

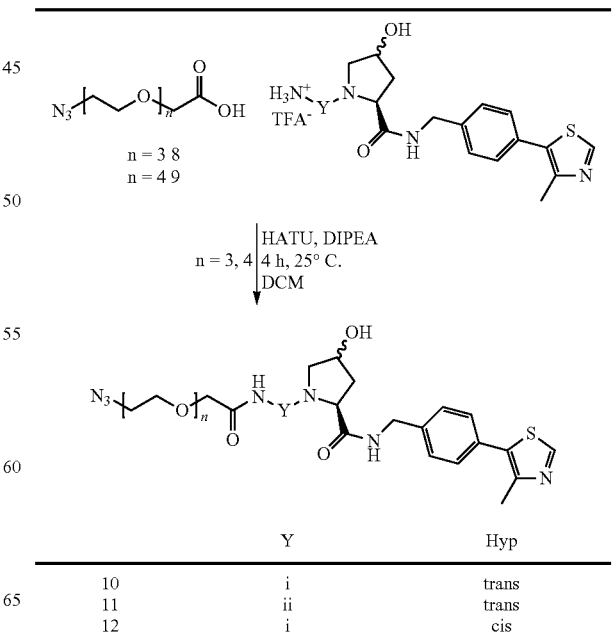

| | Y | Hyp |
|---|---|---|
| 10 | i | trans |
| 11 | ii | trans |
| 12 | i | cis |

SCHEME 1-continued

|    | n | Y  | Hyp   |
|----|---|----|-------|
| 13 | 3 | i  | trans |
| 14 | 4 | i  | trans |
| 15 | 3 | ii | trans |
| 16 | 3 | i  | cis   |

Y =

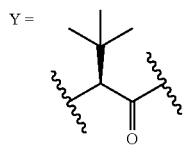

i

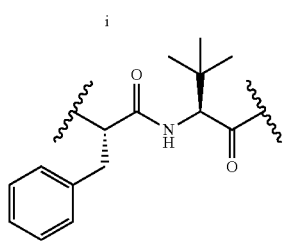

ii

Scheme 1 provides a route for formation of the intermediate azide compounds (13) to (16) as detailed in the Examples section hereinafter, from the corresponding amines (10) to (12). As will be appreciated by the skilled chemist, via use of the linker coupling methodology as outlined in Scheme 1, and the general methodologies for the preparation of azide-linker groups and compounds of formula I, as provided in Schemes 3 and 4 in the Examples section herein, any compound of formula I as detailed herein may be linked together with any suitable linker group L to provide an intermediate azide of formula II, having the structure Az-L-A. The invention additionally provides compounds of formula II as defined herein.

SCHEME 2

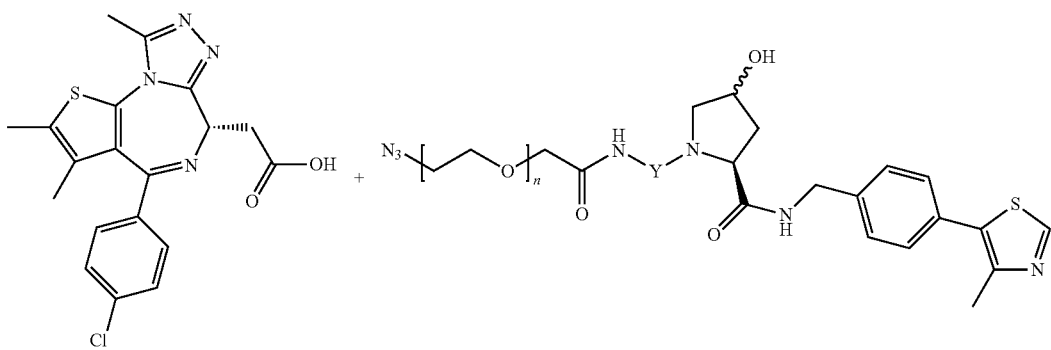

17

1. Pd/C, H₂, 3 h, 25° C., MeOH
2. HATU, DIPEA, 18 h, 25° C., DCM

SCHEME 2-continued

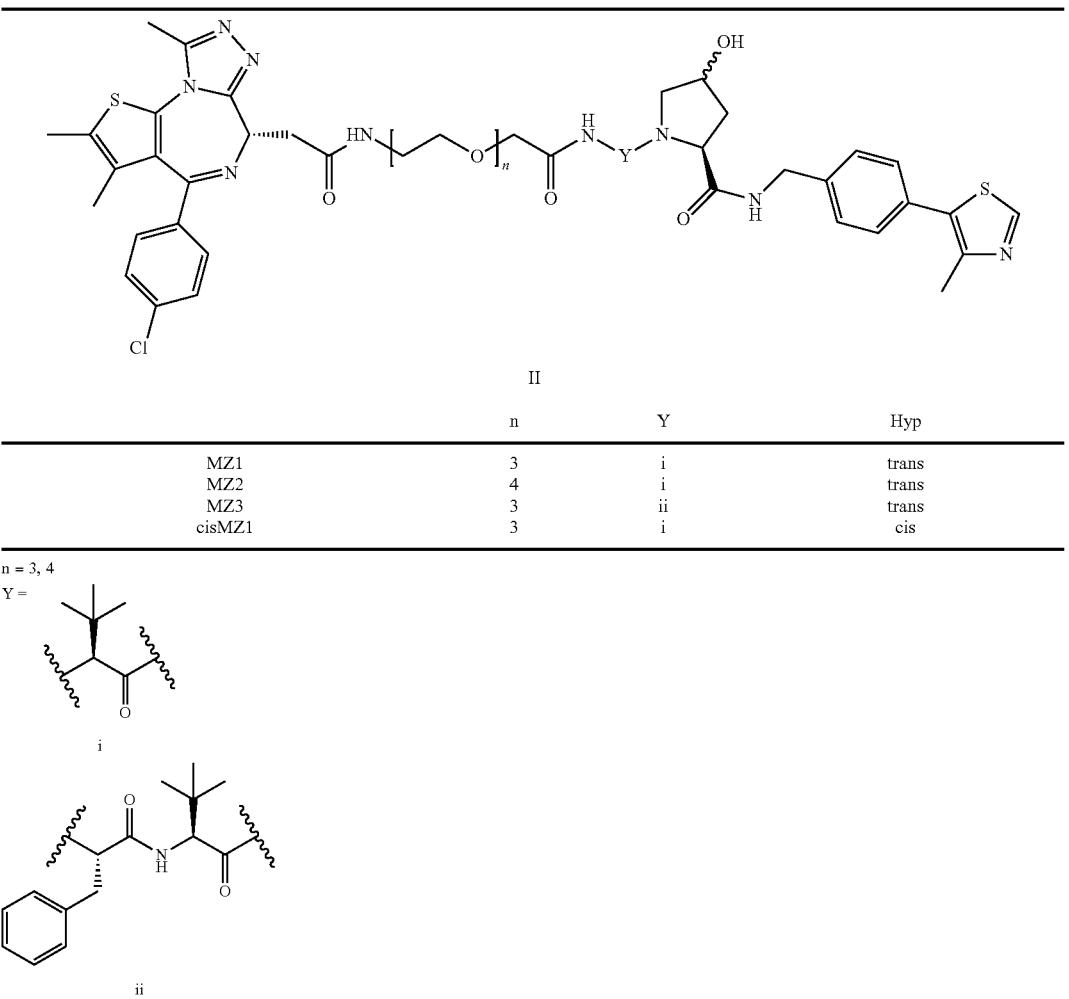

II

|      | n | Y  | Hyp   |
|------|---|----|-------|
| MZ1  | 3 | i  | trans |
| MZ2  | 4 | i  | trans |
| MZ3  | 3 | ii | trans |
| cisMZ1 | 3 | i | cis   | n = 3, 4

Whilst Scheme 2 provides a route for formation of the PROTAC compounds MZ1, MZ2 and MZ2 as detailed in the Examples section hereinafter, from the corresponding azides of formula II as will be appreciated by the skilled chemist, via use of the methodology outlined in Scheme 2, any azide compound of formula II as detailed herein may be linked together with any protein target binding ligand B via coupling of the linker group L with B to provide A-L-B as defined herein.

The PROTAC compounds of structure A-L-B can be prepared in accordance with the general methods as outlined in Schemes 1 and 2 herein, and in particular in accordance with the experimental procedures detailed in the Chemistry—Materials and Methods hereinafter. As will be readily appreciated by the skilled chemist, suitable protection/deprotection strategies may be employed to protect vulnerable functional groups on the compounds of formulae I and/or II during one or more of the coupling steps.

BRIEF DESCRIPTION OF FIGURES

FIG. 6a-time dependent treatment of HeLa cells with MZ1 at concentrations of I 10 nM, II 50 nM, III 250 nM, IV 500 nM. FIG. 6b-time dependent treatment of HeLa cells with MZ2 at concentrations of I 100 nM, II 250 nM, III 500 nM, and IV 1 µM. FIG. 6c-time dependent treatment of HeLa cells with MZ3 at concentrations of I 500 nM and II 1 µM.

FIG. 8a, DMSO 0.01%; FIG. 8b, JQ1 1 µM; FIG. 8c, MZ1 100 nM; FIG. 8d, MZ1 250 nM; FIG. 8e, MZ1 500 nM; FIG. 8f, MZ1 1 µM; FIG. 8g, MZ2 500 nM; FIG. 8h, MZ2 1 µM; FIG. 8i, MZ3 500 nM, and FIG. 8j, MZ3 1 µM.

FIG. 10a, with single treatment of MZ1 for 4 h and then exchange of media; FIG. 10b, single treatment with MZ1 at t=0 but no exchange of media; and FIG. 10c, single treatment with 0.01% DMSO for 4 h and then exchange of media.

BIOLOGICAL METHODS

Figure 1:
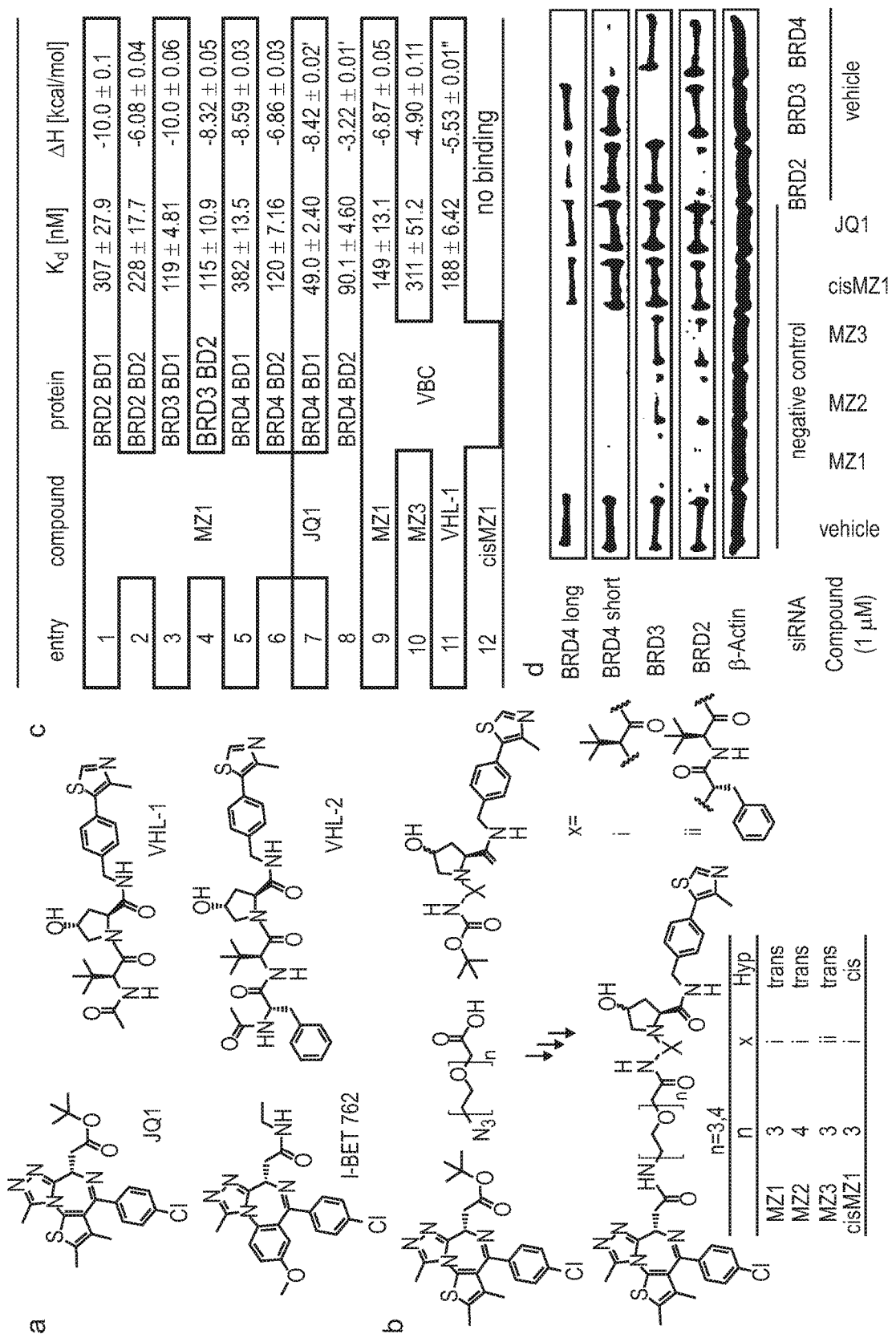
FIG. 1a: illustrates the structures of compounds JQ1, VHL-1, I-BET 762 and VHL-2.
FIG. 1b: illustrates the two-step synthetic strategy for preparing PROTAC compounds MZ1, MZ2, MZ3 and cisMZ1.
FIG. 1c: illustrates the binding affinities and ΔH against first and second bromodomains, and VBC obtained in isothermal titration calorimetry (ITC) experiments.
FIG. 1d: illustrates HeLa cells were treated with either siRNA targeting individual BET proteins or negative control siRNA 24 h prior to treatment with the compounds MZ1-3, cisMZ1, and JQ1 or vehicle control (0.01% DMSO) for an additional 24 h. Abundance of individual BET protein was analyzed by Western blotting using corresponding specific antibodies accordingly after SDS-PAGE.

Biophysics
Protein Expression and Purification:
Plasmids pNIC28-Bsa4 containing the single BET bromodomain constructs BRD2 BD1, BRD2 BD2, BRD3 BD1, BRD3 BD2, BRD4 BD1 and BRD4 BD2 for protein expression were obtained in accordance with the methods provided in Baud, M. G. J. et al. Chemical biology. A bump-and-hole approach to engineer controlled selectivity of BET bromodomain chemical probes. *Science* 346, 638-41 (2014). Subsequent expression and purification was based on the ukZuber et al methods with slight modifications. Single colonies from freshly transformed plasmid DNA in competent *E. coli* BL21(DE3) cells were grown overnight at 37° C. in 10 mL of LB medium with 50 µg/mL kanamycin. Starter culture was then diluted 1:100 in fresh Luria Broth (LB) medium with 50 µg/mL of kanamycin. Cell growth was allowed at 37° C. and 200 rpm to an optical density of about 2.5 (OD600), at which point temperature was decreased to 18° C. Once the cultures equilibrated at 18° C., protein expression was induced overnight at 18° C. with 0.4 mM isopropyl-3-thiogalactopyranoside (IPTG). The bacteria was harvested the next day by centrifugation (8000 rpm for 10 minutes at 6° C., JLA 8.1000 rotor on a Beckman Coulter Avanti J-20 XP centrifuge) and frozen at −20° C. as pellets for storage. Pellets of cells expressing $His_6$-tagged proteins were re-suspended in lysis buffer (50 mM HEPES pH 7.5 at 25° C., 150 mM NaCl, 40 mM Imidazole and 2 mM f3-mercaptoethanol). One tablet of Complete Protease Inhibitor Cocktail (Roche) was added to the re-suspension and cells were lysed using a French Press at 4° C. Following a 20 min incubation period at room temperature with 10 µg/mL DNaseI and 10 mM $MgCl_2$, the cell debris was removed by centrifugation, 20,000×g at 4° C. The lysate was purified via immobilized metal ion affinity chromatography on a His Trap HP 5 mL Ni sepharose column (GE Healthcare Life Sciences) on an AKTApure system (GE Healthcare). $His_6$-tagged protein was eluted using a linear gradient to 250 mM imidazole in the same buffer. After Ni purification, the pooled elution fractions were concentrated to a volume of 4 mL and further purified by size exclusion chromatography on a Superdex 75 16/60 Hiload gel filtration column (GE Healthcare) on an AKTApure system using the following buffer: 20 mM HEPES pH 7.5, 150 mM NaCl. Samples were monitored by SDS-polyacrylamide gel electrophoresis to verify purity. Pure protein was then flash frozen with liquid nitrogen and stored at −80° C. The mass and purity of the proteins were subsequently verified by mass spectrometry.

Isothermal Titration Calorimetry (ITC):

ITC experiments were carried out at an ITC 200 instrument from MicroCal™ with a concentration in the measuring cell of 15 µM and a syringe concentration of 150 µM. Experiments were conducted as PROTAC into protein titrations, except in the case of MZ3 where protein was titrated into PROTAC. BET protein experiments were conducted in a buffer containing 20 mM HEPES with 100 mM NaCl at pH 7.5 and a temperature of 30° C.

Reagents

The proteasome inhibitor MG132 and radio immunoprecipitation assay buffer (RIPA-buffer) were purchased from Sigma Aldrich. DMEM media, phosphate buffered saline (PBS) and heat deactivated fetal bovine serum (FBS) were purchased from Gibco, Life Technologies. Complete Mini EDTA free Protease inhibitor cocktail was purchased from Roche. Lipofectamine® RNAiMAX Transfection Reagent from Life Technologies. siRNA from Life Technologies, cat. #4390843, 4392420 (s12070), 4390824(s15545 & s23901). FuGene 6 Transfection Reagent from Promega (E2691).

Tissue Culture

HeLa and U2OS cells were cultured in DMEM supplemented with 10% FBS, 1% L-glutamine and 100 U/ml of penicillin/streptomycin. Cells were maintained for no more than 30 passages at 37° C. and 5% $CO_2$.

Cell Treatment

Small Interfering RNA

For siRNA inhibition studies, cells were plated in six-well plates and were grown to 50-60% confluence. Cells were transfected with siRNA targeting BRD2, BRD3 or BRD4 or negative control siRNA at a final concentration of 12 nM in the presence of lipofectamine reagent. After transfection, cells were cultured for another 24 hours for treatment with PROTAC compound or harvested after 48 hours for gene expression study.

Single Time Point Treatment

For treatment experiments cells were transferred in 6-well plates with 500 000 cells per well in 2 ml media. 12 h after settling 200 µl of media was removed and then replaced by a 10 fold concentrated compound solution in media. The final DMSO concentration was 0.01% v/v.

Time Course Experiments

For time dependent treatment cells were transferred in 6-well plates with 300 000 cells per well in 2 ml media. For treatment 200 µl of media was removed and then replaced by a 10 fold concentrated compound solution in media. Treatment was conducted at given time points prior to harvest.

Protein Recovery Experiment

Cells were transferred in 6-well plates with 300 000 cells per well in 2 ml media. For treatment 200 µl of media was removed and then replaced by a 10 fold concentrated compound solution in media. 4 h after treatment the media was aspirated and replaced by fresh media without treatment. Cells were harvested at given time points.

Western Blotting

For protein extracts the dishes were placed on ice. The media was aspirated and the tissue layer washed twice with ice cold PBS. 120 µl of RIPA-buffer containing Protease inhibitor was added and the cells detached from the surface with a cell scraper. After removal of the insoluble fraction by centrifugation the protein concentration of the supernatant was determined by a Pierce™ BCA Protein Assay Kit. Protein extracts were fractionated by SDS-PAGE on 3-8% Tris-Acetate NuPage® Novex® (Life Technologies) polyacrylamide gels and transferred to a nitrocellulose membrane using i-Blot® 2 from Life Technologies. The membrane was then blocked with 3.5% Bovine Serum albumin (BSA) in Tris-buffered saline (TBS) with 0.1% Tween-20. For detecting proteins the following primary antibodies in the given concentrations were used: anti-BRD2 (Abcam, ab139690, EPR7642) 1:2000, anti-BRD3 (Abcam, ab50818, 2088C3a) 1:500, anti-BRD4 (Abcam, ab128874, EPR5150 (2)) 1:1000, anti-Hif-1α (BD Biosciences, 610959, clone 54) 1:1000, anti-VHL (Cell Signaling Technology, 2738S) 1:750, anti-(β-Actin (Cell Signaling Technology, 4970S, 13E5) 1:2000. For visualisation a Li-Cor Biosciences Odyssey system with the following secondary fluorescent Antibodies from Li-Cor Biosciences was used: IRDye800CW Goat Anti-Mouse (926-32210), IRDye800CW Donkey Anti-Rabbit (926-32213), both in concentrations of 1:10 000. Membranes were incubated with the corresponding antibodies either at 4° C. for 12 h or at 25° C. for 4 h. Between incubation with the different antibodies membranes were stripped with 0.25 M solution of Glycine.HCl at pH 2.

RNA Extraction and Real-Time PCR

Expression levels of genes of interest were analysed by RT-PCR. After treatment described above, cells were harvested and RNA was extracted with Qiagen RNeasy Mini Kit (cat. #: 74104). Reverse transcription were performed using 250-500 ng of extracted RNA with Bio-Rad iScript cDNA synthesis Kit (cat. #: 170-8891). The cDNA samples were diluted by 25-fold. Gene-specific primers were designed with aid of UCSC Genome Browser as described in Baratta, M. G. et al. An in-tumor genetic screen reveals that the BET bromodomain protein, BRD4, is a potential therapeutic target in ovarian carcinoma. Proc. Natl. Acad. Sci. U.S.A 112, 232-7 (2014).

S1. Primers for RT-PCR

| SEQ ID Number | Name | Sequence (5'→3') |
|---|---|---|
| SEQ ID NO: 1 | AREG-fw | AAGGAGAAGCTGAGGAACGAA |
| SEQ ID NO: 2 | AREG-rv | TGGCTATGACTTGGCAGTGA |
| SEQ ID NO: 3 | FAS-fw | AGAACTTGGAAGGCCTGCAT |
| SEQ ID NO: 4 | FAS-rv | GTCTGGTTCATCCCCATTGA |
| SEQ ID NO: 5 | FGFR1-fw | CTGACCACAGAATTGGAGGC |
| SEQ ID NO: 6 | FGFR1-rv | GCAGGTGTAGTTGCCCTTGT |
| SEQ ID NO: 7 | MYC-fw | CCGCTTCTCTGAAAGGCTCT |
| SEQ ID NO: 8 | MYC-rv | AAGCTAACGTTGAGGGGCAT |
| SEQ ID NO: 9 | P21-fw | TGGAGACTCTCAGGGTCGAA |
| SEQ ID NO: 10 | P21-rv | GGATTAGGGCTTCCTCTTGG |
| SEQ ID NO: 11 | TYRO3-fw | AACTACGAAGATCGGGGAC |
| SEQ ID NO: 12 | TYRO3-rv | CCAGGCCTTTTAGGTTGTGA |
| SEQ ID NO: 13 | GAPDH-fw | AACGGGAAGCTTGTCATCAATGGAAA |
| SEQ ID NO: 14 | GAPDH-rv | GCATCAGCAGAGGGGCAGAG |

All PCR reactions were performed using the Bio-Rad CFX96 Touch Real-Time PCR system and the amplifications were done using the Quanta PerfeCTa® SYBR® Green FastMix for iQ (cat. #95071). The thermal cycling conditions were composed of 95° C. for 10 min, 45 cycles at 95° C. for 10s and 60° C. for 30s followed by a ramping temperature step to 95° C. for melt-curve analysis. The experiments were carried out in triplicate for each data point. The data was analysed using CFX Manager software from Bio-Rad and the relative quantification in gene expression was determined by normalising to the control gene GAPDH.

Fluorescence Microscopy:

HeLa cells transiently expressing GFP-tagged BRD4 were prepared. Plasmid pcDNA5/FRT/TO-GFP containing full-length wild-type BRD4 is obtained in accordance with the Baud et al methodology as referred to hereinbefore. HeLa cells were plated onto a glass bottom microwell dish (MatTek, P35G-1.5-14-C) in 2.5 mL medium and were grown to 50-60% confluence. Then the cells were transfected with 4 µg of plasmid DNA in the presence of FuGene 6 Transfection Reagent (Promega, E2691). Twelve hours after transfection, medium was removed in exchange of fresh medium supplemented with 0.5 µg/mL tetracycline to induce GFP-BRD4 expression. After 18 hours, medium was removed again in exchange of fresh medium without tetracycline. After 6 hours, PROTAC compound MZ1 or cis-MZ1 were added to the plate. Immediately after the treatment, fluorescence given out from individual cells plate were observed on a DeltaVision Elite imaging system with excitation at 480 nm and emission at 525 nm. Images of individual cells were made at regular time interval to observe changes in fluorescence over time.

Biological Data for Activity of Compounds—in HeLa Cells

The biological activity of PROTAC compounds of structure A-L-B was first investigated in HeLa cells.

To demonstrate that PROTACs of structure A-L-B are able to induce degradation of BET proteins, HeLa cells transfected with control siRNA were treated with 1 µM of a PROTAC compound of structure A-L-B, MZ1-3 alongside with negative controls JQ1 and cisMZ1 for 24 h. This data is illustrated in FIG. 1d. In parallel, HeLa cells with BRD2, BRD3 and BRD4 individually and separately silenced by transfection with the respective siRNA were treated with vehicle DMSO to compare the protein depletion effect of RNAi knockdown and PROTACs of structure A-L-B.

BET protein abundance was evaluated by SDS-PAGE in accordance with literature methodology followed by Western blot using corresponding specific antibodies to probe for BRD2, BRD3 or BRD4, respectively. All three PROTAC compounds, MZ1, MZ2 and MZ3 demonstrated complete removal of BRD4 with no detectable protein observed after 24 h of treatment. In contrast, removal of BRD2 and BRD3 was not complete after 24 h. MZ1 exhibited highest efficacy among the three compounds. MZ2, which is structurally analogous to MZ1 except for a longer linker containing four PEG units, showed a weaker removal effect compared to MZ1. MZ3, containing an additional phenylalanine moiety between the linker and the VHL ligand, was less effective at removing BRD2 and BRD3 versus MZ1 and MZ2.

For detecting proteins the following commercially available primary antibodies in the given concentrations were used: anti-BRD2 (Abcam, ab139690, EPR7642) 1:2000, anti-BRD3 (Abcam, ab50818, 2088C3a) 1:500, anti-BRD4 (Abcam, ab128874, EPR5150(2)) 1:1000, anti-Hif-1α (BD Biosciences, 610959, clone 54) 1:1000, anti-VHL (Cell Signaling Technology, 2738S) 1:750, anti-(β-Actin (Cell Signaling Technology, 4970S, 13E5) 1:2000, anti-hHR23b (Abcam, ab86781) 1:2000, anti-DDB1 (Abcam, ab109027, EPR6089) 1:50000.

For visualisation the commercially available Odyssey system from Li-Cor Biosciences with the following commercially available secondary fluorescent Antibodies from Li-Cor Biosciences was used: IRDye800CW Goat Anti-Mouse (926-32210), IRDye800CW Donkey Anti-Rabbit (926-32213), both in concentrations of 1:10 000.

In combination the protein degradation, depletion and abundance data has demonstrated the potent and effective degradation of BET proteins by PROTACs of structure A-L-B in accordance with the present invention. Surprisingly this data additionally indicates a preferential degradation effect on BRD4 over BRD2 and BRD3.

The preferential degradation effect on BRD4 over BRD2 and BRD3 by PROTACs of structure A-L-B in accordance with the present invention was unexpected because the parental compound JQ1 is known to be a pan-BET inhibitor and each of the three PROTACs of structure A-L-B which were tested have been demonstrated to bind with similar affinities to BET bromodomains.

The Applicant has conducted further characterization of PROTACs of structure A-L-B to provide additional support for this unprecedented single target selectivity.

Figure 2:
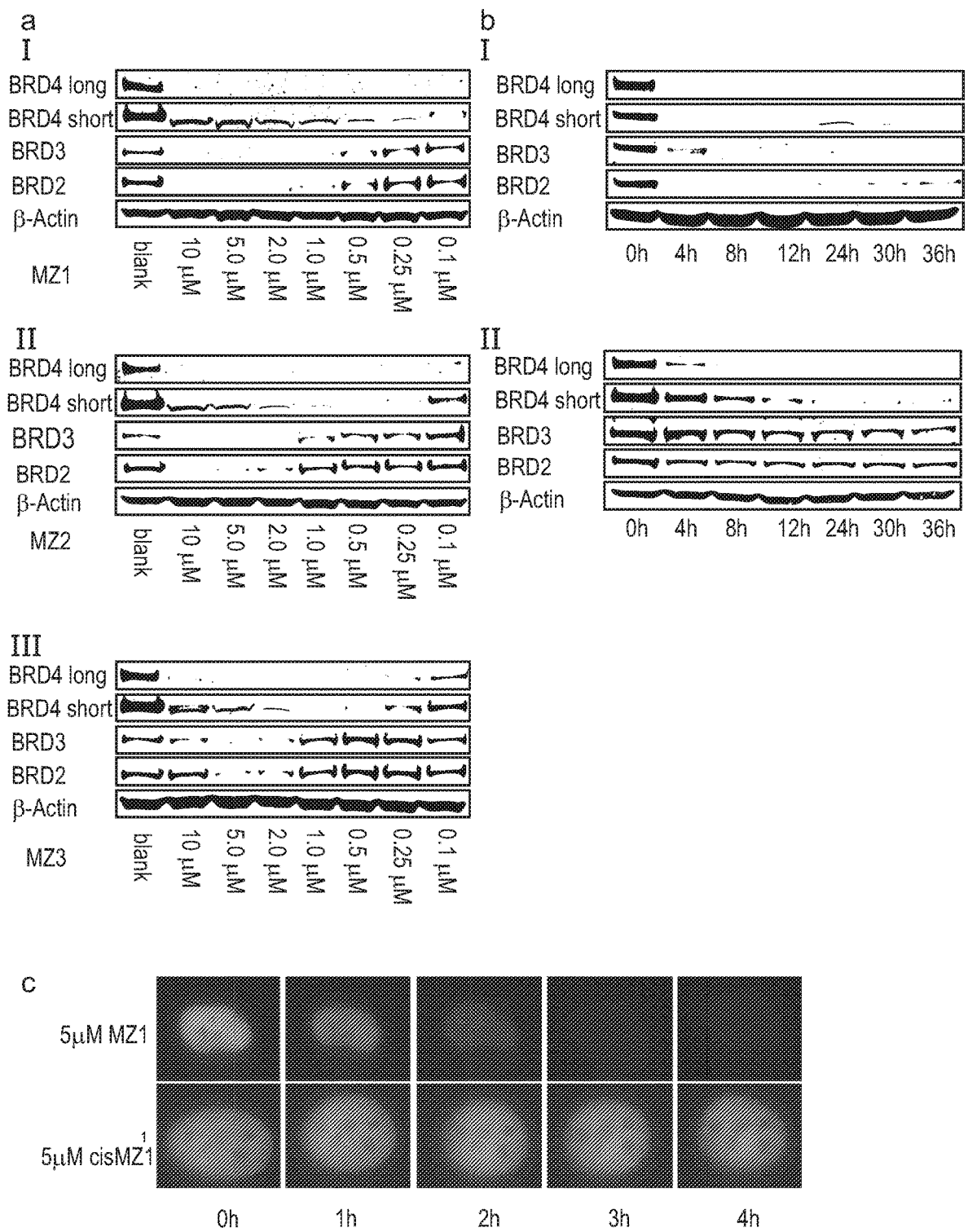
FIG. 2a: illustrates the compound dose- and time-dependent intracellular activities results obtained when HeLa cells were first treated with various concentrations of three PROTACs, (i) MZ1, (ii) MZ2 and (iii) MZ3.
FIG. 2b: illustrates the results of monitoring the cellular BET protein levels over time in HeLa cells treated with (i) 1 μM and (ii) 0.1 μM of MZ1.
FIG. 2c: illustrates U2OS cells transfected with GFP-BRD4 which were treated with either 5 μM of MZ1 or cisMZ1 over a time course of 4 h. The BRD4 degradation over time was followed by live fluorescence imaging.

Experimental Data for Compound Dose- and Time-Dependent Intracellular Activities To assess the compound dose- and time-dependent intracellular activities, HeLa cells were first treated with various concentrations of three PROTACs, MZ1, MZ2 and MZ3, FIG. 2a. All three PROTACs showed concentration dependent BET removal activity with higher activity at higher concentration. As in the initial experiment, MZ1 proved the most active compound, with more than 90% of all BET proteins being removed at compound concentration down to 1 µM.

Figure 6:
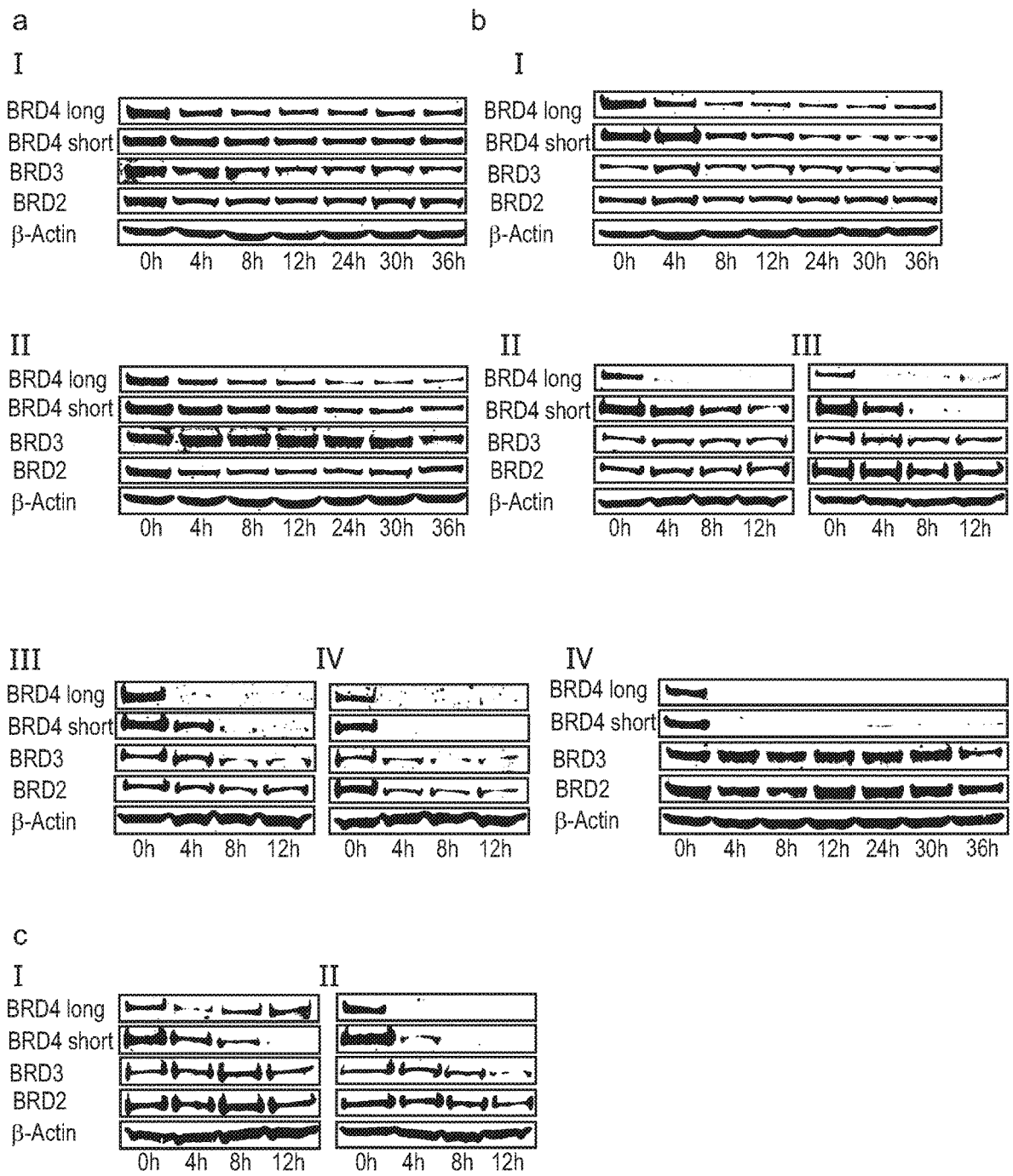
FIG. 6: illustrates Time dependent treatment of HeLa cells with compounds MZ1, MZ2 and MZ3 at different concentrations.
Figure 7:
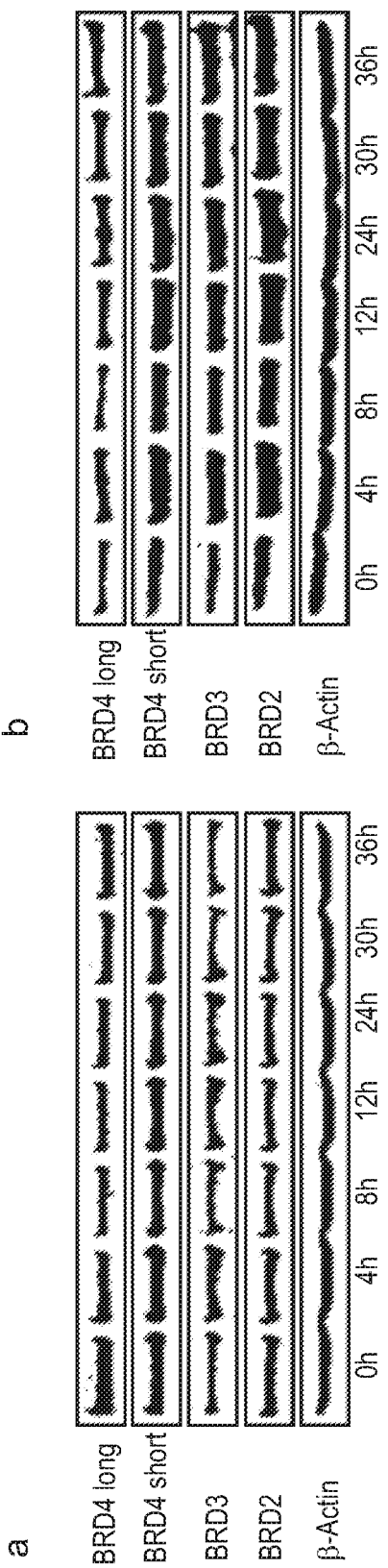
FIG. 7: illustrates the Time dependent treatment over 36 h of HeLa cells with (a) 0.01% DMSO, (b) 1 µM JQ1.

Remarkably, these experiments have confirmed the preferential removal of BRD4 over BRD2 and BRD3 with all three PROTAC compounds. This preference is more prominent with treatment at lower concentration of PROTACs, e.g. 0.1-0.5 µM. To study the activities of PROTACs of structure A-L-B over time, HeLa cells were treated with 1 µM or 0.1 µM of MZ1 and cellular BET protein levels were monitored in a time course experiment. FIG. 2b illustrates the representative data with MZ1, and FIG. 6 illustrates additional data with other compounds. Progressive removal of BET proteins over time was observed in all experimental set-ups, however BRD4 consistently exhibited strongest and fastest reduction in protein level. Reassuringly, no BET protein degradation was observed in the presence of either DMSO or JQ1 or cisMZ1 (FIG. 3a), as confirmed by the data illustrated in FIG. 7 and FIG. 3a respectively.

Figure 8:
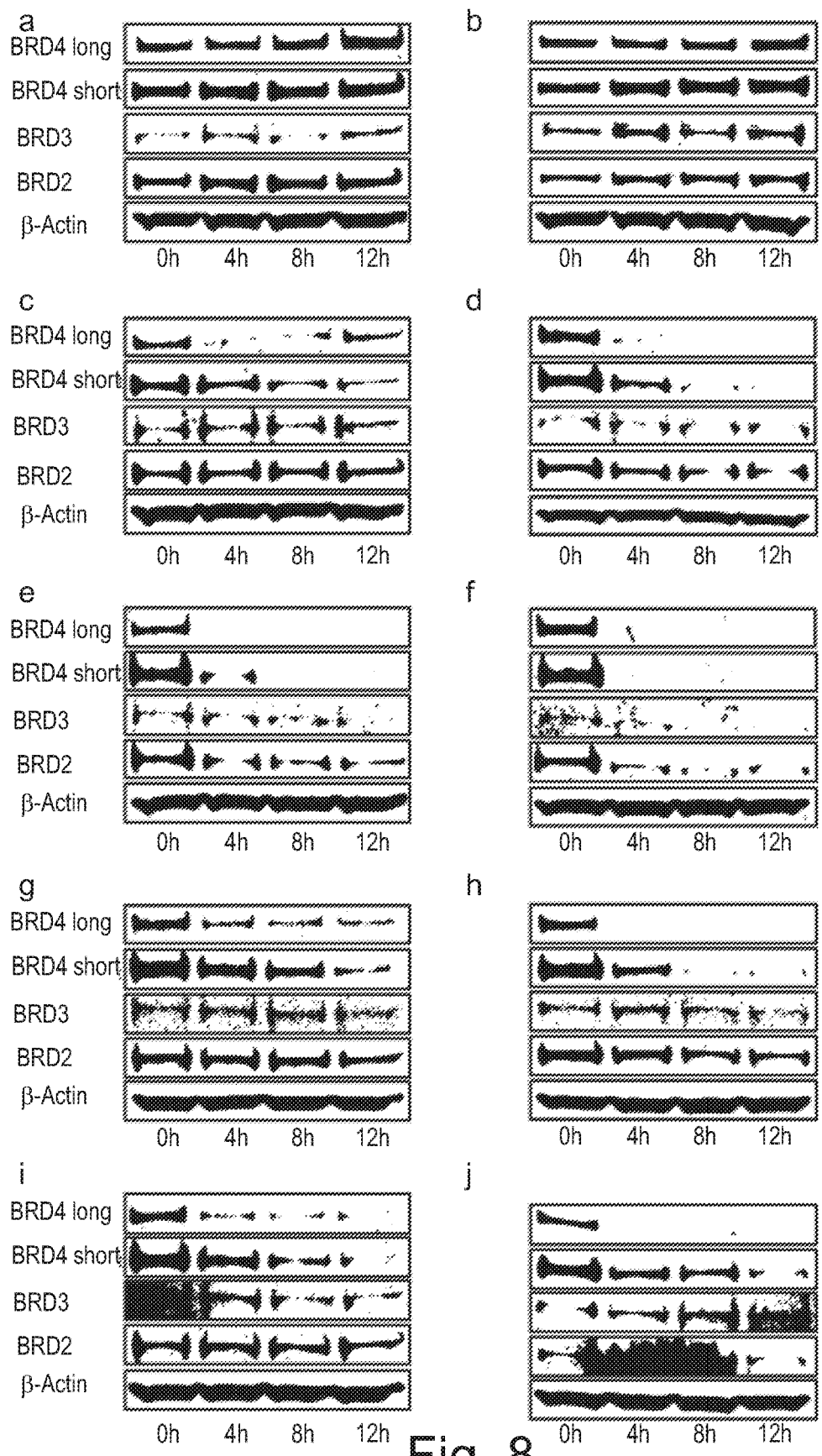
FIG. 8: illustrates U2OS cells treated over a time course of 12 h in 4 h intervals with the following compounds and concentrations.

To verify whether the observation of preferential removal for BRD4 by PROTACs of structure A-L-B can be observed in another cell line, the same study was carried out in U2OS osteosarcoma cells and the same activity profile was observed. This data is illustrated in FIG. 8.

Figure 9:
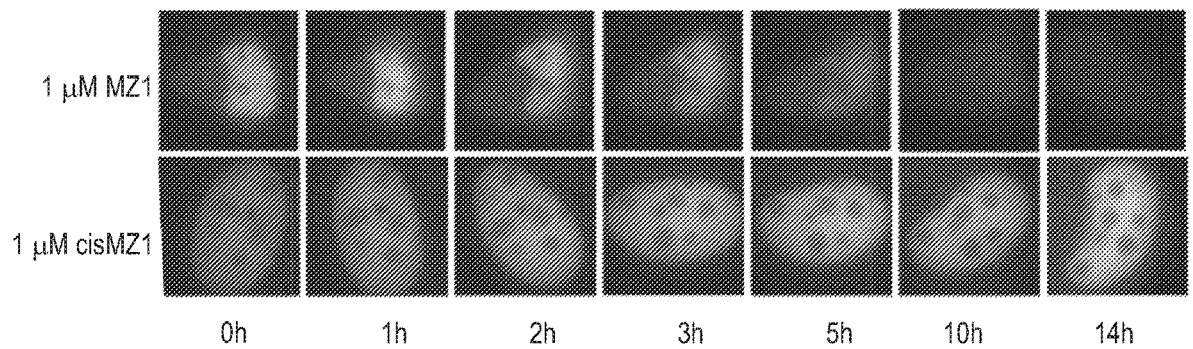
FIG. 9: illustrates U2OS cells, transfected with GFP-BRD4 were treated with either 1 µM of MZ1 or cisMZ1 over a time course of 14 h. BRD4 degradation was followed by live fluorescence imaging.

To visualize the BET protein degradation process, U2OS cells were transfected with a plasmid coding for a green fluorescent protein (GFP) tagged BRD4 protein, allowing fluorescence readout of BRD4 within the cell nuclei. Cells expressing GFP-BRD4 were treated after 24 h with either 5 µM of MZ1 or 5 µM of cisMZ1 and the fluorescence was observed over time. In the presence of the active PROTAC compound MZ1 a complete depletion of the fluorescence signal was observed after just 3 h, whereas cisMZ1 caused no change in the fluorescence signal over the course of the experiment. The results of these experiments are illustrated in FIG. 2c and FIG. 9.

This data confirmed that BRD4 is removed from the cell nuclei in a time dependent manner due to the presence of a PROTAC compound of structure A-L-B, MZ1.

Taken together, the results from these experiments have confirmed that the time and dose-response activity profiles for PROTACs of structure A-L-B provide rapid and effective PROTAC-induced degradation of BRD4 in a selective manner over BRD2 and BRD3.

Experimental Data for Mechanism

To gain mechanistic insights, the VHL- and proteasome-dependency of PROTAC-mediated protein degradation were first examined. As illustrated by the results shown in FIG. 3a, cisMZ1 was unable to induce degradation of any of the BET-proteins over time, demonstrating that PROTAC efficacy is dependent on productive recruitment of VHL. The reliance of the PROTAC-induced protein degradation on proteasome activity was assessed using proteasome inhibitor MG-132. Treatment with MG132 completely abrogated MZ1-induced degradation of all BET proteins. This is confirmed by comparison of lanes 3 and 6 in FIG. 3b, and establishes the expected proteasome-dependence of the approach. Interestingly however, MG132 treatment in the absence of a PROTAC of structure A-L-B showed no significant accumulation in BET protein levels, either alone or in combination with JQ1. This is confirmed by comparison of lanes 1 and 2 with 4 and 5 in FIG. 3b, respectively. These results suggest that basal proteasome activity level against BET proteins is negligible under those conditions and only becomes significant as a result of treatment with a PROTAC compound of structure A-L-B as provided by the present invention.

Biological Data for PROTAC Treatment on E3 Ligase (VHL) Levels

To further evaluate the biological activity of PROTAC compounds of structure A-L-B, the Applicant determined whether treatment with PROTACs of structure A-L-B had any effect on the levels of its target E3 ligase (VHL) and on the level of HIF-1α, the natural substrate of VHL.

Figure 3:
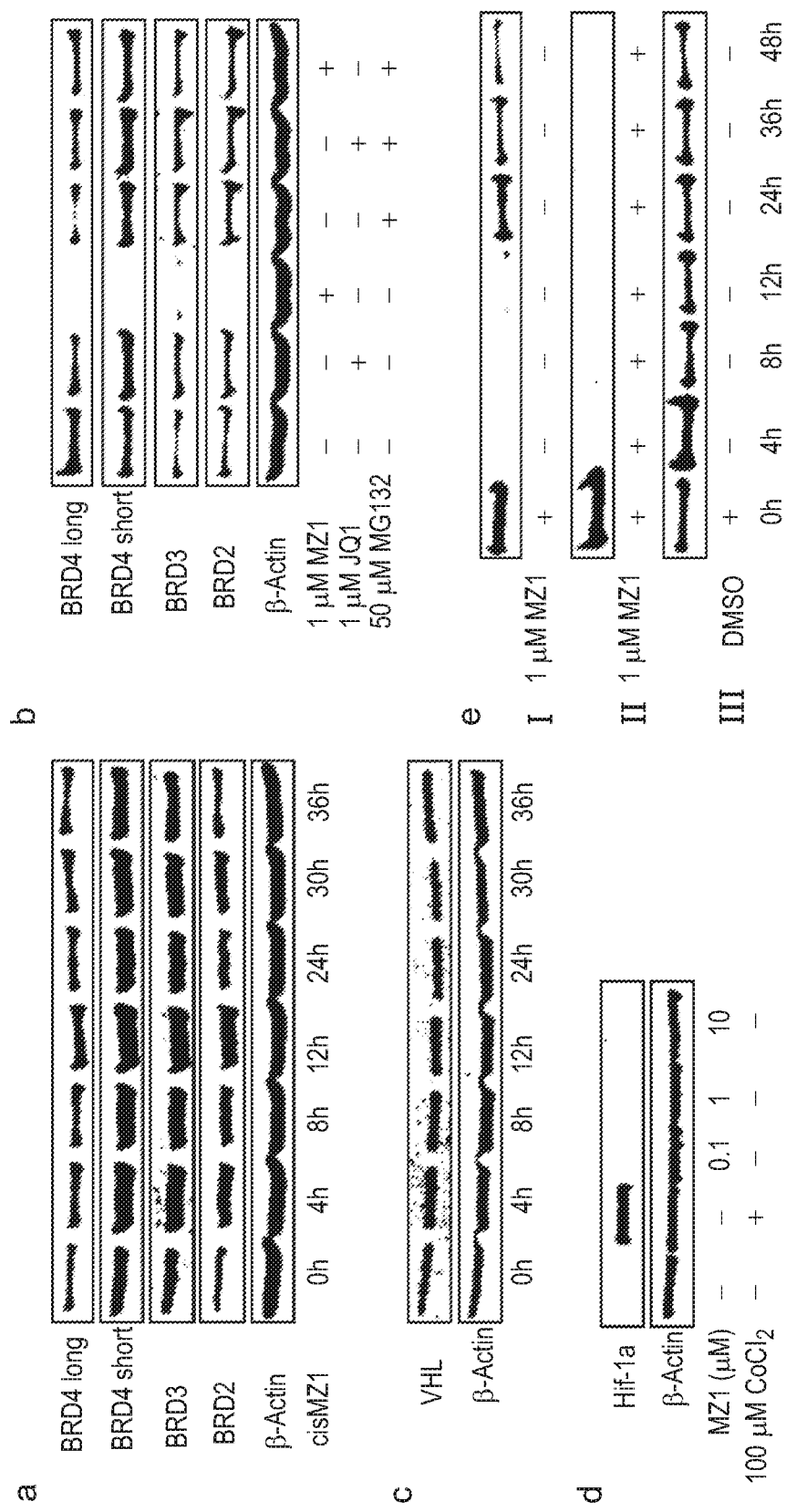
FIG. 3a: illustrates the results of BRD2, BRD3 and BRD4 protein degradation experiments in time dependent treatment over 36 h of HeLa cells with 1 μM inactive compound cisMZ1.
FIG. 3b: illustrates the results of experiments to determine the impact of MG-132 on the degradation of BET proteins with MZ1.
FIG. 3c: illustrates the results of experiments to determine the impact of MZ1 on the on VHL levels over 36 hours.
FIG. 3d: illustrates the results of experiments to determine the presence or absence of HIF-1α stabilization observed when HeLa cells were treated with MZ1, or cobalt (II) chloride, as a hypoxia mimicking positive control.
FIG. 3e: illustrates the BRD4 protein levels observed (panel I) with single treatment of MZ1 at t=0 for 4 h and then exchange of media, (panel II) single treatment with MZ1 at t=0 but no exchange of media, and (panel III) single treatment with 0.01% DMSO for 4 h and then exchange of media.

As demonstrated by the data illustrated in FIG. 3c, VHL levels in the presence of a PROTAC compound, MZ1 (1 µM) remained unaffected over the course of up to 36 h. This data indicates that the amount of E3 ligase is not influenced by PROTAC binding. On the other hand, as the VHL ligand portions of the present PROTACs occupy the same binding site on VHL that is used to recruit HIF-1α, the present PROTACs could also effectively block HIF-1α binding to VHL to an extent that it may lead to potential stabilization of HIF-1α within cells.

Such an effect would not be desirable as up-regulation of HIF-1α transcriptional activity would potentially confound the effects resulting from degradation of BET proteins which could result in induction of the hypoxic response, and potentially give rise to unwanted side effects. To assess whether any HIF-1α stabilization could be observed, HeLa cells were treated with PROTAC, MZ1 and also with cobalt (II) chloride, as a hypoxia mimicking positive control.

Figure 10:
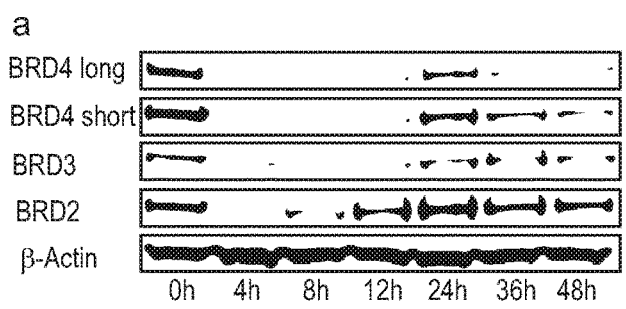
FIG. 10: illustrates BET protein levels observed in different treatments, specifically.
Figure 10:
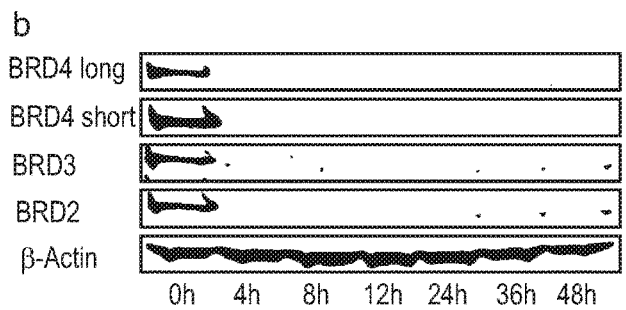
Figure 10:
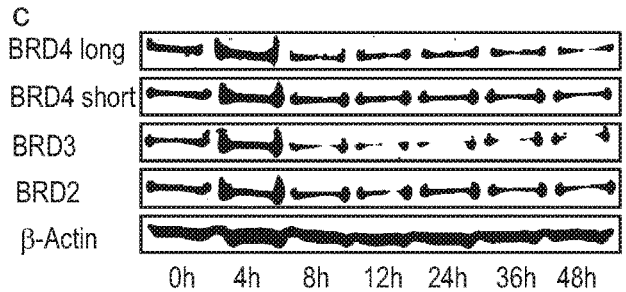

The results of these experiments did not reveal any evidence of HIF-1α stabilization, even at concentrations of MZ1 up to 10 µM, whilst clear HIF-1α stabilization was observed in the presence of $CoCl_2$. These findings are illustrated in FIG. 3d. To determine whether the removal of BET proteins by treatment with the present PROTACs of structure A-L-B— is reversible, and to establish how long it would take for cells to reverse the effect, HeLa cells were initially treated for 4 h with 1 µM of MZ1, after which the compound was removed from the media and then monitoring of the protein levels was carried out over a further period of 48 h. The washed cells showed detectable recovery of intracellular BRD4 only by 20 h after washout, while in the absence of the wash step no protein could be detected even after 48 h. These findings are illustrated in FIG. 3e. FIG. 10 illustrates the results obtained for the corresponding experiments monitoring time-dependent levels of BRD2 and BRD3.

Taken together, these results demonstrate that PROTAC-induced protein degradation is strictly dependent on binding to VHL, on proteasome activity, and does not interfere with the normal endogenous levels of both VHL and HIF-1α.

Furthermore, the observed degradation effect is not only rapid but also sustained and long lasting, even upon removal of the compound.

BET inhibitors such as JQ1 are known to influence the expression of an assortment of genes. Selective targeting of individual BET family members would be predicted to elicit distinct and more limited transcriptional responses, because the genome occupancy patterns of BET proteins are not identical. To evaluate the functional consequences of removing BET proteins using PROTACs of structure A-L-B, and in particular of inducing selective degradation of BRD4 over BRD2 and BRD3, the Applicant has monitored the mRNA expression profiles of a selection of cancer-related genes which respond to JQ1 treatment and BET protein inhibition: MYC, P21, AREG, FAS, TYRO3 and FGFR1. The dependence of MYC and P21 expression on BRD4 activity is well characterized. MYC stimulates cell cycle progression and is constantly expressed upon misregulation in cancer thus leading to continuous overexpression of downstream MYC-dependent genes. In bone associated tumors as well as leukemia and lymphoma cell lines JQ1 treatment or silencing of BRD4 has been shown to result in down regulation of MYC. MYC represses transcription of the cell cycle CDK inhibitor P21, a tumor suppressor. Down regulation of MYC and consequent de-repression of P21 promotes cell cycle arrest. In contrast to the well characterized BRD4-dependency of MYC and P21, FAS, which encodes a proapoptotic protein belonging to the tumor necrosis factor receptor family, is down-regulated by depletion of BRD2, while for the growth factors AREG and FGFR1 as well as the protein tyrosine kinase TYRO3 little is known about any BET protein specific regulation.

As these four genes are known to strongly respond to treatment with JQ1, therefore they were included as representative set of genes to compare between the pan-BET inhibitory effect caused by JQ1 and a selective BRD4 degradation caused by a PROTAC of structure A-L-B, MZ1.

Figure 4:
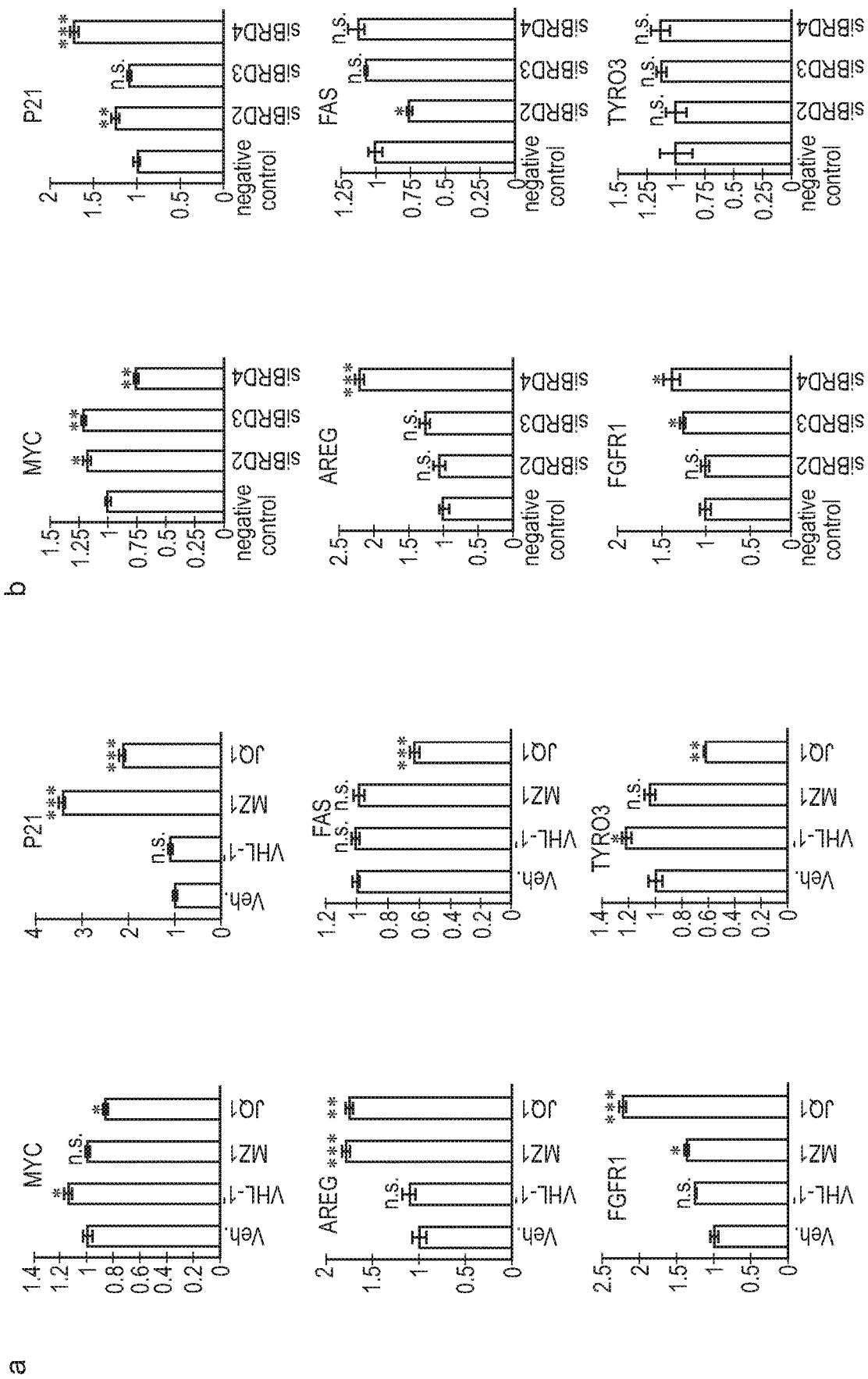
FIGS. 4a and 4b: show that selective degradation of BRD4 leads to a differential response between JQ1 and MZ1 on selected genes. mRNA expression profiles of MYC, P21, AREG, FAS, FGFR1, and TYRO3 upon treatment with PROTAC MZ1 and JQ1 were compared. (a) HeLa cells were treated with 100 nM MZ1, VHL-1', or JQ1 or 0.01% DMSO vehicle control (Veh.) for 24 h. (b) To mimic the protein removal effect, HeLa cells were transfected with siRNA targeting individual BRD2, BRD3, or BRD4 or negative control siRNA and were harvested after 48 h. Quantitative PCR was performed to analyze relative gene expression level of treated HeLa cells using target specific primers. Gene expression levels relative to GAPDH were normalized to control treatment. The data shown represent the mean±SEM (n=3 technical replicates) of one experiment. Statistical significance compared to the control was determined with two-tailed t tests: *P<0.05, P<0.01, *P<0.001, and n.s.=not significant.
Figure 5:
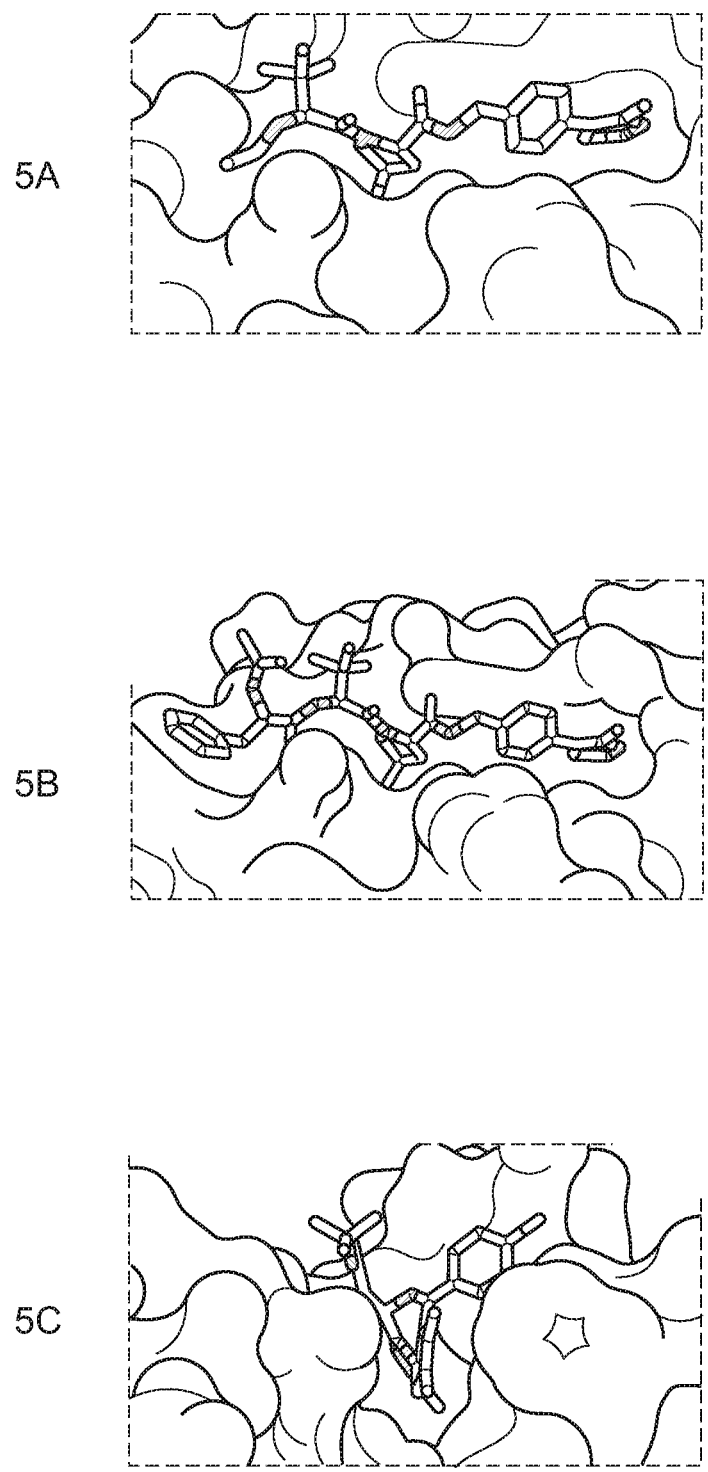
FIG. 5A: is a representation of the protein-ligand crystal structure of VHL-1 where the scaffold of VHL-1 is seen in 3D-format.
FIG. 5B: is a representation of the protein-ligand crystal structure of VHL-2 where the scaffold of VHL -2 is seen in 3D-format.
FIG. 5C: is a representation of the protein-ligand crystal structure of JQ1 where the scaffold of JQ1 is seen in 3D-format.
Figure 11:
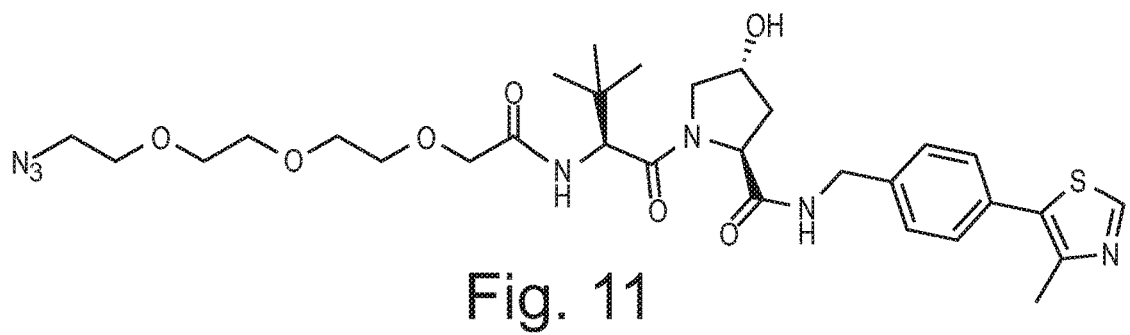
FIG. 11: illustrates the structural formula of negative control VHL-1-linker compound VHL-1'.
Figure 12:
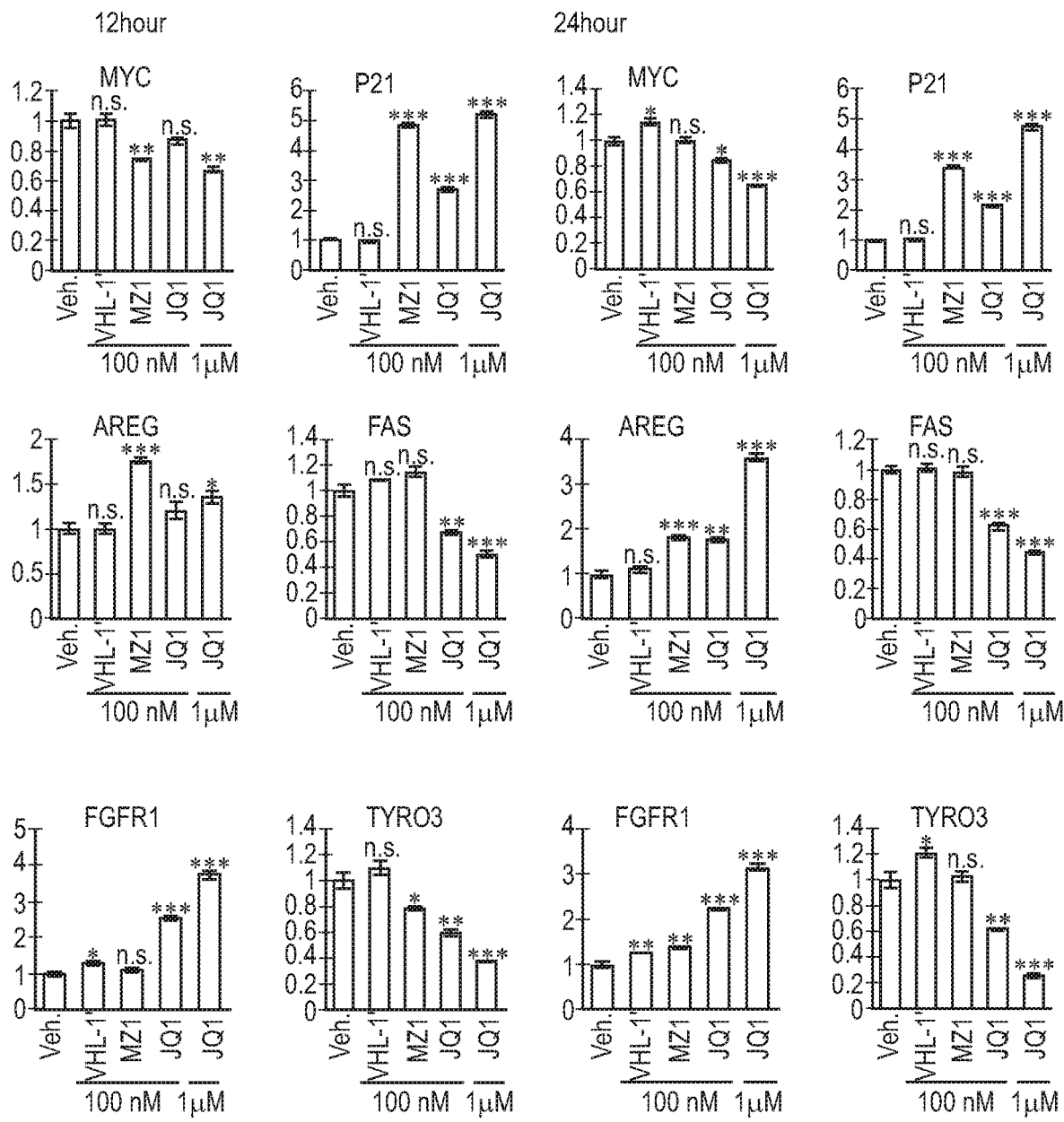
FIG. 12: illustrates the comparison of mRNA expression profiles of MYC, P21, AREG, FAS, FGFR1 and TYRO3 upon treatment with MZ1 and JQ1. HeLa cells were treated with 100 nM of MZ1, VHL-1', or JQ1, or 1 µM of JQ1 or 0.01% DMSO vehicle control (Veh.) for (A) 12 hours or (B) 24 hours. Quantitative PCR was performed to analyze relative gene expression level of treated HeLa cells using target specific primers. Gene expression levels relative to GAPDH were normalized to control treatment. The data shown in FIG. 12 represents the mean±SEM (n=3, technical replicates) of one experiment. Statistical significance compared to the control was determined with two-tailed t tests: *P<0.05; P<0.01; *P<0.001; n.s. not significant.

Treatment with MZ1 at 100 nM for 24h was chosen as this provided an optimal condition and the lowest effective concentration for achieving selective degradation of BRD4 over BRD2 and BRD3 whilst at the same time minimizing potential interference due to BET bromodomains inhibition, as illustrated in the results shown in FIG. 2a at panel I and in FIG. 2b at panel II. In addition, treatments with negative control VHL-1-linker compound VHL-1', illustrated in FIG. 11, which lacks the JQ1 moiety, as well as with JQ1 were also conducted to provide comparisons. Treatment of MZ1 resulted in down regulation of MYC, similar to JQ1, after 12 h, as illustrated in FIG. 12, although MYC levels recovered after 24 h. Treatment with MZ1 and JQ1 resulted in similar upregulation of P21 and AREG both after 12 h, as also illustrated in FIG. 12 and 24 h, as illustrated in FIG. 4a.

Interestingly, and in contrast to JQ1 which resulted in significant changes on FAS, TYRO3 and FGFR1, the PROTAC of structure A-L-B, MZ1 showed more subtle and less significant effects on these genes. These results are illustrated in FIG. 4a and FIG. 12.

Figure 13:
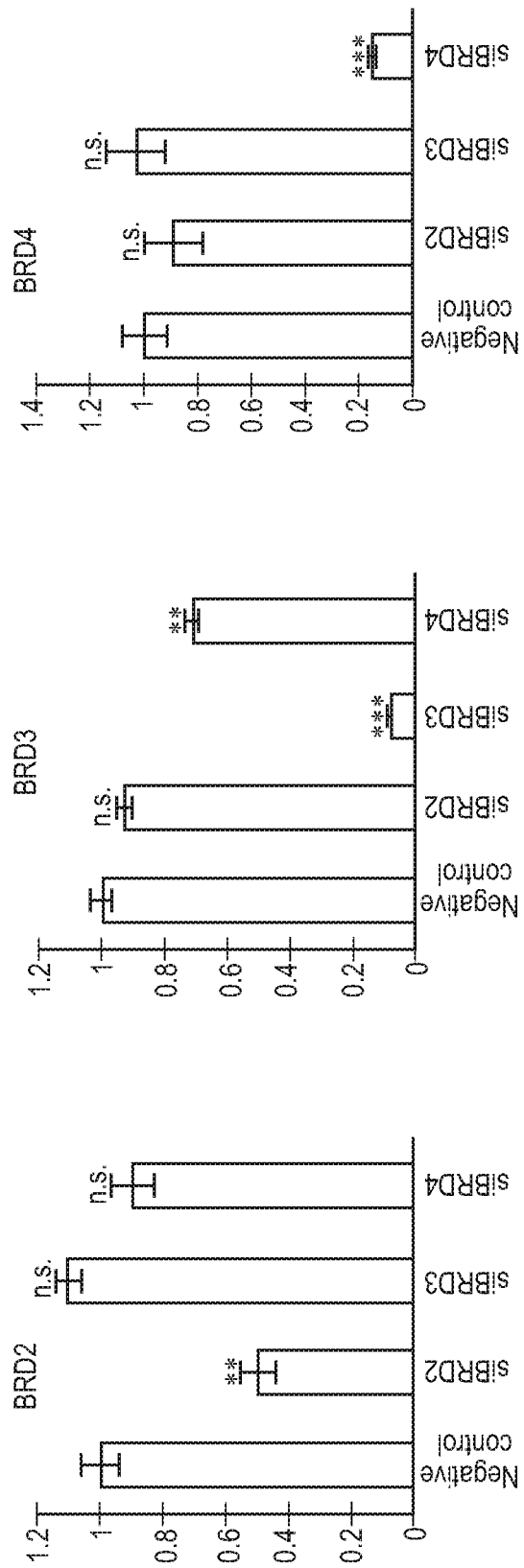
FIG. 13: Verification of the effectiveness of siRNA suppression of BET genes. mRNA expression of BRD2, BRD3 and BRD4 were selectively suppressed upon transfection of their respective siRNA. HeLa cells were transfected with siRNA targeting individual BRD2, BRD3 or BRD4 or with negative control siRNA and were harvested after 48 hours. Quantitative PCR was performed to analyze relative gene expression level of treated HeLa cells using target specific primers. Gene expression levels relative to GAPDH were normalized to control treatment. The data shown in FIG. 13 represents the mean±SEM (n=3, technical replicates) of one experiment. Statistical significance compared to the control was determined with two-tailed t tests: *P<0.05; P<0.01; *P<0.001; n.s. not significant.
Figure 14:
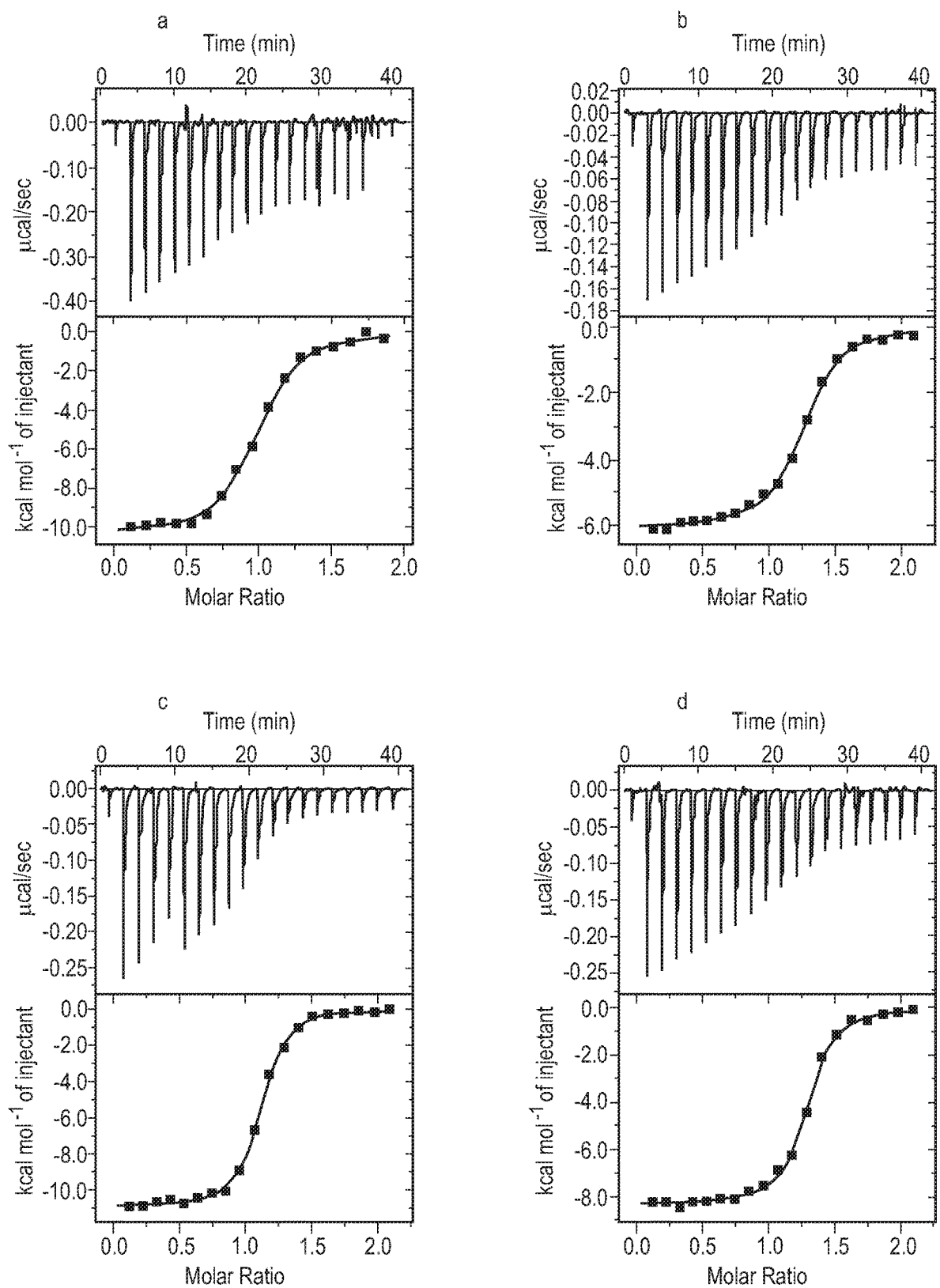
FIG. 14a: illustrates isothermal titration calorimetry (ITC) plots obtained over time from treatment of MZ1 against BRD2 BD1.
FIG. 14b: illustrates isothermal titration calorimetry (ITC) plots obtained over time from treatment of MZ1 against BRD2 BD2.
FIG. 14c: illustrates isothermal titration calorimetry (ITC) plots obtained over time from treatment of MZ1 against BRD3 BD1.
FIG. 14d: illustrates isothermal titration calorimetry (ITC) plots obtained over time from treatment of MZ1 against BRD3 BD2.
Figure 15:
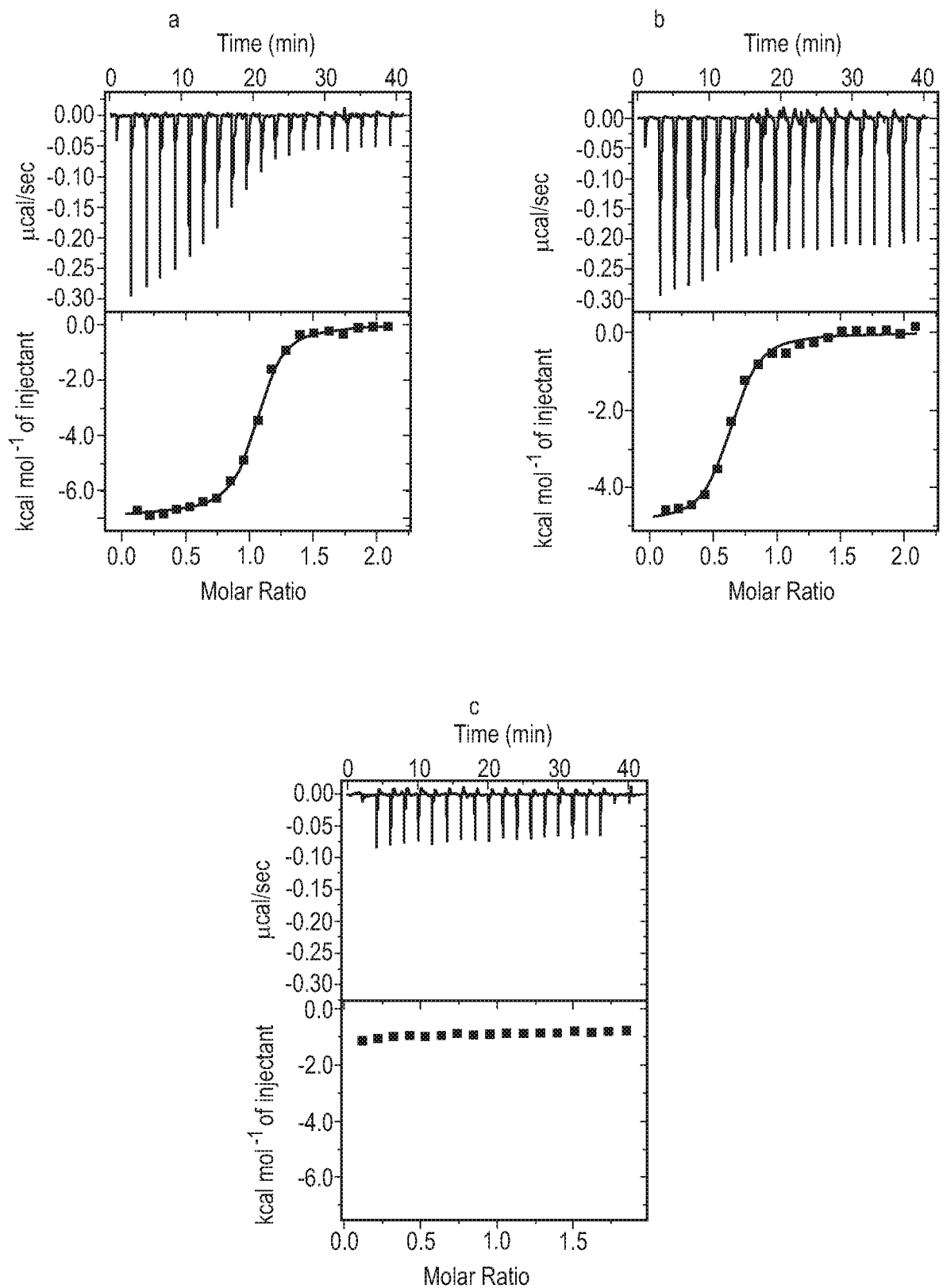
FIG. 15a: illustrates isothermal titration calorimetry (ITC) plots obtained over time from treatment of MZ1 against VBC.
FIG. 15b: illustrates isothermal titration calorimetry (ITC) plots obtained over time from treatment of MZ3 against VBC.
FIG. 15c: illustrates isothermal titration calorimetry (ITC) plots obtained over time from treatment of cisMZ1 against VBC.

Whilst not wishing to be bound to any particular theory it is proposed herein that such differences observed in gene modulation may be the result of preferential degradation of BRD4 over the other two BET proteins caused by MZ1. To test this hypothesis, experiments were carried out to suppress individual BRD2, BRD3 or BRD4 genes using siRNA to mimic the protein removal effect. These results are illustrated in FIG. 13, and analysis of the gene expression level of the target genes of interest was carried out, as illustrated in the results presented in FIG. 4b. While MYC, P21 and AREG levels were confirmed to be affected by suppression of BRD4, these experiments confirmed that FAS was down-regulated upon suppression of BRD2 only, but not BRD4 (as illustrated in FIG. 4b) while FGFR1 is up-regulated upon suppression of either BRD3 or BRD4.

These results are consistent with preferential degradation of BRD4 over BRD2 and BRD3 by a PROTAC of structure A-L-B, MZ1 and point to a more BRD4-selective pharmacological profile for PROTACs of structure A-L-B in accordance with the present invention in comparison to the pan-selective inhibitor JQ1.

PROTAC compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a PROTAC compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a PROTAC compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present invention comprise a therapeutically effective amount of a PROTAC compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type.

The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the PROTAC compounds of the invention with suitable non-irritating excipients or carriers such as cocoa butter, polyethylene glycol or a suppository wax which are solid at ambient temperature but liquid at body temperature and therefore melt in the rectum or vaginal cavity and release the active compound. Solid compositions of a similar type may also be employed as fillers in soft and hard-filled gelatine capsules using such excipients as lactose or milk sugar as well as high molecular weight polyethylene glycols and the like.

The PROTAC compounds can also be provided in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the PROTAC compounds of this invention, excipients such as lactose, talc, silicic acid, aluminium hydroxide, calcium silicates and polyamide powder, or mixtures of these substances. Sprays can additionally contain customary propellants such as chlorofluorohydrocarbons. Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, diseases, conditions, or disorders are treated or prevented in a subject, such as a human or other animal, by administering to the subject a therapeutically effective amount of a PROTAC compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a PROTAC compound of this invention will be at a reasonable benefit/risk ratio applicable to any medical treatment.

The dosage for the instant compounds can vary according to many factors, including the type of disease, the age and general condition of the patient, the particular compound administered, and the presence or level of toxicity or adverse effects experienced with the drug. A representative example of a suitable dosage range is from as low as about 0.025 mg to about 1000 mg. However, the dosage administered is generally left to the discretion of the physician.

A wide variety of pharmaceutical dosage forms for mammalian patients can be employed. If a solid dosage is used for oral administration, the preparation can be in the form of a tablet, hard gelatin capsule, troche or lozenge. The amount of solid carrier will vary widely, but generally the amount of the PROTAC compound will be from about 0.025 mg to about 1 g, with the amount of solid carrier making up the difference to the desired tablet, hard gelatin capsule, troche or lozenge size. Thus, the tablet, hard gelatin capsule, troche or lozenge conveniently would have, for example, 0.025 mg, 0.05 mg, 0.1 mg, 0.5 mg, 1 mg, 5 mg, 10 mg, 25 mg, 100 mg, 250 mg, 500 mg, or 1000 mg of the present compound. The tablet, hard gelatin capsule, troche or lozenge is given conveniently once, twice or three times daily.

In general, PROTAC compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents. Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms. It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for pharmaceutical combinations, e.g. a kit, comprising a) a first agent which is a PROTAC compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a PROTAC compound of the invention and a co-agent, are both administered to a patient simultaneously in the form of a single entity or dosage. The term "non-fixed combination" means that the active ingredients, e.g. a PROTAC compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminium hydroxide; alginic acid; pyrogen-free water, isotonic saline; Ringer's solution; ethyl alcohol, and phosphate buffer solutions, as well as other non-toxic compatible lubricants such as sodium lauryl sulphate and magnesium stearate, as well as colouring agents, releasing agents, coating agents, sweetening, flavouring and perfuming agents, preservatives and antioxidants can also be present in the composition, according to the judgment of the formulator.

Biological Results

As detailed herein, PROTAC compounds of the present invention have been demonstrated to induce degradation of BET proteins. Table 1 shows, as examples, some of the protein abundance data for some of the PROTAC compounds of the present invention. The in vitro data presented in Table 1 confirms the efficacy of PROTAC compounds of the present invention for the potent and effective degradation of BET proteins, as well as their preferential degradation effect on BRD4 over BRD2 and BRD3.

TABLE 1

| Example PROTAC | Purified Protein | $K_d$ [nM] | $\Delta H$ [kcal/mol] | $\Delta S$ [cal/mol-K] | $\Delta G$ [kcal/mol] |
|---|---|---|---|---|---|
| MZ1 (MZP-22) | BRD2/BD1 | 307 ± 27.9 | −10.0 ± 0.1 | −4.29 ± 0.38 | −9.05 ± 0.06 |
| MZ1 (MZP-22) | BRD2/BD2 | 228 ± 17.7 | −6.08 ± 0.04 | 10.3 ± 0.2 | −9.22 ± 0.05 |
| MZ1 (MZP-22) | BRD3/BD1 | 119 ± 4.81 | −10.0 ± 0.06 | −4.40 ± 0.20 | −9.62 ± 0.02 |
| MZ1 (MZP-22) | BRD3/BD2 | 115 ± 10.9 | −8.32 ± 0.05 | −4.29 ± 0.26 | −9.63 ± 0.06 |
| MZ1 (MZP-22) | BRD4/BD1 | 382 ± 13.5 | −8.59 ± 0.03 | 1.04 ± 0.13 | −8.91 ± 0.02 |
| MZ1 (MZP-22) | BRD4/BD2 | 120 ± 7.16 | −6.86 ± 0.03 | 9.04 ± 0.16 | −9.61 ± 0.04 |
| MZ3 (MZP-24) | VBC | 311 ± 51.2 | −4.90 ± 0.11 | 13.4 ± 0.49 | −9.04 ± 0.10 |
| cisMZ1(MZP-42) | | no binding | no binding | no binding | no binding |

The Applicant has carried out biological testing of further PROTAC compounds of structure A-L-B having alternative B-groups and has found activity profiles consistent with those discussed herein in relation to the test results obtained for PROTAC compounds of structure A-L-B having a JQ1-based B-group.

Chemistry—Materials and Methods

NMR spectra were recorded on a Bruker 500 Ultrashield or a Bruker Ascend 400. Chemical shifts are quoted in ppm and referenced to the residual solvent signals: $^1$H δ=7.26 (CDCl$_3$), $^{13}$C δ=77.16 (CDCl$_3$).

High Resolution Mass Spectra (HRMS) were recorded on a Bruker micrOTOF. All chemicals, unless otherwise stated were commercially available and used without further purification. Enantiopure (+)-JQ-1 was purchased from Medchemexpress LLC, Princeton, USA. Flash column chromatography was performed using a Teledyne Isco Combiflash Rf or Rf200i. As prepacked columns RediSep Rf Normal Phase Disposable Columns were used. Preparative HPLC was performed on a Gilson Preparative HPLC System with a Waters X-Bridge C18 column (100 mm×19 mm; 5 µm particle size) and with a gradient of 20% to 95% acetonitrile in water with 0.1% ammonia in the aqueous phase.

Isothermal Titration Calorimetry

Titration was performed at 30° C. with protein concentration of 15 μM and ligand concentration of 150 μM (entry 1-6). Titration of MZ1 and cisMZ1 into VBC at 25° C. with identical concentrations (see entries 9 and 12 in FIG. 1), whilst reverse titration of VBC protein (150 μM) into MZ3 (15 μM) at 25° C. were conducted (see entry 10 in FIG. 1).

General Procedure for Synthesis of Compounds of Formula I (A-Groups)

Any compounds of formula I as defined herein can be prepared in accordance with the general methodology in Scheme 3 by selection of the appropriate reagents at the following stages: choice of C— or N-5 membered ring, and selection of the substituents thereon at stage (iii); choice of Y-group at stage (iv).

and wherein $R^{2b}$ is H, or wherein $R^{2a}$ and $R^{2b}$ are both F then the relevant alternative commercially available material can be used either in de-protected or protected form, in accordance with the methodology described herein. Exemplary commercially available materials suitable for such use include: 2-trifluoromethyl; 2-fluoroproline; 2,2-difluoroproline; and 2-aminoproline. As will also be appreciated further reagents suitable for use in step (iii) can be readily prepared from hydroxylproline, or from one or other commercially available alternatives, for example, 2-aminoproline (where $R^{2a}$ is —NH$_2$ and $R^{2b}$ is H) in the final compound can be made starting from hydroxyl proline.

A general method for Boc-deprotection is provided in Scheme 4 herein.

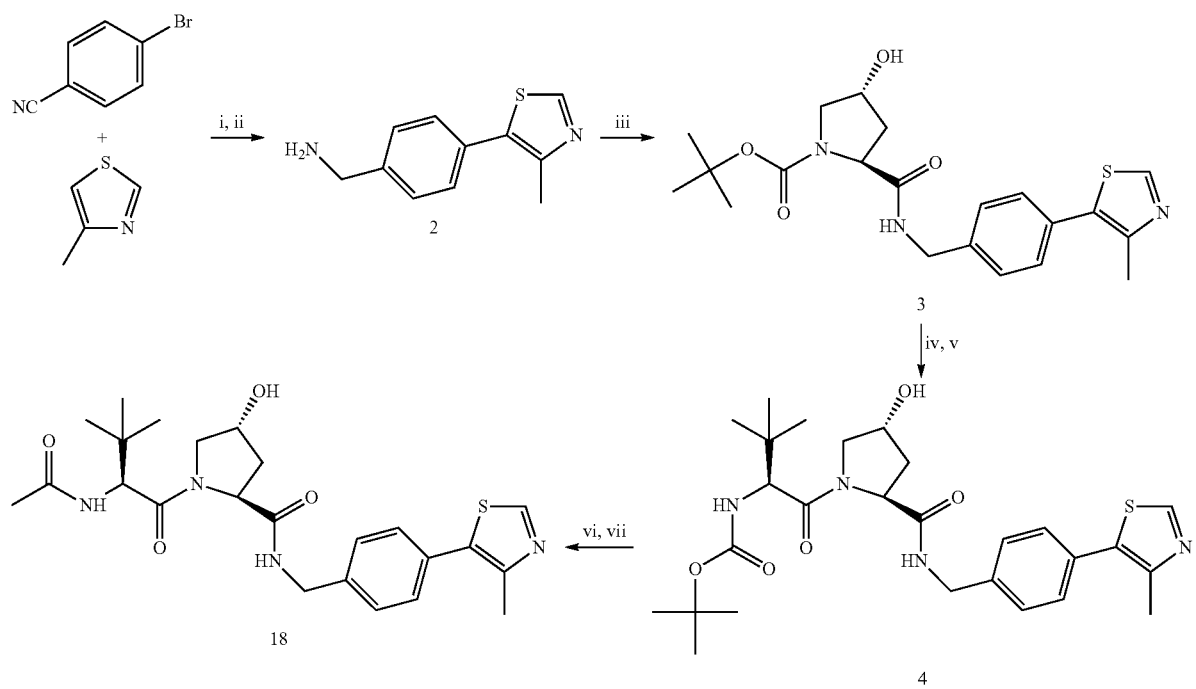

Scheme 3

The conditions used for the exemplary preparation in Scheme 3 are as follows: (i) Pd(OAc)$_2$, KOAc, DMAc, reflux, O/N; (ii) NaBH$_4$, CoCl$_2$, MeOH, 0° C., 90 min; (iii) Boc-Hyp-OH, DIPEA, HATU, DMF, rt, 30 min; (iv) TFA/DCM 1:1, rt, 30 min; (v) Boc-L-tert-leucine, DIPEA, HATU, DMF, room temperature, 30 min; (vi) TFA/DCM 1:1, room temperature, 30 min; (vii) acetic anhydride, N(Et)$_3$, DCM, room temperature, 90 min.

As will be appreciated by the skilled chemist, using the general procedures indicated in Scheme 3, and via selection of the appropriate starting materials and using the methodology provided for the preparation of Boc-protected compounds (4) and (5) any Boc-protected amine suitable for use in the preparation of compounds of formula I, or any compound of formula IA as defined herein can be prepared.

In particular in step (iii) the use of alternative reagents, such as for example to provide alternative final compounds having different $R^{2a}$ and/or $R^{2b}$ groups, to that provided in the above example using hydroxyproline in step (iii), such as for example compounds wherein $R^{2a}$ is —NH$_2$, F, or —CF$_3$ (4-(4-Methylthiazol-5-yl)phenyl)methanamine (2)

To a solution of 4-bromobenzonitrile (1.5 g, 8.24 mmol, 1 equiv.) and Pd(OAc)$_2$ (2 mg, 0.08 mmol, 0.1 mol %) in DMAc (8 mL) were added KOAc (1.62 g, 16.5 mmol, 2 equiv.) and 4-methylthiazole (1.63 g, 1.49 mL, 16.5 mmol, 2 equiv.). The resulting mixture was heated to 150° C. and stirred overnight. The mixture was diluted with water and extracted with DCM (3x). The combined organic phases were dried over MgSO$_4$ and evaporated under reduced pressure to give the corresponding cyano derivate as a beige solid (1.67 g, 7.99 mmol, 97%) that matched the reported spectral data. A solution of the cyano-derivate product (270 mg, 1.3 mmol, 1 equiv.) in methanol (15 mL) was cooled to 0° C. CoCl (282 mg, 2.2 mmol, 1.5 equiv.) was added, followed by portion-wise addition of NaBH$_4$ (274 mg, 7.2 mmol, 5 equiv.). The resulting mixture was stirred for 90 min, the reaction was quenched with water and ammonium hydroxide, and the mixture was extracted with chloroform (6x). The combined organic phases were dried over MgSO$_4$ and evaporated under reduced pressure to give a dark-brown oil which was purified by flash column chromatography to yield the desired product, preparative compound (4) as a yellow oil (76.5 mg, 0.40 mmol, 29% (isolated)) that matched the reported spectral data.

(2S,4R)-tert-Butyl-4-hydroxy-2-((4-(4-methyl thiazol-5-yl)benzyl)-carbamoyl)pyrrolidine-1-carboxylate (3)

To a solution of preparative compound (2) (340 mg, 1.66 mmol, 1 equiv.) in DMF was added Boc-Hyp-OH (383 mg, 1.66 mmol, 1 equiv.) and the solution was stirred at room temperature. DIPEA (4 equiv.) was added drop-wise, and the mixture was stirred for 5 min at room temperature. HATU (1.1 equiv.) was added, and the mixture was stirred at room temperature for another 30 min. Water was added, and the mixture was extracted with ethyl acetate (3x). The combined organic phases were washed with brine (×2), dried over MgSO$_4$, and evaporated under reduced pressure to give the corresponding crude, which was purified by flash column chromatography purification to yield desired preparative compound (3) as a yellow solid (658 mg, 1.58 mmol, 95%) that matched the reported spectral data. MS (ESI): [M+1] calculated 418.2; observed 418.2.

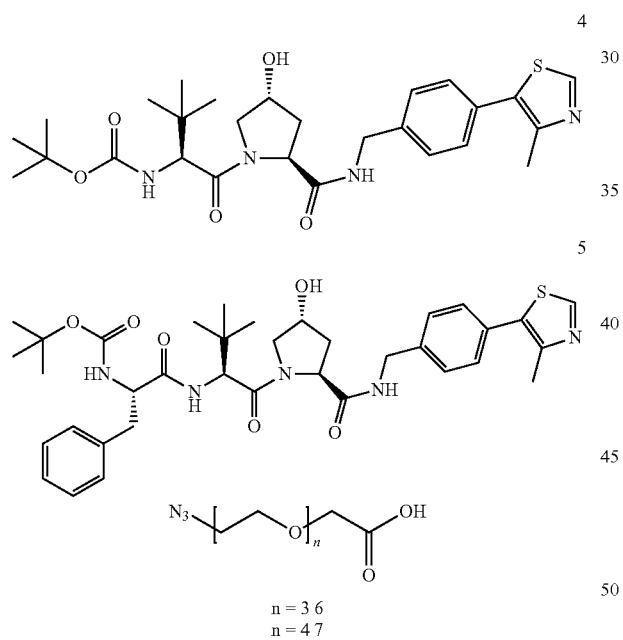

tert-Butyl((S)-1-((2S,4R)-4-hydroxy-2-((4-(4-methylthiazole-5-yl)-benzyl)carbamoyl)pyrrolidin-1-yl)-3,3-dimethyl-1-oxobutan-2-yl)-carbamate (4)

A solution of (2S,4R)-tert-Butyl-4-hydroxy-2-((4-(4-methyl thiazol-5-yl)benzyl)-carbamoyl)pyrrolidine -1-carboxylate, prepared in accordance with the general methodology indicated above, (340 mg, 0.81 mmol) in 1:1 TFA:DCM (8 mL) was stirred at room temperature for 30 min. The mixture was evaporated under reduced pressure to give the corresponding deprotected intermediate (TFA salt) as a brown oil without further purification (330 mg, 0.77 mmol, 98%). Following the general method A, from the deprotected intermediate (330 mg, 0.77 mmol, 1 equiv) and Boc-L-tert-leucine (178 mg, 0.77 mmol, 1 equiv), compound (4) was obtained as a yellow solid (400 mg, 0.75 mmol, 98%), which was used directly for the next step. MS (ESI): [M+1] calculated 531.3; observed 531.3.

tert-butyl-((S)-1-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)amino)-1-oxo-3-phenylpropan-2-yl)carbamate (5)

To a solution of compound (4) (1.2 g, 2.26 mmol) in 1:1 TFA:DCM (20 mL) was stirred at room temperature for 30 min. The mixture was evaporated under reduced pressure to give the corresponding intermediate (TFA salt), part of which was used directly for the next step. To a solution of the resulting deprotected amine (TFA salt, 419 mg, 0.77 mmol, 1 eq.) in DMF was added Boc-L-phenylalanine (204 mg, 0.77 mmol, 1 eq.), and the solution was stirred at room temperature. DIPEA (4 equiv) was added dropwise, and the mixture was stirred for 5 min at room temperature. HATU (1.1 equiv) was added, and the mixture was stirred at room temperature for another 30 min. Water was added, and the mixture was extracted with ethyl acetate (×3). The combined organic phases were washed with brine (×2), dried over MgSO$_4$, and evaporated under reduced pressure to give the corresponding crude, which was purified by flash column chromatography purification to yield the final compound (5) as brown solid (492 mg, 0.73 mmol, 94%).

tert-butyl(2S,4S)-4-hydroxy-2-((4-(4-methylthiazol-5-yl)benzyl)carbamoyl)pyrrolidine-1-carboxylate (8)

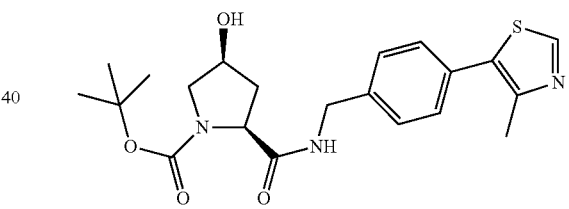

To a solution of (4-(4-methylthiazol-5-yl)phenyl)methanamine (500 mg, 2.43 mmol, 1 eq.) in DCM was added (2S,4S)-1-(tert-butoxycarbonyl)-4-hydroxypyrrolidine-2-carboxylic acid (565 mg, 2.43 mmol, 1 eq.) and 1-[Bis (dimethylamino)methylene]-1H-1,2,3-triazolo[4,5-b]pyridinium-3-oxidhexafluoro phosphate (HATU) (827 mg, 2.68 mmol, 1.1 eq.). After the pH of the reaction was adjusted to >9 by addition of N,N-diisopropylethyl amine (1.70 ml, 9.72 mmol, 4 eq.) the reaction was stirred for 2 h at 25° C. The reaction mixture was washed with water and the organic phase then dried over MgSO$_4$. After removing the solvent in vacuum the residue was purified by flash column chromatography using a gradient of 10% to 70% Acetone in Hexane. Yield: 587 mg (58%); $^1$H-NMR (CDCl$_3$, 400 MHz) 1.45 (s, 9H), 2.14-2.23 (m, 1H), 2.34-2.39 (m, 1H), 2.51 (s, 3H), 3.44-3.53 (m, 2H), 4.40-4.46 (m, 4H), 4.58 (dd, 1H, J(H,H)=7.08 Hz, J(H,H)=14.9 Hz), 7.32-7.39 (m, 4H), 7.51-7.54 (m, 1H), 8.67 (s, 1H); $^{13}$C-NMR (CDCl$_3$, 101 MHz) δ 12.7, 28.4, 35.9, 55.9, 57.2, 59.7, 70.9, 81.0, 127.8, 129.7, 131.2, 137.7, 148.7, 150.4, 155.9, 162.8, 173.5; HRMS m/z calc. for C$_{21}$H$_{28}$N$_3$O$_4$S [M+H$^+$] 418.1795, found 418.1786.

tert-butyl ((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)carbamate (9)

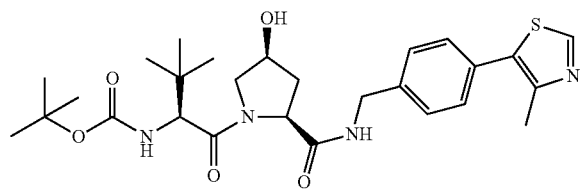 [SMILES: Cc1ncsc1-c1ccc(CNC(=O)[C@@H]2C[C@H](O)CN2C(=O)[C@@H](NC(=O)OC(C)(C)C)C(C)(C)C)cc1]

Compound (8) was boc-deprotected as described below to obtain 8*TFA. 8*TFA (604 mg, 1.40 mmol, 1 eq.) and (S)-2-((tert-butoxycarbonyl)amino)-3,3-dimethylbutanoic acid (324 mg, 1.40 mmol, 1 eq.) were dissolved in DCM (100 ml). After addition of HATU (798 mg, 2.10 mmol, 1.5 eq.) the pH was adjusted to >9 by addition of N,N-Diisopropylethyl amine (978 µl, 5.60 mmol, 4 eq.) and the reaction stirred at 25° C. for 2 h. The reaction mixture was then washed with water and the remaining organic phase dried over magnesium sulfate. After removing the solvent in vacuum the residue was purified by flash column chromatography using a gradient of 10% to 60% Acetone in Hexane. Yield: 300 mg (40%); $^1$H-NMR (CDCl$_3$, 400 MHz) δ 0.90 (s, 9H), 1.41 (s, 9H), 2.16-2.23 (m, 1H), 2.36-2.40 (m, 1H), 2.52 (s, 3H), 3.78-3.91 (m, 2H), 4.18 (d, 1H, J(H,H)= 8.35 Hz), 4.29 (dd, 1H, J(H,H)=5.08 Hz, J(H,H)=14.9 Hz), 4.48 (s, 1H), 4.64 (dd, 1H, J(H,H)=7.08 Hz, J(H,H)=14.9 Hz), 4.77 (d, 1H, J(H,H)=8.84 Hz), 5.12 (d, 1H, J(H,H)= 8.96 Hz), 5.56 (s, 1H), 7.33-7.39 (m, 4H), 7.52-7.56 (m, 1H), 8.69 (s, 1H); $^{13}$C-NMR (CDCl$_3$, 101 MHz) δ 14.3, 16.1, 22.8, 26.4, 28.5, 32.0, 35.1, 58.5, 58.7, 60.0, 71.2, 80.0, 128.3, 129.8, 131.4, 131.7, 137.4, 148.6, 150.6, 155.8, 172.7, 173.0; HRMS m/z calc. for $C_{27}H_{39}N_4O_5S$ [M+H$^+$] 531.2636, found 531.2660.

General Procedure for Boc-Deprotection: Steps vi, vii in Scheme 3

Scheme 4 illustrates a method for the de-protection of various intermediate Boc-protected amines (4), (5), (9), (10), (11) and (12) which are suitable for use in the preparation of compounds of formula I wherein X=N, the R$^1$ to R$^5$ groups are specified and wherein Y can be (i) or (ii). For the avoidance of doubt, any intermediate Boc-protected amine suitable for use in the preparation of compounds of formula I, and prepared in accordance with the methods indicated at stages (i) to (v) in Scheme 3 can be deprotected to furnish a compound of formula I (an A-group) in accordance with the following procedure.

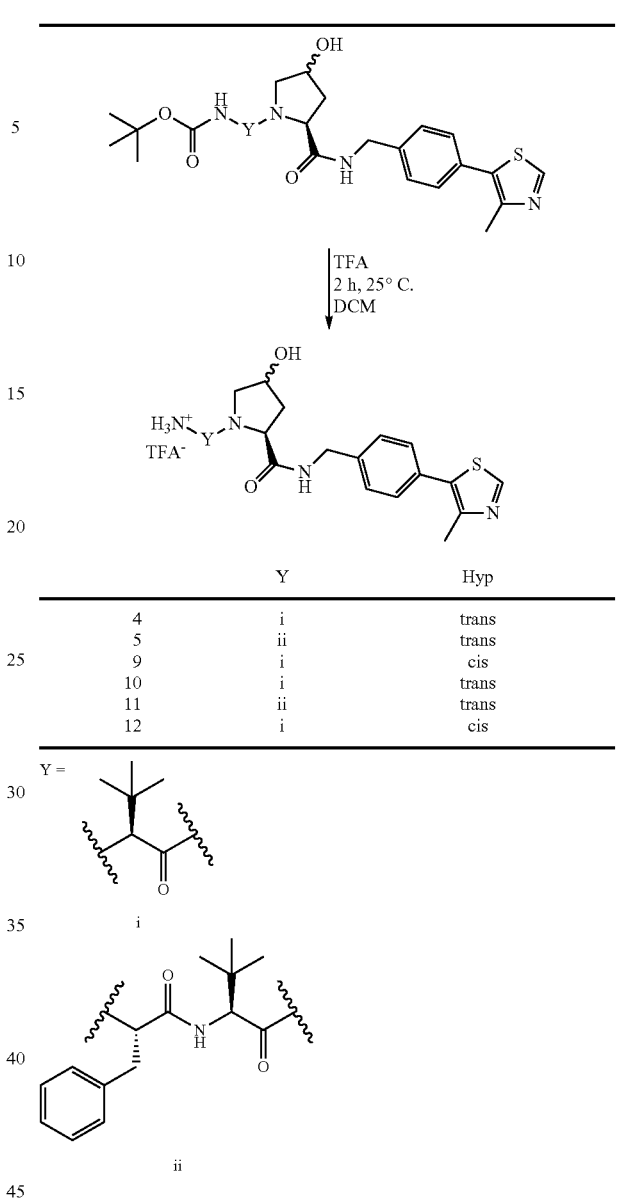

| | Y | Hyp |
|---|---|---|
| 4 | i | trans |
| 5 | ii | trans |
| 9 | i | cis |
| 10 | i | trans |
| 11 | ii | trans |
| 12 | i | cis |

The N-Boc-protected compound was dissolved in dichloromethane (10 ml/1 mmol). Trifluoroacetic acid (10 ml/1 mmol) was added and the reaction mixture stirred at room temperature for 2 h. The solvent was removed under reduced pressure. For three times dichloromethane (5 ml/1 mmol) was added and then the solvent again removed in vacuum to remove residual trifluoroacetic acid.

Synthesis of Azide-Linker Groups (Az-L)

Scheme 5

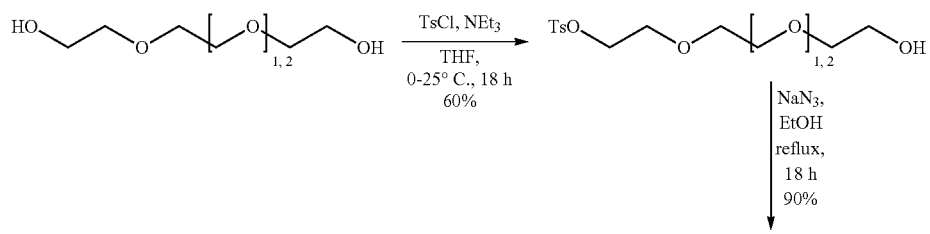

-continued

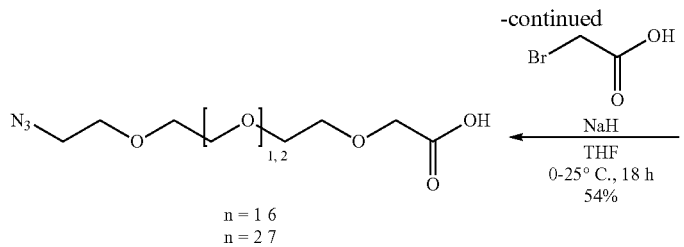

n = 1 6
n = 2 7

Any azide-linker suitable for use in the preparation of an intermediate compound of formula II as defined herein can be prepared in accordance with the general methodology outlined in Scheme 5 for the preparation of azide-linker compounds (6) and (7) by selection of the appropriate starting material.

Compound (6) was Synthesized Starting from Triethylene Glycol.

Tri-ethylene glycol (120 mmol, 3 eq.) was dissolved in anhydrous THF (80 ml) and triethylamine (80 mmol, 2 eq.) was added. At 0° C. p-toluenesulfonyl chloride (40 mmol, 1 eq.) in anhydrous THF (10 ml) was added dropwise over 45 min. The reaction mixture was allowed to warm to room temperature and stirred overnight. The solvent was then removed in vacuo and the crude mixture purified by flash column chromatography using a gradient from 30%-90% Ethyl acetate in heptane.

The tosylates (20 mmol, 1 eq.) were dissolved in ethanol, sodium azide (40 mmol, 2 eq.) was added and the reaction mixture heated to reflux for 18 h. After cooling to room temperature the solvent was removed in vacuo and the residue dissolved in water. The aqueous phase was extracted three times with dichloromethane. The organic phase was then dried over magnesium sulphate and then the solvent removed in vacuo.

At 0° C. to the solution of the azides (10 mmol, 1 eq.) dissolved in anhydrous THF (25 ml) sodium hydride (20 mmol, 2 eq.) was added and the reaction mixture stirred for 45 min. Bromoacetic acid (10 mmol, 1 eq.) in anhydrous THF (25 ml) was then added and the reaction mixture allowed to warm to room temperature and stirred for 18 h. The solvent was removed in vacuo, the residue acidified to pH 2 with 1 M hydrochloric acid and the aqueous phase extracted for three times with dichloromethane. The combined organic layers were dried over magnesium sulphate and then purified by flash column chromatography using 10% methanol in dichloromethane to obtain the title compound (6).

Compound (7) was synthesized in accordance with the method provided for compound (6) and starting from tetra-ethylene glycol.

General Procedure for Coupling a to Az-L to Provide Intermediate Azide of Formula II:

As outlined in Scheme 1, the starting amine, for example preparative compounds (10), (11) or (12) (1 mmol, 1 eq.) was added to a solution of the desired linker, for example Az-PEG-linkers (6) or (7) (1.2 mmol, 1.2 eq.) in DCM (40 ml). HATU (570 mg, 1.5 mmol, 1.5 eq.) was added and the pH adjusted to >9 by addition of DIPEA (700 µl, 4 mmol, 4 eq.). After stirring for 4 h at 25° C. the reaction mixture was extracted with water. The organic phase was dried over Magnesium sulfate and evaporated to dryness. The crude product was purified by flash column chromatography using a gradient of 0%-6% of Methanol in Dichloromethane to furnish the desired intermediate azide of structure Az-L-A.

General Procedure for Coupling a to an Az-L Group, Starting from an N-Boc Protected A-Group The N-boc-protected compound, for example preparative compounds (4), or (5), was dissolved in dichloromethane (10 ml/1 mmol). Trifluoroacetic acid (10 ml/1 mmol) was added and the reaction mixture stirred at room temperature for 2 h. The solvent was removed under reduced pressure. For three times dichloromethane (5 ml/1 mmol) was added and then the solvent again removed in vacuum to remove residual trifluoroacetic acid. The resulting TFA ammonium salts (1 mmol, 1 eq.) were added to a solution of Az-PEG-linker (1.2 mmol, 1.2 eq.) in DCM (40 ml). HATU (570 mg, 1.5 mmol, 1.5 eq.) was added and the pH adjusted to >9 by addition of DIPEA (700 µl, 4 mmol, 4 eq.). After stirring for 4 h at 25° C. the reaction mixture was extracted with water. The organic phase was dried over Magnesium sulfate and evaporated to dryness. The crude product was purified by flash column chromatography using a gradient of 0%-6% of methanol in dichloromethane.

Azides (13), (14), (15), (16), MZP-59, MZP-12, MZP-9, MZP-20, and MZP-39 as detailed herein were prepared in accordance with the above general methodology from the appropriate starting amine or protected amine and the appropriate Az-PEG linker.

(2S,4R)-1-((S)-14-azido-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide
(13)

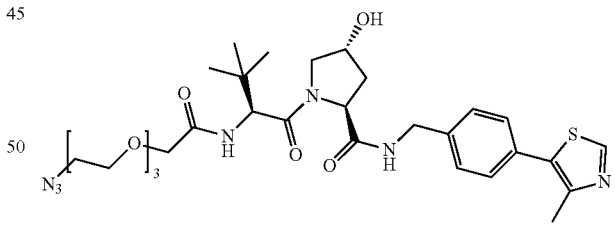

Yield: 491 mg (76%); $^1$H-NMR (CDCl$_3$, 500 MHz) δ 0.95 (s, 9H), 2.09-2.14 (m, 1H), 2.52 (s, 3H), 2.58-2.63 (m, 1H), 2.85 (s, 1H), 3.37 (t, 2H, J(H,H)=10.1 Hz), 3.60 (dd, 1H, J(H,H)=3.63 Hz, J(H,H)=11.4 Hz), 3.64-3.69 (m, 10H), 3.96-4.05 (m, 2H), 4.12-4.14 (m, 1H), 4.34 (dd, 1H, J(H,H)=5.20 Hz, J(H,H)=14.9 Hz), 4.46 (d, 1H, J(H,H)=8.35 Hz), 4.53-4.59 (m, 2H), 4.75 (t, 1H, J(H,H)=7.88 Hz), 7.27 (s, 1H), 7.33-7.38 (m, 5H), 8.67 (s, 1H); $^{13}$C-NMR (CDCl$_3$, 126 MHz) δ 16.2, 26.6, 34.8, 35.7, 43.5, 50.9, 56.7, 57.4, 58.4, 70.2, 70.3, 70.5, 70.7, 70.8, 70.9, 71.3, 128.4, 129.7, 131.2, 131.7, 138.2, 148.7, 150.4, 170.6, 170.8, 171.8; HRMS m/z calc. for C$_{30}$H$_{44}$N$_7$O$_7$S [M+H$^+$] 646.3017, found 646.3023.

(2S,4R)-1-((S)-17-azido-2-(tert-butyl)-4-oxo-6,9,12, 15-tetraoxa-3-azaheptadecanoyl)-4-hydroxy-N-(4-(4-methylthiazol-5-yl)benzyl)pyrrolidine-2-carboxamide (14)

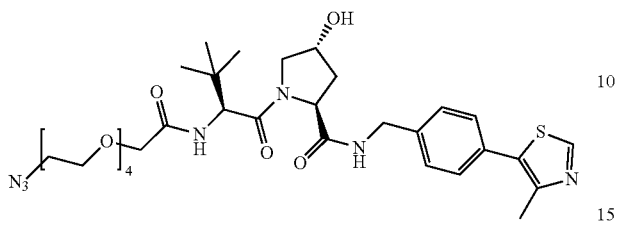

Yield: 607 mg (88%); $^1$H-NMR (CDCl$_3$, 500 MHz) δ 0.95 (s, 9H), 2.10-2.15 (m, 1H), 2.51-2.58 (m, 4H), 2.96 (d, 1H, J(H,H)=3.00 Hz), 3.39-3.41 (m, 2H), 3.60-3.67 (m, 15H), 3.97-4.05 (m, 2H), 4.07-4.09 (m, 1H), 4.35 (dd, 1H, J(H,H)=5.33 Hz, J(H,H)=14.9 Hz), 4.49 (d, 1H, J(H,H)=8.50 Hz), 4.53-4.57 (m, 2H), 4.73 (t, 1H, J(H,H)=7.90 Hz), 7.15 (d, 1H, J(H,H)=8.45 Hz), 7.30-7.38 (m, 5H), 8.68 (s, 1H); $^{13}$C-NMR (CDCl$_3$, 126 MHz) δ 16.2, 26.5, 26.6, 35.0, 35.9, 43.4, 50.8, 56.8, 57.3, 58.5, 70.2-71.3, 128.3, 129.7, 131.1, 131.8, 138.3, 148.6, 150.5, 170.7, 170.8, 171.6; HRMS m/z calc. for C$_{32}$H$_{48}$N$_7$O$_8$S [M+H$^+$] 690.3280, found 690.3308.

(2S,4R)-1-((2S,5S)-17-azido-5-benzyl-2-(tert-butyl)-4,7-dioxo-9,12,15-trioxa-3,6-diazaheptadecanoyl)-4-hydroxy-N-(4-(4-methylthiazol-5-yl)benzyl)pyrrolidine-2-carboxamide (15)

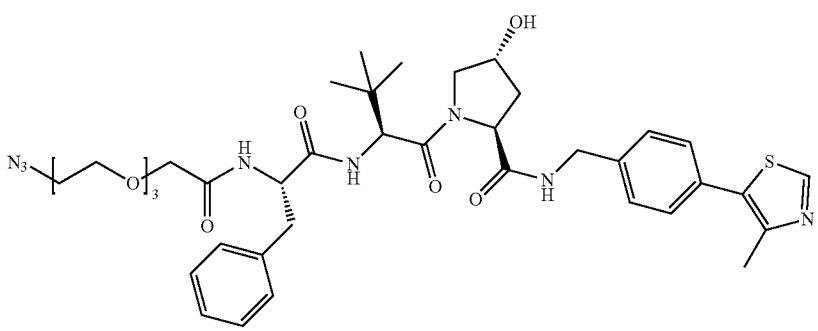

Yield 642 mg (81%); $^1$H-NMR (CDCl$_3$, 500 MHz) δ 0.89 (s, 9H), 2.12-2.16 (m, 1H), 2.51-2.56 (m, 4H), 2.97-3.01 (m, 2H), 3.09-3.14 (m, 1H), 3.33-3.37 (m, 2H), 3.51-3.65 (m, 12H), 3.89-3.92 (m, 2H), 3.99-4.01 (m, 1H), 4.34 (dd, 1H, J(H,H)=5.18 Hz, J(H,H)=14.9 Hz), 4.42-4.47 (m, 1H), 4.50-4.54 (m, 2H), 4.64-4.70 (m, 1H), 4.74 (t, 1H, J(H,H)=7.80 Hz), 7.01-7.09 (m, 1H), 7.15-7.24 (m, 4H), 7.31-7.37 (m, 5H), 7.43-7.48 (m, 1H), 8.67 (s, 1H); $^{13}$C-NMR (CDCl$_3$, 126 MHz) δ 16.2, 26.6, 35.6, 36.5, 37.5, 43.3, 50.7, 54.0, 56.9, 58.0, 58.7, 70.1-71.1, 127.0, 128.2, 128.7, 129.4, 129.6, 131.0, 131.7, 136.4, 138.2, 148.5, 150.4, 170.6, 171.1, 171.1, 171.3; HRMS m/z calc. for C$_{39}$H$_{52}$N$_8$O$_8$S [M+H$^+$] 793.3702, found 793.3707.

(2S,4S)-1-((S)-14-azido-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (16)

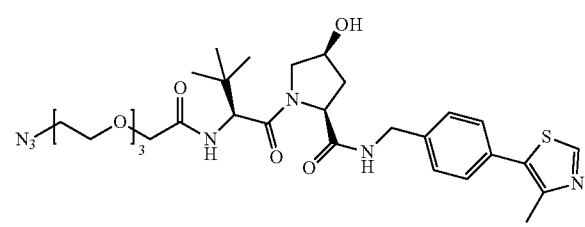

Yield 194 mg (30%); $^1$H-NMR (CDCl$_3$, 400 MHz) δ 0.93 (s, 9H), 2.14-2.21 (m, 1H), 2.35-2.39 (s, 1H), 2.52 (s, 3H), 3.36 (t, 2H, J(H,H)=5.08 Hz), 3.63-3.68 (m, 10H), 3.79-3.82 (m, 1H), 3.91-3.95 (m, 1H), 3.95-4.05 (m, 2H), 4.30 (dd, 1H, J(H,H)=5.06 Hz, J(H,H)=14.90 Hz), 4.45-4.50 (m, 1H), 4.53 (d, 1H, J(H,H)=9.16 Hz), 4.64 (dd, 1H, J(H,H)=7.08 Hz, J(H,H)=14.88 Hz), 4.74 (d, 1H, J(H,H)=8.96 Hz), 5.53 (d, 1H, J(H,H)=9.92 Hz), 7.18 (d, 1H, J(H,H)=9.05 Hz), 7.33-7.39 (m, 4H), 7.50-7.53 (m, 1H), 8.68 (s, 1H); $^{13}$C-NMR (CDCl$_3$, 101 MHz) δ 16.2, 26.4, 35.1, 35.2, 43.7, 50.8, 56.6, 58.8, 60.0, 70.2-71.3, 128.3, 129.8, 131.4, 131.6, 137.5, 148.7, 150.5, 169.9, 172.0, 172.7; HRMS m/z calc. for C$_{30}$H$_{44}$N$_7$O$_7$S [M+H$^+$] 646.3017, found 646.3040.

(2S,4R)-1-((S)-2-Acetamido-3,3-dimethylbutanoyl)-4-hydroxy-N-(4-(4-methylthiazol-5-yl) benzyl)pyrrolidine-2-carboxamide (18)

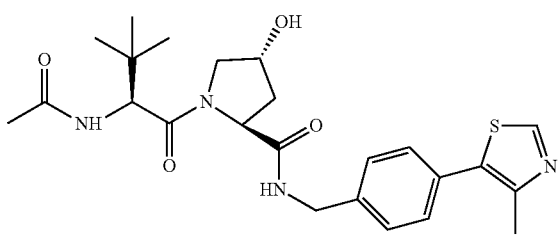 [SMILES: CC(=O)N[C@H](C(=O)N1C[C@H](O)C[C@H]1C(=O)NCc1ccc(-c2scnc2C)cc1)C(C)(C)C]

A solution of ligand, preparative compound (4) (257 mg, 0.48 mmol) in 1:1 TFA:DCM (5 mL) was stirred at room temperature for 30 min. The mixture was evaporated under reduced pressure to give the corresponding intermediate (TFA salt), which was used directly for the next step. The TFA salt, (275 mg, 0.50 mmol, 1 equiv) was dissolved in DCM, and triethylamine (3 equiv) was added to the solution. After stirring the mixture for 10 min at room temperature, acetic anhydride (1.5 equiv) was added and the reaction was stirred 90 min at room temperature. The solvents were evaporated under reduced pressure to give the corresponding crude, which was purified by flash column chromatography to yield the desired compound (7) as a colorless oil (65.3 mg, 0.14 mmol, 27%). $^1$H NMR (CDCl$_3$, 500 MHz): δ 8.67 (s, 1H), 7.35 (dd, J=15.0, 10.0 Hz, 4H), 4.71 (t, J=10.0 Hz, 1H), 4.56-4.48 (m, 3H), 4.33 (dd, J=15.0, 10.0, 1H), 4.07 (d, J=10 Hz, 1H), 3.60 (dd, J=10.0, 5.0 Hz, 1H), 2.60 (s, 2H), 2.50 (s, 3H), 2.14-2.10 (m, 1H), 1.98 (s, 3H), 0.93 (s, 9H). $^{13}$C NMR (CDCl$_3$, 125 MHz): δ 172.1, 170.9, 170.8, 150.4, 148.7, 138.2, 131.8, 131.2, 129.7, 128.3, 70.2, 58.6, 57.7, 56.8, 45.7, 43.2, 36.0, 35.0, 26.5, 8.6. HRMS (ESI) m/z:[M+1] calculated for C$_{24}$H$_{33}$N$_4$O$_4$S: 473.2222; observed 473.2211.

(2S,4R)-1-((S)-2-(2-(2-(2-azidoethoxy)ethoxy)acetamido)-3,3-dimethylbutanoyl)-4-hydroxy-N-(4-(4-methylthiazol-5-yl)benzyl)pyrrolidine-2-carboxamide (MZP-59)

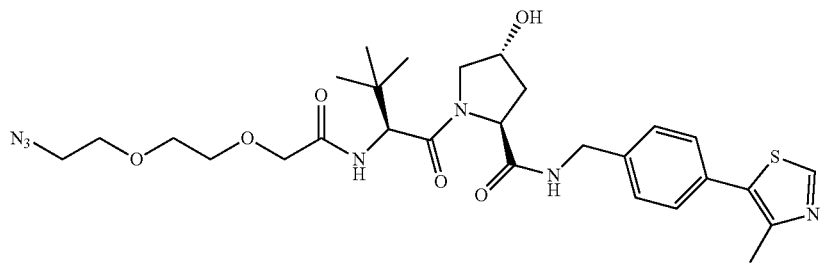 [SMILES: Cc1ncsc1-c1ccc(CNC(=O)[C@@H]2C[C@@H](O)CN2C(=O)[C@@H](NC(=O)COCCOCCN=[N+]=[N-])C(C)(C)C)cc1]

Yield: 411 mg (68%); $^1$H-NMR (CDCl$_3$, 500 MHz) δ 0.95 (s, 9H), 2.08-2.13 (m, 1H), 2.52 (s, 3H), 2.58-2.63 (m, 1H), 2.89 (br, 1H), 3.38-3.41 (m, 2H), 3.61 (dd, 1H, J(H,H)=3.7, J(H,H)=11.4), 3.66-3.70 (m, 6H), 4.01 (q, 2H, J(H,H)=15.5), 4.09-4.12 (m, 1H), 4.33 (dd, 1H, J(H,H)=5.2, J(H,H)=14.9), 4.48 (d, 1H, J(H,H)=8.55), 4.54-4.59 (m, 2H), 4.75 (t, 1H, J(H,H)=7.9), 7.24 (d, 1H, J(H,H)=8.5), 7.33-7.38 (m, 5H), 8.68 (s, 1H); $^{13}$C-NMR (CDCl$_3$, 101 MHz) δ 16.0, 26.5, 34.9, 35.8, 43.4, 50.7, 56.8, 57.3, 58.5, 67.2, 70.2, 70.3, 70.5, 71.2, 127.6, 128.4, 128.6, 129.7, 130.4, 138.4, 150.7, 170.6, 170.7, 171.6; HRMS m/z calc. for C$_{28}$H$_{40}$N$_7$O$_6$S [M+H$^+$] 602.2755, found 602.2769.

(2S,4R)-1-((S)-14-azido-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (MZP-12)

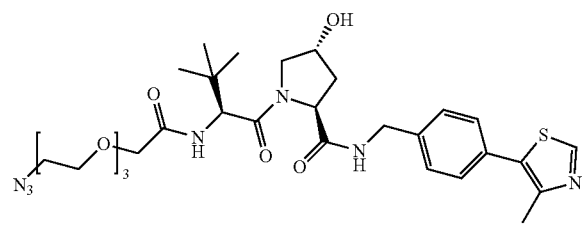

Yield: 491 mg (76%); $^1$H-NMR (CDCl$_3$, 500 MHz) δ 0.95 (s, 9H), 2.09-2.14 (m, 1H), 2.52 (s, 3H), 2.58-2.63 (m, 1H), 2.85 (s, 1H), 3.37 (t, 2H, J(H,H)=10.1 Hz), 3.60 (dd, 1H, J(H,H)=3.6 Hz, J(H,H)=11.4 Hz), 3.64-3.69 (m, 10H), 3.96-4.05 (m, 2H), 4.12-4.14 (m, 1H), 4.34 (dd, 1H, J(H,H)=5.2 Hz, J(H,H)=14.9 Hz), 4.46 (d, 1H, J(H,H)=8.4 Hz), 4.53-4.59 (m, 2H), 4.75 (t, 1H, J(H,H)=7.9 Hz), 7.27 (s, 1H), 7.33-7.38 (m, 5H), 8.67 (s, 1H); $^{13}$C-NMR (CDCl$_3$, 126 MHz) δ 16.2, 26.6, 34.8, 35.7, 43.5, 50.9, 56.7, 57.4, 58.4, 70.2, 70.3, 70.5, 70.7, 70.8, 70.9, 71.3, 128.4, 129.7, 131.2, 131.7, 138.2, 148.7, 150.4, 170.6, 170.8, 171.8; HRMS m/z calc. for C$_{30}$H$_{44}$N$_7$O$_7$S [M+H$^+$] 646.3017, found 646.3023.

(2S,4R)-1-((S)-17-azido-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide (MZP-9)

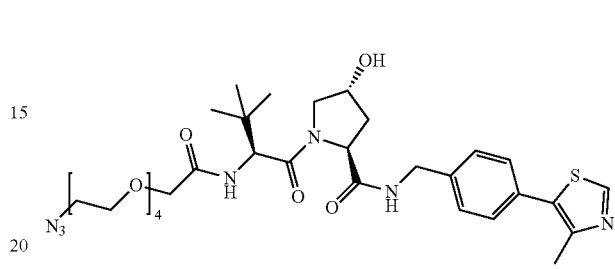

Yield: 607 mg (88%); $^1$H-NMR (CDCl$_3$, 500 MHz) δ 0.95 (s, 9H), 2.10-2.15 (m, 1H), 2.51-2.58 (m, 4H), 2.96 (d, 1H, J(H,H)=3.0 Hz), 3.39-3.41 (m, 2H), 3.60-3.67 (m, 15H), 3.97-4.05 (m, 2H), 4.07-4.09 (m, 1H), 4.35 (dd, 1H, J(H,H)=5.3 Hz, J(H,H)=14.9 Hz), 4.49 (d, 1H, J(H,H)=8.5 Hz), 4.53-4.57 (m, 2H), 4.73 (t, 1H, J(H,H)=7.9 Hz), 7.15 (d, 1H, J(H,H)=8.5 Hz), 7.30-7.38 (m, 5H), 8.68 (s, 1H); $^{13}$C-NMR (CDCl$_3$, 126 MHz) δ 16.2, 26.5, 26.6, 35.0, 35.9, 43.4, 50.8, 56.8, 57.3, 58.5, 70.2-71.3, 128.3, 129.7, 131.1, 131.8, 138.3, 148.6, 150.5, 170.7, 170.8, 171.6; HRMS m/z calc. for C$_{32}$H$_{48}$N$_7$O$_8$S [M+H$^+$] 690.3280, found 690.3308.

(2S,4R)-1-((2S,5S)-17-azido-5-benzyl-2-(tert-butyl)-4,7-dioxo-9,12,15-trioxa-3,6-diazaheptadecanoyl)-4-hydroxy-N-(4-(4-methylthiazol-5-yl)benzyl)pyrrolidine-2-carboxamide (MZP-20)

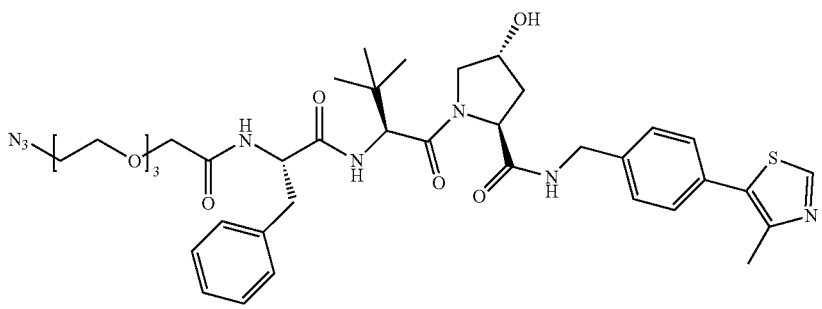

Yield 642 mg (81%); $^1$H-NMR (CDCl$_3$, 500 MHz) δ 0.89 (s, 9H), 2.12-2.16 (m, 1H), 2.51-2.56 (m, 4H), 2.97-3.01 (m, 2H), 3.09-3.14 (m, 1H), 3.33-3.37 (m, 2H), 3.51-3.65 (m, 12H), 3.89-3.92 (m, 2H), 3.99-4.01 (m, 1H), 4.34 (dd, 1H, J(H,H)=5.2 Hz, J(H,H)=14.9 Hz), 4.42-4.47 (m, 1H), 4.50-4.54 (m, 2H), 4.64-4.70 (m, 1H), 4.74 (t, 1H, J(H,H)=7.8 Hz), 7.01-7.09 (m, 1H), 7.15-7.24 (m, 4H), 7.31-7.37 (m, 5H), 7.43-7.48 (m, 1H), 8.67 (s, 1H); $^{13}$C-NMR (CDCl$_3$, 126 MHz) δ 16.2, 26.6, 35.6, 36.5, 37.5, 43.3, 50.7, 54.0, 56.9, 58.0, 58.7, 70.1-71.1, 127.0, 128.2, 128.7, 129.4, 129.6, 131.0, 131.7, 136.4, 138.2, 148.5, 150.4, 170.6, 171.1, 171.1, 171.3; HRMS m/z calc. for C$_{39}$H$_{52}$N$_8$O$_8$S [M+H$^+$] 793.3702, found 793.3707.

(2S,4S)-1-((S)-14-azido-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (MZP-39)

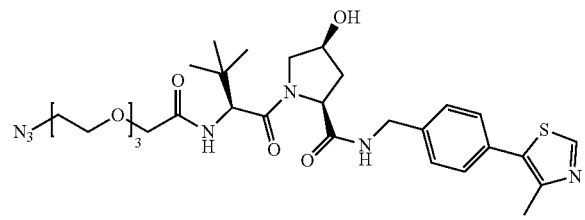

Yield 194 mg (30%); $^1$H-NMR (CDCl$_3$, 400 MHz) δ 0.93 (s, 9H), 2.14-2.21 (m, 1H), 2.35-2.39 (s, 1H), 2.52 (s, 3H), 3.36 (t, 2H, J(H,H)=5.1 Hz), 3.63-3.68 (m, 10H), 3.79-3.82 (m, 1H), 3.91-3.95 (m, 1H), 3.95-4.05 (m, 2H), 4.30 (dd, 1H, J(H,H)=5.1 Hz, J(H,H)=14.9 Hz), 4.45-4.50 (m, 1H), 4.53 (d, 1H, J(H,H)=9.2 Hz), 4.64 (dd, 1H, J(H,H)=7.1 Hz, J(H,H)=14.9 Hz), 4.74 (d, 1H, J(H,H)=9.0 Hz), 5.53 (d, 1H, J(H,H)=9.9 Hz), 7.18 (d, 1H, J(H,H)=9.1 Hz), 7.33-7.39 (m, 4H), 7.50-7.53 (m, 1H), 8.68 (s, 1H); $^{13}$C-NMR (CDCl$_3$, 101 MHz) δ 16.2, 26.4, 35.1, 35.2, 43.7, 50.8, 56.6, 58.8, 60.0, 70.2-71.3, 128.3, 129.8, 131.4, 131.6, 137.5, 148.7, 150.5, 169.9, 172.0, 172.7; HRMS m/z calc. for C$_{30}$H$_{44}$N$_7$O$_7$S [M+H$^+$] 646.3017, found 646.3040.

(S)-2-(4-(4-chlorophenyl)-2,3,9-trimethyl-6H-thieno[3,2-f][1,2,4]triazolo[4,3-a][1,4]diazepin-6-yl)acetic acid (17)

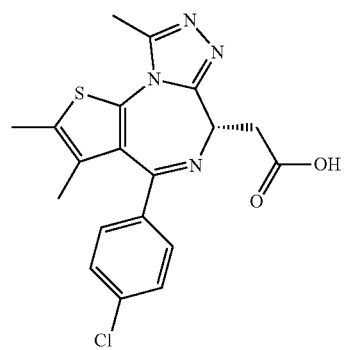

(+)-JQ-1 (50 mg, 109 μmol) was dissolved in formic acid (3 ml) and stirred for 18 h at 25° C. After addition of water the reaction mixture was extracted three times with dichloromethane. The combined organic layers were dried over magnesium sulfate and evaporated to dryness to obtain the title compound which was directly used for the next reaction step. Yield 42.1 mg (96%).

General Procedure for Making PROTACs of Structure A-L-B, from De-Protected Intermediates The starting azide, of structure Az-L-A, such as for example intermediate compound (13) (40 μmol) was dissolved in methanol (5 ml). A catalytic amount of palladium on charcoal (10 wt %) was added and the reaction mixture was then stirred under an atmosphere of hydrogen gas for about 3 h at 25° C. The reaction mixture was then filtered through a plug of celite and the resulting solution evaporated to dryness to obtain the desired intermediate amine, corresponding to the starting azide which was then linked to the desired B-group without further purification.

The intermediate amine, in this general example, the amine equivalent of intermediate compound (13) (35 μmol, 1.4 eq.) and the desired B-group, in this general example suitable B-groups include the: free acid of JQ1 (11.4 mg, 25 μmol, 1 eq.), or I-BET726 (10.9 mg, 25 μmol, 1 eq.), or free acid of I-BET762 (9.92 mg, 25 mol, 1 eq.), were then dissolved in DCM (2 ml). HATU (14.3 mg, 37.5 μmol, 1.5 eq.) was then added and the pH of the resultant mixture was adjusted to >9 by adding DIPEA (17.5 μl, 100 μmol, 4 eq.). After stirring the reaction mixture at 25° C. for 18 h the solvent was removed in vacuum. Purification of the crude product was achieved by preparative HPLC as described in the general information in order to furnish the desired PROTAC.

For the avoidance of doubt, such intermediate amines are prepared from the corresponding de-protected azides by any suitable methods, and in particular, via reduction over palladium, with the resultant amines being utilized directly without further purification.

Any PROTAC compound of structure A-L-B can be prepared in accordance with the general procedure outlined starting from intermediate compounds (13), by use of the appropriate starting Az-L-A compound and the desired B-group, as outlined in Scheme 2.

PROTAC compounds MZ1, MZ2, MZ3, MZP-11, MZP-15, MZP-25, MZP-54, MZP-55, MZP-60 and MZP-61 as detailed herein after were prepared in accordance with the above general methodology from the appropriate starting azide and B-group.

(2S,4R)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide (MZ1) (MZP-22)

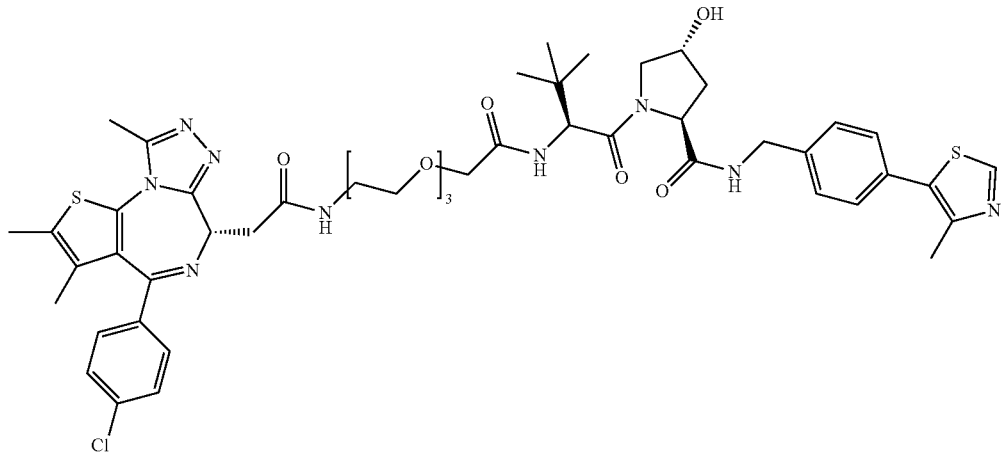

Yield: 9.51 mg (22%); $^1$H-NMR (CDCl$_3$, 500 MHz) δ 0.97 (s, 9H), 1.66 (s, 3H), 2.12-2.17 (m, 1H), 2.39 (s, 3H), 2.43-2.49 (m, 1H), 2.51 (s, 3H), 2.61 (s, 3H), 3.31-3.35 (m, 2H), 3.47-3.74 (m, 13H), 4.11-4.14 (m, 2H), 4.27-4.33 (m, 2H), 4.49-4.55 (m, 2H), 4.65-4.69 (m, 3H), 4.84 (t, 1H, J(H,H)=7.9 Hz), 7.23-7.25 (m, 1H), 7.29-7.39 (m, 9H), 7.91-7.94 (m, 1H), 8.67 (s, 1H); $^{13}$C-NMR (CDCl$_3$, 101 MHz) δ 11.9, 13.2, 14.6, 16.2, 26.6, 35.6, 36.4, 38.2, 39.9, 43.3, 54.3, 56.9, 57.3, 59.0, 70.1-70.9, 71.7, 128.2, 128.9, 129.6, 130.1, 130.9, 131.0, 131.2, 131.8, 132.0, 136.7, 136.8, 138.4, 148.6, 149.9, 150.4, 156.0, 164.0, 171.0, 171.3, 171.4; HRMS m/z calc. for C$_{49}$H$_{61}$ClN$_9$O$_8$S$_2$ [M+H$^+$] 1002.3768, found 1002.3786.

(2S,4R)-1-((S)-2-(tert-butyl)-20-((S)-4-(4-chlorophenyl)-2,3,9-trimethyl-6H-thieno[3,2-f][1,2,4]triazolo[4,3-a][1,4]diazepin-6-yl)-4,19-dioxo-6,9,12,15-tetraoxa-3,18-diazaicosanoyl)-4-hydroxy-N-(4-(4-methylthiazol-5-yl)benzyl)pyrrolidine-2-carboxamide (MZ2) (MZP-21)

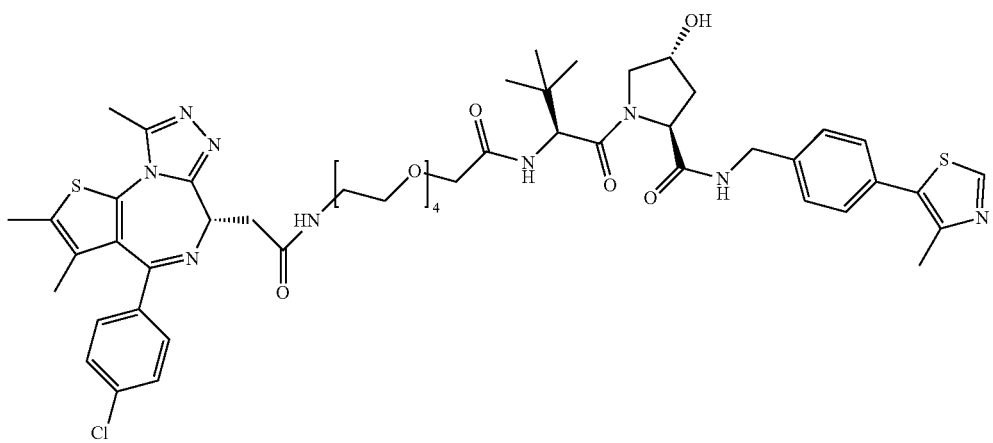

Yield: 10.1 mg (23%); $^1$H-NMR (CDCl$_3$, 500 MHz) δ 0.96 (s, 9H), 1.65 (s, 3H), 2.12-2.17 (m, 1H), 2.39 (s, 3H), 2.44-2.48 (m, 1H), 2.51 (s, 3H), 2.62 (s, 3H), 3.37-3.45 (m, 2H), 3.53-3.69 (m, 16H), 4.01 (d, 1H, J(H,H)=15.7 Hz), 4.06-4.09 (m, 1H), 4.15-4.18 (m, 1H), 4.33 (dd, 1H, J(H,H)=5.4 Hz, J(H,H)=15.0 Hz), 4.41-4.47 (m, 2H), 4.54 (dd, 2H, J(H,H)=6.5 Hz, J(H,H)=15.1 Hz), 4.62-4.67 (m, 2H), 4.80 (t, 1H, J(H,H)=8.0 Hz), 7.29-7.39 (m, 9H), 7.44 (t, 1H, J(H,H)=6.1 Hz), 7.56-7.58 (m, 1H), 8.67 (s, 1H); $^{13}$C-NMR (CDCl$_3$, 101 MHz) δ 11.9, 13.2, 14.6, 16.2, 26.6, 35.6, 36.4, 38.2, 39.9, 43.3, 54.3, 56.9, 57.2, 59.0, 70.1-70.9, 71.7, 128.2, 128.9, 129.6, 130.1, 130.9, 131.0, 131.2, 131.8, 132.0, 136.7, 136.8, 138.4, 148.6, 149.9, 150.4, 156.0, 164.0, 171.0, 171.3, 171.4; HRMS m/z calc. for C$_{51}$H$_{65}$ClN$_9$O$_9$S$_2$ [M+H$^+$] 1046.4030, found 1046.4067.

(2S,4R)-1-((2S,5S)-5-benzyl-2-(tert-butyl)-20-((S)-4-(4-chlorophenyl)-2,3,9-trimethyl-6H-thieno[3,2-f][1,2,4]triazolo[4,3-a][1,4]diazepin-6-yl)-4,7,19-trioxo-9,12,15-trioxa-3,6,18-triazaicosanoyl)-4-hydroxy-N-(4-(4-methylthiazol-5-yl)benzyl)pyrrolidine-2-carboxamide (MZ3) (MZP-24)

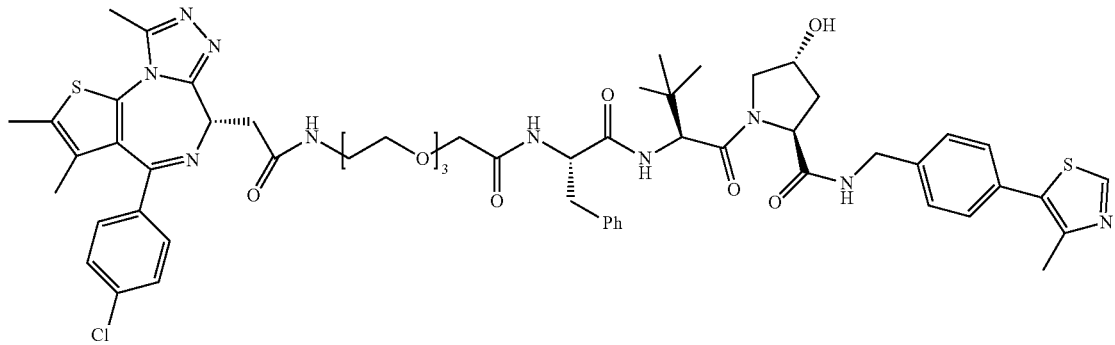

Yield: 33.0 mg (58%); $^1$H-NMR (CDCl$_3$, 500 MHz) δ 0.90 (s, 9H), 1.64 (s, 3H), 2.09-2.14 (m, 1H), 2.39 (s, 3H), 2.48-2.54 (m, 4H), 2.64 (s, 3H), 3.06-3.12 (m, 1H), 3.14-3.20 (m, 2H), 3.41-3.69 (m, 15H), 3.94 (q, 2H, J(H,H)=16.3 Hz), 4.03 (d, 1H, J(H,H)=11.1 Hz), 4.29 (dd, 1H, J(H,H)=5.4 Hz, J(H,H)=15.0 Hz), 4.47 (s, 1H), 4.52 (dd, 1H, J(H,H)=6.5 Hz, J(H,H)=15.0 Hz), 4.60 (d, 1H, J(H,H)=9.1 Hz), 4.62-4.66 (m, 1H), 4.70 (t, 1H, J(H,H)=7.0 Hz), 4.75 (t, 1H, J(H,H)=7.7 Hz), 6.99 (d, 1H, J(H,H)=8.8 Hz), 7.15-7.24 (m, 7H), 7.31-7.36 (m, 7H), 7.66 (d, 1H, J(H,H)=8.0 Hz), 7.82-7.84 (m, 1H), 8.67 (s, 1H); $^{13}$C-NMR (CDCl$_3$, 126 MHz) δ 11.9, 13.2, 14.5, 16.2, 17.5, 18.8, 26.5, 35.8, 36.3, 36.8, 38.3, 39.6, 42.0, 43.3, 53.8, 54.2, 54.7, 57.2, 57.7, 58.9, 69.9-70.8, 126.8, 128.2, 128.6, 128.8, 129.4, 129.5, 130.0, 130.8, 131.1, 131.2, 131.8, 132.0, 136.9, 137.0, 138.3, 148.5, 150.0, 150.4, 155.9, 170.8, 170.9, 171.0, 171.3, 171.4; HRMS m/z calc. for C$_{58}$H$_{70}$ClN$_{10}$O$_9$S$_2$ [M+H$^+$] 1149.4452, found 1149.4473.

(2S,4R)-1-((S)-2-(tert-butyl)-14-((S)-4-(4-chlorophenyl)-2,3,9-trimethyl-6H-thieno[3,2-f][1,2,4]triazolo[4,3-a][1,4]diazepin-6-yl)-4,13-dioxo-6,9-dioxa-3,12-diazatetradecanoyl)-4-hydroxy-N-(4-(4-methylthiazol-5-yl)benzyl)pyrrolidine-2-carboxamide (MZP-60)

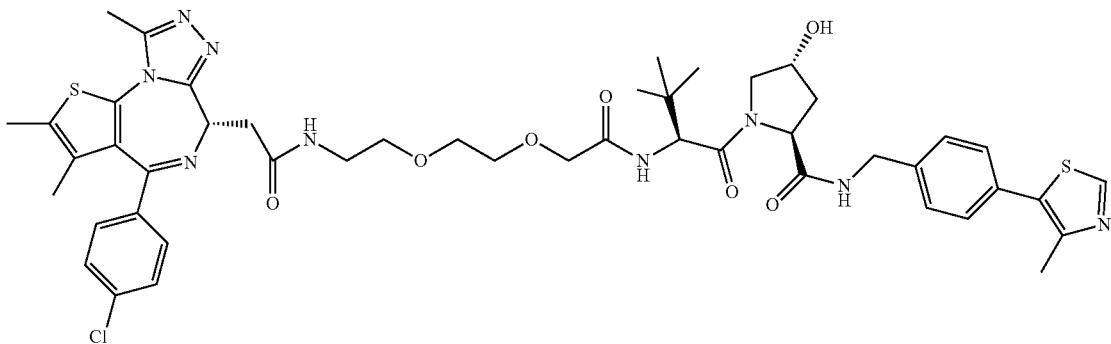 [SMILES: Cc1ncsc1-c1ccc(CNC(=O)[C@@H]2C[C@@H](O)CN2C(=O)[C@@H](NC(=O)COCCOCCNC(=O)C[C@@H]2N=C(c3ccc(Cl)cc3)c3c(sc(C)c3C)-n3c(C)nnc32)C(C)(C)C)cc1]

Yield: 22.2 mg (66%); $^1$H-NMR (CDCl$_3$, 500 MHz) δ 1.09 (s, 9H), 1.66 (s, 3H), 2.20-2.26 (m, 1H), 2.35-2.40 (m, 4H), 2.45 (s, 3H), 2.55 (s, 3H), 3.09-3.13 (m, 1H), 3.44 (dd, 1H, J(H,H)=3.0, J(H,H)=15.9), 3.54-3.61 (m, 8H), 3.81-4.07 (m, 6H), 4.21 (d, 2H, J(H,H)=5.8), 4.57-4.63 (m, 2H), 4.86-4.94 (m, 2H), 7.02 (d, 2H, J(H,H)=8.0), 7.11 (d, 2H, J(H,H)=8.0), 7.24 (d, 1H, J(H,H)=8.3), 7.36 (d, 2H, J(H,H)=8.4), 7.64 (d, 1H, J(H,H)=10.0), 8.24-8.30 (m, 2H), 8.65 (s, 1H); $^{13}$C-NMR (CDCl$_3$, 101 MHz) δ 11.8, 13.3, 14.5, 16.2, 26.6, 36.3, 37.2, 38.3, 39.7, 42.7, 53.9, 56.5, 57.5, 59.3, 69.8, 70.3, 70.4, 71.5, 127.7, 128.8, 129.0, 130.1, 130.2, 131.2, 131.3, 131.4, 131.6, 131.9, 136.7, 136.9, 138.5, 148.4, 149.9, 150.2, 156.2, 163.3, 170.4, 170.6, 171.1, 172.1; HRMS m/z calc. for C$_{47}$H$_{57}$ClN$_9$O$_7$S$_2$ [M+H$^+$] 958.3505, found 958.3498.

(2S,4R)-1-((S)-1-(4-((2S,4R)-1-acetyl-4-((4-chlorophenyl)amino)-2-methyl-1,2,3,4-tetrahydroquinolin-6-yl)phenyl)-15-(tert-butyl)-1,13-dioxo-5,8,11-trioxa-2,14-diazahexadecan-16-oyl)-4-hydroxy-N-(4-(4-methylthiazol-5-yl)benzyl)pyrrolidine-2-carboxamide (MZP-54)

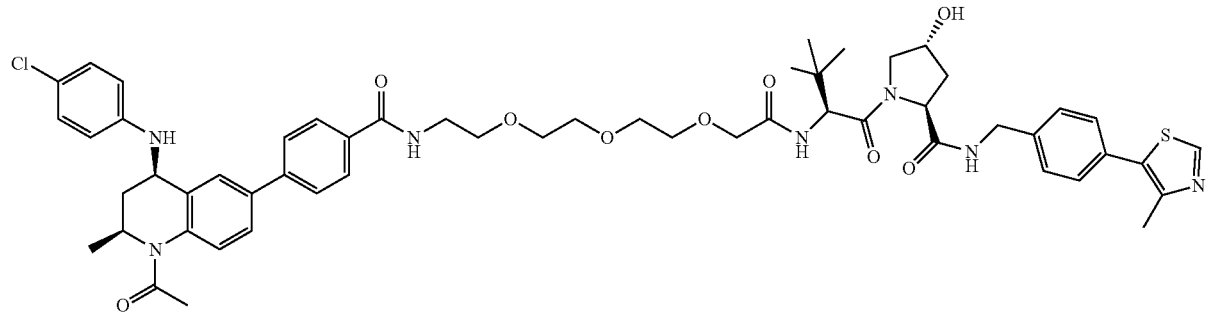 [SMILES: CC(=O)N1c2ccc(-c3ccc(C(=O)NCCOCCOCCOCC(=O)N[C@H](C(=O)N4C[C@H](O)C[C@H]4C(=O)NCc4ccc(-c5scnc5C)cc4)C(C)(C)C)cc3)cc2[C@H](Nc2ccc(Cl)cc2)C[C@@H]1C]

Yield: 17.1 mg (71%); $^1$H-NMR (CDCl$_3$, 400 MHz) δ 0.93 (s, 9H), 1.18 (s, 1H, J(H,H)=6.3), 2.01-2.08 (m, 3H), 2.22 (s, 3H), 2.37-2.43 (m, 1H), 2.50 (s, 3H), 2.64-2.70 (m, 1H), 3.21 (s, 1H), 3.53-3.65 (m, 14H), 3.73-3.77 (m, 1H), 3.86-3.94 (m, 2H), 4.18-4.33 (m, 3H), 4.42-4.62 (m, 4H), 4.88-4.89 (m, 1H), 6.64 (d, 2H, J(H,H)=8.7), 7.13 (d, 2H, J(H,H)=8.7), 7.20-7.23 (m, 2H), 7.30-7.35 (m, 6H), 7.50-7.51 (m, 4H), 7.80 (d, 2H, J(H,H)=8.2), 8.66 (s, 1H); $^{13}$C-NMR (CDCl$_3$, 101 MHz) δ 16.2, 21.5, 23.2, 26.5, 35.5, 36.3, 40.1, 41.1, 43.3, 47.7, 50.3, 56.9, 57.0, 58.7, 69.7, 70.1, 70.3, 70.4, 70.5, 71.1, 114.7, 122.7, 122.9, 126.0, 126.6, 127.0, 127.9, 128.2, 129.4, 129.6, 131.1, 133.6, 136.4, 137.8, 138.3, 143.3, 145.9, 150.4, 167.5, 169.6, 170.3, 171.0, 171.2; HRMS m/z calc. for C$_{55}$H$_{67}$ClN$_7$O$_9$S [M+H$^+$] 1036.4404, found 1036.4356.

(2S,4R)-1-((S)-1-(4-((2S,4R)-1-acetyl-4-((4-chlorophenyl)amino)-2-methyl-1,2,3,4-tetrahydroquinolin-6-yl)phenyl)-18-(tert-butyl)-1,16-dioxo-5,8,11,14-tetraoxa-2,17-diazanonadecan-19-oyl)-4-hydroxy-N-(4-(4-methylthiazol-5-yl)benzyl)pyrrolidine-2-carboxamide (MZP-55)

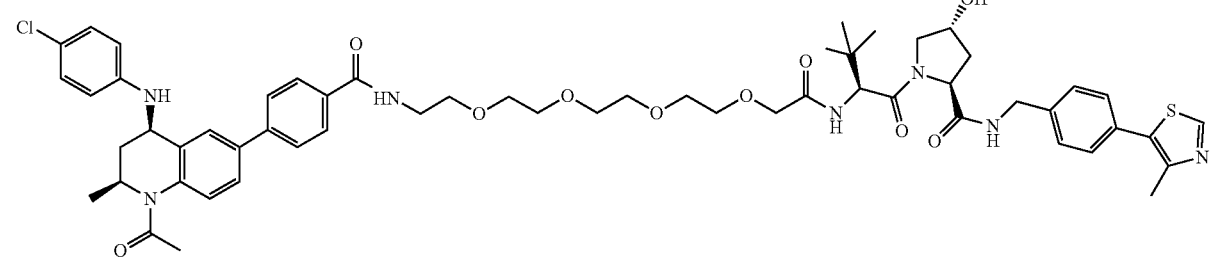

Yield: 14.6 mg (58%); $^1$H-NMR (CDCl$_3$, 400 MHz) δ 0.93 (s, 9H), 1.18 (d, 1H, J(H,H)=6.3), 2.06-2.10 (m, 3H), 2.22 (s, 3H), 2.44-2.50 (m, 4H), 2.63-2.69 (m, 1H), 3.45 (s, 1H), 3.56-3.63 (m, 18H), 3.81-4.00 (m, 3H), 4.16-4.24 (m, 2H), 4.30-4.35 (m, 1H), 4.46-4.56 (m, 3H), 4.69 (m, 1H, J(H,H)=7.84), 4.84-4.92 (m, 1H), 6.62 (d, 2H, J(H,H)=8.6), 7.13 (d, 3H, J(H,H)=8.6), 7.22-7.27 (m, under solvent peak, 2H), 7.31-7.37 (m, 5H), 7.50-7.53 (m, 4H), 7.83 (d, 2H, J(H,H)=8.2), 8.66 (s, 1H); $^{13}$C-NMR (CDCl$_3$, 101 MHz) δ 16.2, 21.5, 23.2, 26.5, 35.4, 36.2, 40.0, 41.2, 43.3, 47.6, 50.4, 56.9, 57.1, 58.7, 69.9, 70.3, 70.7, 71.1, 114.6, 122.7, 126.0, 126.6, 127.1, 127.9, 128.2, 129.4, 129.6, 131.0, 133.5, 136.4, 137.9, 138.3, 143.3, 145.9, 150.5, 167.4, 169.6, 170.4, 171.0, 171.3; HRMS m/z calc. for C$_{57}$H$_{71}$ClN$_7$O$_{10}$S [M+H$^+$] 1080.4666, found 1080.4623.

(2S,4R)-1-((S)-1-(4-((2S,4R)-1-acetyl-4-((4-chlorophenyl)amino)-2-methyl-1,2,3,4-tetrahydroquinolin-6-yl)phenyl)-12-(tert-butyl)-1,10-dioxo-5,8-dioxa-211-diazatridecan-13-oyl)-4-hydroxy-N-(4-(4-methylthiazol-5-yl)benzyl)pyrrolidine-2-carboxamide (MZP-61)

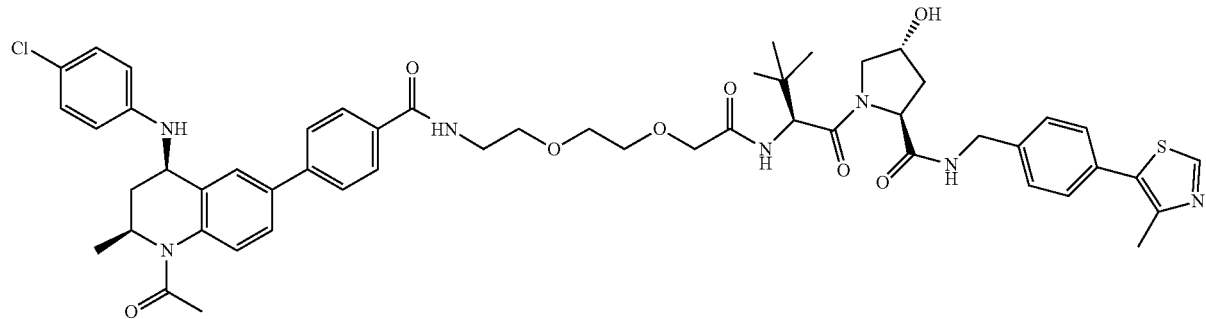 [SMILES: CC(=O)N1c2ccc(-c3ccc(C(=O)NCCOCCOCC(=O)N[C@H](C(=O)N4C[C@H](O)C[C@H]4C(=O)NCc4ccc(-c5scnc5C)cc4)C(C)(C)C)cc3)cc2[C@H](Nc2ccc(Cl)cc2)C[C@@H]1C]

Yield: 14.5 mg (42%); $^1$H-NMR (CDCl$_3$, 400 MHz) δ 0.95 (s, 9H), 1.19 (d, 3H, J(H,H)=6.3), 1.25-1.36 (m, 1H), 1.80 (br, 2H), 1.93-1.99 (m, 1H), 2.24 (s, 3H), 2.32-2.38 (m, 1H), 2.50 (s, 3H), 2.64-2.70 (m, 1H), 3.13-3.23 (br, 1H), 3.48-3.81 (m, 11H), 3.90-74.07 (m, 3H), 4.15-4.22 (m, 2H), 4.37-4.53 (m, 4H), 4.88-4.91 (m, 1H), 6.58-6.62 (m, 3H), 7.13 (d, 2H, J(H,H)=8.60), 7.21-7.23 (m, 2H), 7.31-7.33 (m, 2H), 7.51-7.60 (m, 5H), 7.78-7.79 (m, 1H), 7.91 (d, 2H, J(H,H)=8.12), 8.67 (s, 1H); $^{13}$C-NMR (CDCl$_3$, 101 MHz) δ 16.2, 21.5, 23.2, 26.5, 36.1, 36.3, 40.0, 41.3, 43.4, 50.6, 57.0, 57.2, 58.9, 70.2, 70.7, 70.8, 71.0, 71.8, 114.6, 122.6, 123.0, 126.1, 126.7, 127.0, 128.2, 128.4, 129.5, 129.6, 131.2, 131.7, 133.5, 136.5, 137.9, 143.5, 145.9, 148.6, 150.5, 167.7, 169.6, 170.8, 170.9, 171.3; HRMS m/z calc. for C$_{53}$H$_{63}$ClN$_7$O$_8$S [M+H$^+$] 992.4142, found 992.4091.

MZP-15 MZP-11 and MZP-25 are diastereoisomeric mixtures. The NMR spectra are therefore very complex and difficult to interpret.

(2S,4R)-1-((2S)-2-(tert-butyl)-17-(6-(4-chlorophenyl)-8-methoxy-1-methyl-4H-benzo[f][1,2,4]triazolo[4,3-a][1,4]diazepin-4-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide (MZP-15)

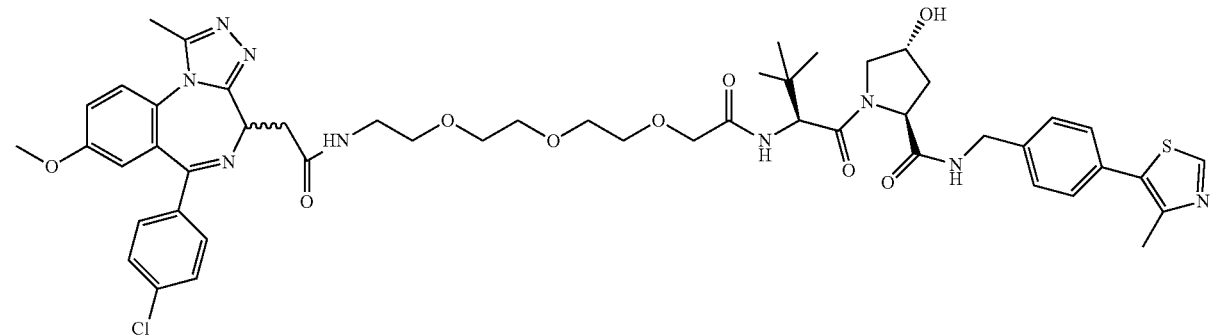 [SMILES: COc1ccc2c(c1)C(c1ccc(Cl)cc1)=NC(CC(=O)NCCOCCOCCOCC(=O)N[C@H](C(=O)N1C[C@H](O)C[C@H]1C(=O)NCc1ccc(-c3scnc3C)cc1)C(C)(C)C)c1nnc(C)n1-2]

Yield: 16.5 mg (47%); $^1$H-NMR (CDCl$_3$, 400 MHz) δ 0.98-0.99 (m, 9H), 2.20-2.28 (m, 2H), 2.35-2.46 (m, 2H), 2.49-2.50 (m, 3H), 2.55-2.57 (m, 3H), 3.25-3.74 (m, 20H), 3.78 (s, 3H), 4.06-4.22 (m, 3H), 4.29-4.41 (m, 2H), 4.49-4.58 (m, 2H), 4.63-4.71 (m, 2H), 4.81-4.87 (m, 1H), 6.84-6.85 (m, 1H), 7.16-7.20 (m, 1H), 7.28-7.40 (m, 7H), 7.45-7.52 (m, 2H), 8.02-8.11 (m, 1H), 8.28-8.31 (m, 1H), 8.62-8.63 (m, 1H), 8.70 (s, 1H); $^{13}$C-NMR (CDCl$_3$, 101 MHz) δ 12.0, 12.1, 16.0, 26.6, 35.6, 35.8, 36.7, 36.9, 38.0, 38.1, 39.9, 40.0, 43.2, 53.5, 53.6, 53.7, 56.0, 56.9, 57.3, 57.5, 59.1, 59.2, 70.2, 70.4, 70.5, 70.6, 70.8, 70.9, 71.2, 71.7, 116.0, 118.2, 120.3, 125.0, 126.2, 128.1, 128.2, 128.6, 128.7, 129.2, 129.5, 130.4, 130.5, 130.6, 131.1, 135.5, 137.0, 137.1, 137.2, 138.6, 138.7, 148.3, 150.3, 150.6, 156.7, 158.3, 166.4, 166.6, 170.7, 170.9, 171.0, 171.1, 171.3, 171.5, 171.7; HRMS m/z calc. for C$_{50}$H$_{61}$ClN$_9$O$_9$S [M+H$^+$] 998.3996, found 998.3996.

(2S,4R)-1-((2S)-2-(tert-butyl)-20-(6-(4-chlorophenyl)-8-methoxy-1-methyl-4H-benzo[f][1,2,4]triazolo[4,3-a][1,4]diazepin-4-yl)-4,19-dioxo-6,9,12,15-tetraoxa-3,18-diazaicosanoyl)-4-hydroxy-N-(4-(4-methylthiazol-5-yl)benzyl)pyrrolidine-2-carboxamide (MZP-11)

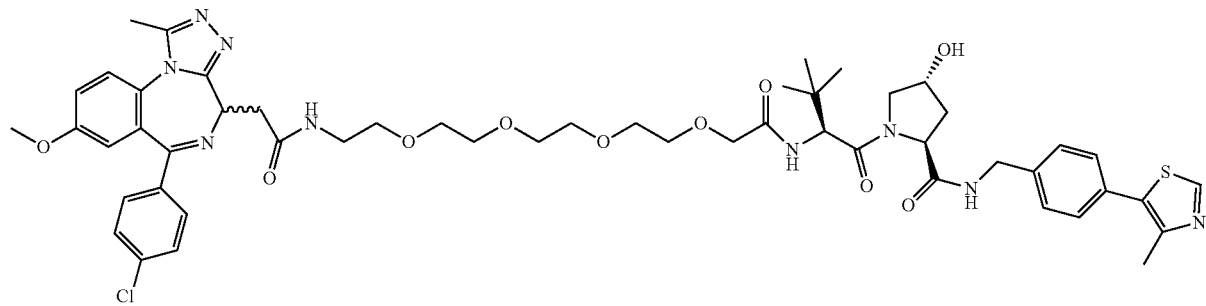 [SMILES: COc1ccc2c(c1)C(c1ccc(Cl)cc1)=NC(CC(=O)NCCOCCOCCOCCOCC(=O)N[C@H](C(=O)N1C[C@H](O)C[C@H]1C(=O)NCc1ccc(-c3scnc3C)cc1)C(C)(C)C)c1nnc(C)n1-2]

Yield: 6.40 mg (18%); $^1$H-NMR (CDCl$_3$, 400 MHz) δ 0.97 (s, 9H), 2.14-2.20 (m, 1H), 2.32-2.40 (m, 1H), 2.50 (s, 3H), 2.56 (s, 3H), 3.31-3.47 (m, 4H), 3.51-3.71 (m, 18H), 3.77-3.78 (m, 3H), 3.98-4.17 (m, 3H), 4.31-4.40 (m, 1H), 4.50-4.56 (m, 2H), 4.61-4.68 (m, 2H), 4.75-4.80 (m, 2H), 6.83-6.84 (m, 1H), 7.16-7.19 (m, 1H), 7.30-7.42 (m, 8H), 7.45-7.48 (m, 2H), 7.53-7.57 (m, 1H), 7.72-7.74 (m, 1H), 7.80-7.83 (m, 1H), 8.66 (s, 1H); $^{13}$C-NMR (CDCl$_3$, 101 MHz) δ 12.2, 16.2, 26.5, 35.7, 36.6, 36.7, 38.4, 39.5, 43.2, 53.7, 56.0, 56.9, 57.0, 57.2, 59.0, 70.1, 70.4, 70.5, 70.7, 70.8, 71.0, 71.2, 116.0, 118.1, 124.9, 126.4, 128.2, 128.6, 129.5, 130.3, 130.8, 131.0, 131.8, 137.0, 137.1, 137.2, 138.5, 138.6, 148.5, 150.4, 150.6, 156.6, 158.2, 166.5, 170.5, 170.6, 170.7, 170.8, 171.1, 171.2, 171.4, 171.5; HRMS m/z calc. for C$_{52}$H$_{65}$ClN$_9$O$_{10}$S [M+H$^+$] 1042.4258, found 1042.4251.

(2S,4R)-1-((2S,5S)-5-benzyl-2-(tert-butyl)-20-(6-(4-chlorophenyl)-8-methoxy-1-methyl-4H-benzo[f][1,2,4]triazolo[4,3-a][1,4]diazepin-4-yl)-4,7,19-trioxo-9,12,15-trioxa-3,6,18-triazaicosanoyl)-4-hydroxy-N-(4-(4-methylthiazol-5-yl)benzyl)pyrrolidine-2-carboxamide (MZP-25)

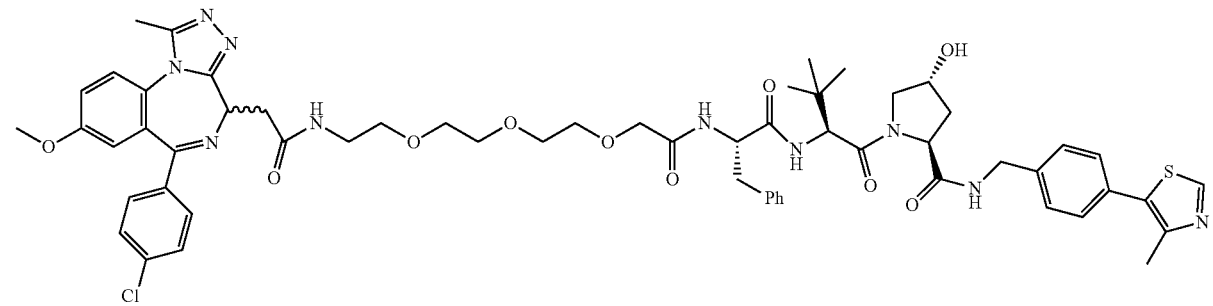 [SMILES: COc1ccc2c(c1)C(c1ccc(Cl)cc1)=NC(CC(=O)NCCOCCOCCOCC(=O)N[C@@H](Cc1ccccc1)C(=O)N[C@H](C(=O)N1C[C@H](O)C[C@H]1C(=O)NCc1ccc(-c3scnc3C)cc1)C(C)(C)C)c1nnc(C)n1-2]

Yield: 21.2 mg (53%); $^1$H-NMR (CDCl$_3$, 400 MHz) δ 0.89-0.91 (m, 9H), 1.43-1.45 (m, 1H), 1.52-1.57 (m, 1H), 2.16-2.21 (m, 1H), 2.42-2.56 (m, 7H), 3.07-3.19 (m, 2H), 3.36-3.69 (m, 16H), 3.78-3.79 (m, 3H), 3.88-4.07 (m, 3H), 4.29-4.38 (m, 1H), 4.47-4.53 (m, 2H), 4.58-4.78 (m, 4H), 5.26-5.30 (m, 1H), 6.82-6.86 (m, 1H), 7.14-7.22 (m, 7H), 7.30-7.36 (m, 6H), 7.40-7.53 (m, 3H), 7.68-7.70 (m, 1H), 7.88-7.95 (m, 1H), 8.66 (s, 1H); $^{13}$C-NMR (CDCl$_3$, 101 MHz) δ 12.2, 16.2, 26.5, 35.8, 35.9, 36.2, 36.8, 37.1, 38.3, 39.7, 43.3, 53.7, 54.8, 55.3, 56.0, 57.2, 57.7, 57.8, 58.9, 59.0, 69.9, 70.0, 70.2, 70.3, 70.6, 70.8, 116.0, 118.1, 124.9, 126.3, 126.9, 128.3, 128.6, 128.7, 129.4, 129.6, 130.4, 130.9, 131.0, 137.0, 137.1, 138.4, 148.6, 150.4, 150.6, 156.7, 156.8, 158.2, 158.3, 166.4, 170.8, 170.9, 171.0, 171.3, 171.5; HRMS m/z calc. for C$_{59}$H$_{70}$ClN$_{10}$O$_{10}$S [M+H$^+$] 1145.4680, found 1145.4647.

(2S,4S)-1-((S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide (cisMZ1) (MZP-42)

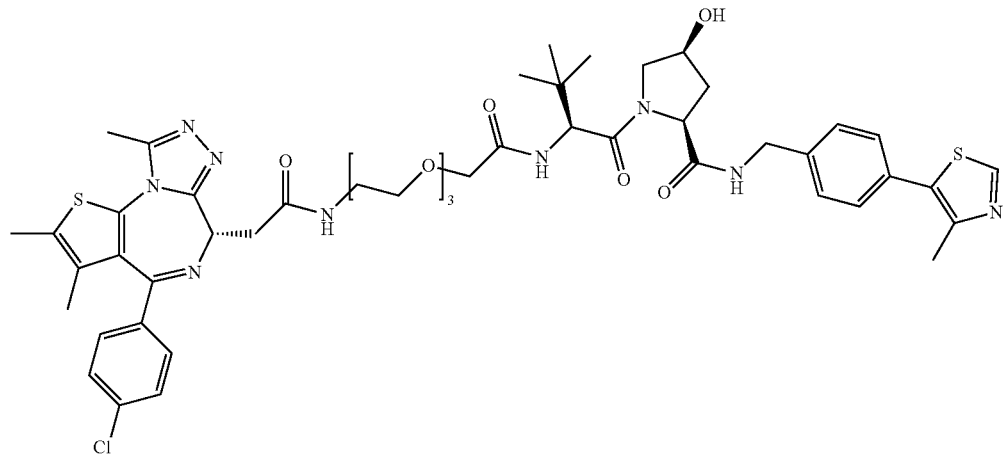

Yield: 19.7 mg (37%); $^1$H-NMR (CDCl$_3$, 400 MHz) δ 0.99 (s, 9H), 1.65 (s, 3H), 2.18-2.21 (m, 2H), 2.38 (s, 3H), 2.49 (s, 3H), 2.60 (s, 3H), 3.35-3.69 (m, 14H), 3.85-3.88 (m, 1H), 3.93-3.96 (m, 1H), 4.08 (q, 2H, J(H,H)=15.5 Hz), 4.25 (dd, 1H, J(H,H)=5.2 Hz, J(H,H)=15.1 Hz), 4.40-4.44 (m, 1H), 4.53-4.64 (m, 3H), 4.80-4.83 (m, 1H), 5.75 (d, 1H, J(H,H)=10.3 Hz), 7.24 (d, 1H, J(H,H)=9.7 Hz), 7.27-7.39 (m, 8H), 7.43 (t, 1H, J(H,H)=5.4 Hz), 8.08 (t, 1H, J(H,H)=6.2 Hz), 8.67 (s, 1H); $^{13}$C-NMR (CDCl$_3$, 101 MHz) δ 11.9, 13.2, 14.5, 16.2, 26.5, 35.2, 35.8, 38.7, 39.7, 43.4, 54.4, 56.6, 58.6, 60.0, 70.1-71.3, 128.0, 128.8, 129.5, 130.0, 130.9, 131.1, 131.7, 132.1, 136.7, 136.8, 137.8, 148.5, 149.9, 150.4, 155.8, 163.8, 170.2, 170.8, 171.4, 173.3; HRMS m/z calc. for C$_{49}$H$_{61}$ClN$_9$O$_8$S$_2$ [M+H$^+$] 1002.3768, found 1002.3791.

---

The invention claimed is:
1. A compound having the structure:

A-L-B wherein A is an E3 ubiquitin ligase protein binding ligand compound of formula IA

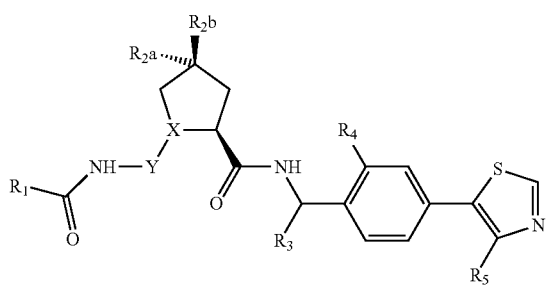

IA wherein L is a —(CH$_2$CH$_2$O)$_b$—group which is directly bonded to the compound of formula IA,
wherein X is N,
wherein b is 1 to 10,
wherein R$^1$ is a —(CH2)$_m$Q$_v$, group with a covalent C-linked bond to L, wherein m is 1 and v is 0, and wherein Q is a (C$_3$-C$_4$)cyclic or (C$_3$-C$_4$)—C-linked nitrogen containing heterocyclic group,
wherein R$_2$a is OH,
wherein R$_2$b is H,
wherein R$^3$ and R$^4$ are both H,
wherein R$^5$ is a —CH$_3$ group,
wherein Y is

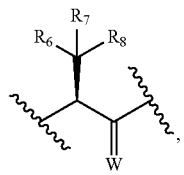

wherein W is O,
wherein R$_6$, R$_7$ and R$_8$ are each —CH$_3$,
wherein B is

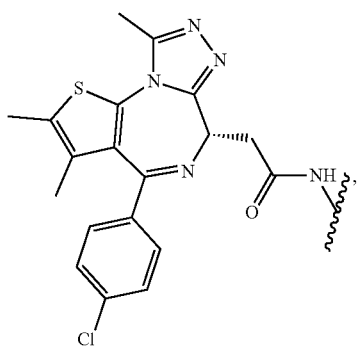 [SMILES: *NC(=O)C[C@@H]1N=C(c2ccc(Cl)cc2)c2c(sc(C)c2C)-n2c(C)nnc21]

or a pharmaceutically acceptable, salt, enantiomer, stereoisomer, hydrate, solvate, or polymorph thereof.

2. The compound according to claim 1 independently selected from:
(2S,4R)-1-(S)-2-(tert-butyl)-17-((S)-4-(4-chlorophenyl)-2,3,9-trimethyl-6H-thieno[3,2-f][1,2,4]triazolo[4,3-a][1,4]diazepin-6-yl)-4,16-dioxo-6,9,12-trioxa-3,15-diazaheptadecanoyl) -4-hydroxy-N-(4-(4-methylthiazol-5-yl)benzyl)pyrrolidine-2-carboxamide;

or a pharmaceutically acceptable, salt, enantiomer, stereoisomer, hydrate, solvate, or polymorph thereof.

3. The compound according to claim 1, wherein b is 1 to 4.

4. The compound according to claim 1, wherein L is PEG-3.

5. A pharmaceutical composition comprising a compound as defined in claim 1 and a pharmaceutically acceptable vehicle or diluent.

6. A pharmaceutical composition comprising
an effective amount of a compound according to claim 1 in combination with a pharmaceutically acceptable carrier, additive or excipient and optionally in further combination with a bioactive agent for the treatment of a condition selected from the group consisting of cancer, benign proliferative disorders, infection or non-infectious inflammatory events, autoimmune diseases, inflammatory diseases, systemic inflammatory response syndromes, viral infections and diseases, and opthamological conditions.

7. A method of regulating protein activity of a BET bromodomain target protein in a patient in need comprising
administering to the patient an effective amount of a compound according to claim 1.

8. A method of degrading a BET bromodomain target protein in a patient in need comprising
administering to the patient an effective amount of a compound according to claim 1.

9. A method for the treatment of a disease or condition associated with deregulation of protein activity of one or more proteins within a Bromo-and Extra-terminal (BET) family of proteins BRD2, BRD3 and BRD4 comprising
administering a therapeutically effective amount of a compound according to claim 1 to a patient in need of treatment.

10. A method for the treatment of a disease or condition associated with selective degradation of a BRD4 protein within a bromodomain of a BET family of proteins comprising
administering a therapeutically effective amount of a compound according to claim 1 to a patient in need of treatment.

* * * * *

UNITED STATES PATENT AND TRADEMARK OFFICE
CERTIFICATE OF CORRECTION

| | |
|---|---|
| PATENT NO. | : 11,179,373 B2 |
| APPLICATION NO. | : 15/557525 |
| DATED | : November 23, 2021 |
| INVENTOR(S) | : Ciulli et al. |

It is certified that error appears in the above-identified patent and that said Letters Patent is hereby corrected as shown below:

On the Title Page

Item (54), and in the Specification, Column 1 Lines 1-7, Please amend the title as follows:
--Derivatives of 1-[(cyclopentyl or 2-pyrrolidinyl)carbonylaminomethyl]-4-(1,3-Thiazol-5-yl) benzene which are Useful for the Treatment of Proliferative, Autoimmune or Inflammatory Diseases--

Signed and Sealed this
Seventeenth Day of May, 2022

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: AREG-fw

<400> SEQUENCE: 1
aaggagaagc tgaggaacga a                     21

```
<210> SEQ ID NO 2
<211> LENGTH: 20
<212> TYPE: DNA
<213> ORGANISM: Artificial Sequence
<220> FEATURE:
<223> OTHER INFORMATION: AREG-rv

<400> SEQUENCE: 2
tggctatgac ttggcagtga                                                 20

<210> SEQ ID NO 3
<211> LENGTH: 20
<212> TYPE: DNA
<213> ORGANISM: Artificial Sequence
<220> FEATURE:
<223> OTHER INFORMATION: FAS-fw

<400> SEQUENCE: 3
agaacttgga aggcctgcat                                                 20

<210> SEQ ID NO 4
<211> LENGTH: 20
<212> TYPE: DNA
<213> ORGANISM: Artificial Sequence
<220> FEATURE:
<223> OTHER INFORMATION: FAS-rv

<400> SEQUENCE: 4
gtctggttca tccccattga                                                 20

<210> SEQ ID NO 5
<211> LENGTH: 20
<212> TYPE: DNA
<213> ORGANISM: Artificial Sequence
<220> FEATURE:
<223> OTHER INFORMATION: FGFR1-fw

<400> SEQUENCE: 5
ctgaccacag aattggaggc                                                 20

<210> SEQ ID NO 6
<211> LENGTH: 20
<212> TYPE: DNA
<213> ORGANISM: Artificial Sequence
<220> FEATURE:
<223> OTHER INFORMATION: FGFR1-rv

<400> SEQUENCE: 6
gcaggtgtag ttgcccttgt                                                 20

<210> SEQ ID NO 7
<211> LENGTH: 20
<212> TYPE: DNA
<213> ORGANISM: Artificial Sequence
<220> FEATURE:
<223> OTHER INFORMATION: MYC-fw

<400> SEQUENCE: 7
ccgcttctct gaaaggctct                                                 20

<210> SEQ ID NO 8
<211> LENGTH: 20
<212> TYPE: DNA
<213> ORGANISM: Artificial Sequence
<220> FEATURE:
<223> OTHER INFORMATION: MYC-rv
```

```
<400> SEQUENCE: 8
aagctaacgt tgagggcat                                                   20

<210> SEQ ID NO 9
<211> LENGTH: 20
<212> TYPE: DNA
<213> ORGANISM: Artificial Sequence
<220> FEATURE:
<223> OTHER INFORMATION: P21-fw

<400> SEQUENCE: 9
tggagactct cagggtcgaa                                                  20

<210> SEQ ID NO 10
<211> LENGTH: 20
<212> TYPE: DNA
<213> ORGANISM: Artificial Sequence
<220> FEATURE:
<223> OTHER INFORMATION: P21-rv

<400> SEQUENCE: 10
ggattagggc ttcctcttgg                                                  20

<210> SEQ ID NO 11
<211> LENGTH: 20
<212> TYPE: DNA
<213> ORGANISM: Artificial Sequence
<220> FEATURE:
<223> OTHER INFORMATION: TYRO3-fw

<400> SEQUENCE: 11
aactacgaag atcgggggac                                                  20

<210> SEQ ID NO 12
<211> LENGTH: 20
<212> TYPE: DNA
<213> ORGANISM: Artificial Sequence
<220> FEATURE:
<223> OTHER INFORMATION: TYRO3-rv

<400> SEQUENCE: 12
ccaggccttt taggttgtga                                                  20

<210> SEQ ID NO 13
<211> LENGTH: 26
<212> TYPE: DNA
<213> ORGANISM: Artificial Sequence
<220> FEATURE:
<223> OTHER INFORMATION: GAPDH-fw

<400> SEQUENCE: 13
aacgggaagc ttgtcatcaa tggaaa                                           26

<210> SEQ ID NO 14
<211> LENGTH: 21
<212> TYPE: DNA
<213> ORGANISM: Artificial Sequence
<220> FEATURE:
<223> OTHER INFORMATION: GAPDH-rv

<400> SEQUENCE: 14
gcatcagcag aggggggcaga g                                               21
```